United States Patent
Morawa et al.

(10) Patent No.: US 12,161,674 B2
(45) Date of Patent: Dec. 10, 2024

(54) CRISPR-CAS9 MODIFIED CD34+ HUMAN HEMATOPOIETIC STEM AND PROGENITOR CELLS AND USES THEREOF

(71) Applicant: Vertex Pharmaceuticals Incorporated, Boston, MA (US)

(72) Inventors: Ewelina Morawa, Cambridge, MA (US); Tirtha Chakraborty, Cambridge, MA (US); Ante Sven Lundberg, Cambridge, MA (US); Tony Ho, Cambridge, MA (US); Laura Sandler, Cambridge, MA (US); Brenda Eustace, Boston, MA (US); Jerome Rossert, Boston, MA (US); Robert Kauffman, Boston, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 700 days.

(21) Appl. No.: 16/769,926

(22) PCT Filed: Dec. 5, 2018

(86) PCT No.: PCT/US2018/063973
§ 371 (c)(1),
(2) Date: Jun. 4, 2020

(87) PCT Pub. No.: WO2019/113149
PCT Pub. Date: Jun. 13, 2019

(65) Prior Publication Data
US 2020/0384033 A1    Dec. 10, 2020

(51) Int. Cl.
| | |
|---|---|
| A61K 35/28 | (2015.01) |
| A61K 31/255 | (2006.01) |
| A61K 31/395 | (2006.01) |
| A61K 35/18 | (2015.01) |
| A61K 38/19 | (2006.01) |
| A61P 7/00 | (2006.01) |
| C12N 5/0789 | (2010.01) |
| C12N 9/22 | (2006.01) |
| C12N 15/11 | (2006.01) |

(52) U.S. Cl.
CPC ............ *A61K 35/28* (2013.01); *A61K 31/255* (2013.01); *A61K 31/395* (2013.01); *A61K 35/18* (2013.01); *A61K 38/193* (2013.01); *A61P 7/00* (2018.01); *C12N 5/0647* (2013.01); *C12N 9/22* (2013.01); *C12N 15/11* (2013.01); *C12N 2310/20* (2017.05); *C12N 2310/315* (2013.01); *C12N 2310/321* (2013.01)

(58) Field of Classification Search
CPC .......................... A61K 35/28; C12N 5/0647
See application file for complete search history.

(56) References Cited

U.S. PATENT DOCUMENTS

| | | | |
|---|---|---|---|
| 9,738,693 B2 | 8/2017 | Telford et al. | |
| 9,840,538 B2 | 12/2017 | Telford et al. | |
| 2015/0044772 A1 | 2/2015 | Zhao | |
| 2015/0132269 A1 | 5/2015 | Orkin et al. | |
| 2015/0166969 A1 | 6/2015 | Takeuchi et al. | |
| 2015/0168547 A1 | 6/2015 | Lee et al. | |
| 2015/0183025 A1 | 7/2015 | Aoki | |
| 2015/0307867 A1 | 10/2015 | Orkin et al. | |
| 2016/0029604 A1 | 2/2016 | Fahrenkrug et al. | |
| 2016/0168594 A1 | 6/2016 | Zhang et al. | |
| 2016/0289675 A1 | 10/2016 | Ryan et al. | |
| 2017/0191123 A1 | 7/2017 | Kim et al. | |
| 2017/0218372 A1* | 8/2017 | Milsom .................... | C12N 7/00 |
| 2018/0016589 A1 | 1/2018 | Gao et al. | |
| 2018/0094033 A1 | 4/2018 | Telford et al. | |
| 2018/0112213 A1 | 4/2018 | Welstead et al. | |
| 2018/0119138 A1 | 5/2018 | Bauer et al. | |
| 2018/0119140 A1 | 5/2018 | Porteus et al. | |
| 2018/0179521 A1 | 6/2018 | Rahdar et al. | |
| 2019/0201553 A1 | 7/2019 | Cowan et al. | |
| 2019/0284542 A1 | 9/2019 | Chakraborty et al. | |
| 2020/0330609 A1 | 10/2020 | Cowan et al. | |
| 2021/0180091 A1 | 6/2021 | Chakraborty et al. | |
| 2022/0211874 A1 | 7/2022 | Cowan et al. | |

FOREIGN PATENT DOCUMENTS

| | | |
|---|---|---|
| CN | 104955943 A | 9/2015 |
| JP | 2000201672 A | 7/2000 |
| JP | 2019-500043 A | 1/2019 |
| JP | 2019-513407 A | 5/2019 |
| WO | WO 2013/126794 A1 | 8/2013 |
| WO | WO 2013/176772 A1 | 11/2013 |
| WO | WO 2014/093712 A1 | 6/2014 |
| WO | WO 2014/204723 A1 | 12/2014 |

(Continued)

OTHER PUBLICATIONS

Brendel et al. Lineage-specific BCL11A knockdown circumvents toxicities and reverses sickle phenotype. Journal of Clinical Investigation 2016, 126;10:3868-3878. (Year: 2016).*
Staahl et al. Efficient genome editing in the mouse brain by local delivery of engineered Cas9 ribonucleoprotein complexes. Nature Biotechnology 2017, 35;5:431-434. (Year: 2017).*
Svalgaard et al. Low-molecular-weight carbohydrate pentaisomaltose may replace dimethyl sulfoxide as a safer cryoprotectant for cryopreservation of peripheral blood stem cells. Transplantation and Cellular Engineering 2016, 56:1088-1095. (Year: 2016).*
Addgene product datasheet, 2022. (Year: 2022).*
Jackson Laboratory product datasheet, 2019. (Year: 2019).*
Bauer et al. An erythroid enhancer of BCL11A subject to genetic variation determines fetal hemoglobin level. Science 2013, supplementary material. (Year: 2013).*

(Continued)

*Primary Examiner* — Allison M Fox
*Assistant Examiner* — Jennifer S Spence
(74) *Attorney, Agent, or Firm* — McNeill PLLC

(57) ABSTRACT

Provided herein, in some embodiments, are methods and compositions for treatment of subjects with β-thalassemia and subjects with severe sickle cell disease using autologous CRISPR-Cas9 modified CD34+ human hematopoietic stem and progenitor cells.

16 Claims, 4 Drawing Sheets

Specification includes a Sequence Listing.

(56) References Cited

FOREIGN PATENT DOCUMENTS

| | | |
|---|---|---|
| WO | WO 2015/026885 A1 | 2/2015 |
| WO | WO 2015/073683 A2 | 5/2015 |
| WO | WO 2015/148860 A1 | 10/2015 |
| WO | WO 2015/168547 A2 | 11/2015 |
| WO | WO 2015/183025 A1 | 12/2015 |
| WO | WO 2016/135557 A2 | 9/2016 |
| WO | WO 2016/164356 A1 | 10/2016 |
| WO | WO 2016/182917 A1 | 11/2016 |
| WO | WO 2016/183298 A2 | 11/2016 |
| WO | WO 2017/077394 A2 | 5/2017 |
| WO | WO 2017/115268 A1 | 7/2017 |
| WO | WO 2017/160890 A1 | 9/2017 |
| WO | WO 2017/182881 A2 | 10/2017 |
| WO | WO 2018/081470 A1 | 5/2018 |
| WO | WO 2018/218135 A1 | 11/2018 |
| WO | WO 2019/081982 A1 | 5/2019 |

OTHER PUBLICATIONS

[No Author Listed]. Synth-a-Freeze, Product Manual. GIBCO. 2010;1-2.

Boulad et al., Safe mobilization of CD34+ cells in adults with β-thalassemia and validation of effective globin gene transfer for clinical investigation. Blood. Mar. 6, 2014;123(10):1483-86.

Cong et al., Multiplex genome engineering using CRISP/Cas systems. Sci. Feb. 15, 2013;339:819-23.

Zhang et al., Optimization of genome editing through CRISPR-Cas9 engineering. Bioengineered. Apr. 2016;7(3):166-74. doi: 10.1080/21655979.2016.1189039.

International Search Report and Written Opinion mailed on Mar. 11, 2019 for International Application No. PCT/US2018/063973.

International Preliminary Report on Patentability mailed Jun. 18, 2020 for International Application No. PCT/US2018/063973.

[No Author Listed], CRISPR Therapeutics and Vertex Announce New Clinical Data for Investigational Gene-Editing Therapy CTX001™ in Severe Hemoglobinopathies at the 25th Annual European Hematology Association (EHA) Congress. Vertex. Retrieved from: <https://news.vrtx.com/press-release/crispr-therapeutics-and-vertex-announce-new-clinical-data-investigational-gene>. Accessed on Jun. 25, 2020. 11 pages.

[No Author Listed] Geneseq Submission; GSN, Database Accession No. GS_NUC_ALERT:WO2016161380.324727. Oct. 6, 2016. 1 page.

Bauer et al., An Erythroid Enhancer of BCL11A Subject to Genetuc Variation Determines Fetal Hemoglobin Level. Science. Oct. 11, 2013;342(6155):253-257.

Bauer et al., Crispr-Cas9 Saturating Mutagenesis Reveals an Achilles Heel in the BCL11A Erythroid Enhancer for Fetal Hemoglobin Induction (by Genome Editing). Blood. Dec. 2015;126(23): 638 pages.

Bauer et al., Fine-Mapping and Genome Editing Reveal An Essential Erythroid Enhancer At The HbF-Associated BCL11A Locus. Blood. Nov. 15, 2013;122(21):437, 1 page.

Bauer et al., Hemoglobin switching's surprise: the versatile transcription factor BCL11A is a master repressor of fetal hemoglobin. Curr Opin Genet Dev. Aug. 2015;33:62-70.

Blobel et al., An international effort to cure a global health problem: A report on the 19th Hemoglobin Switching Conference. Exp Hematol. Oct. 2015;43(10):1-30.

Brinkman et al., Easy quantification of template-directed CRISPR/Cas9 editing. Nucleic Acids Res. Jun. 1, 2018;46(10):e58. Doi: 10.1093/nar/gky164.

Brinkman et al., Easy quantitative assessment of genome editing by sequence trace decomposition. Nucleic Acids Res. Dec. 16, 2014;42(22):e168. Doi: 10.1093/nar/gku936. Epub Oct. 9, 2014.

Canver et al., BCL11A enhancer dissection by Cas9-mediated in situ saturating mutagenesis. Nature. Nov. 12, 2015;527(7577):192-197.

Canver et al., Customizing the genome as therapy for the beta-hemoglobinopathies. Blood. Apr. 6, 2016;127(21):2536-45.

Deltcheva et al., CRISPR RNA maturation by trans-encoded small RNA and host factor RNase III. Nature. Mar. 31, 2011;471(7340):602-7. doi: 10.1038/nature09886.

Ferrari et al., Gene Therapy Approaches to Hemoglobinopathies. Hematology-Oncology Clinics of North America. Sep. 9, 2019;31(5):835-852.

Flomenberg et al., The use of AMD3100 plus G-CSF for autologous hematopoietic progenitor cell mobilization is superior to G-CSF alone. Blood. Sep. 1, 2005;106(5):1867-74. Epub May 12, 2005.

Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013.

Haridy, More early data revealed from landmark CRISPR gene editing human trial. New Atlas.Jun. 16, 2020. Retrieved from: <https://newatlas.com/medical/early-data-ctx001-crispr-gene-editing-human-trial/>. 6 pages.

Hendel et al., Chemically modified guide RNAs enhance CRISPR-Cas genome editing in human primary cells. Nat Biotechnol. Sep. 1, 2015;33(9):985-9. Epub Jun. 29, 2015. Author manuscript provided, available in PMC Sep. 1, 2016:14 pages. doi: 10.1038/nbt.3290.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Kuchler, Crispr puts first human in-body gene editing to test. Financial Times. Jan. 7, 2020. 6 pages.

Le Page, Three people with inherited diseases successfully treated with CRISPR. NewScientist. Jun. 12, 2020. Retrieved from: <https://www.newscientist.com/article/2246020-three-people-with-inherited-diseases-successfully-treated-with-crispr/>. 6 pages.

Li et al., Efficient CRISPR-Cas9 mediated gene disruption in primary erythroid progenitor cells. Haematologica. Jun. 2016;101(6):e216-9.

Li et al., Genome Editing in Erythroid Progenitor Cells Mediated By Crispr/Cas9. Blood. Dec. 2014; 124(21): 1345 pages.

Lin et al., Enhanced homology-directed human genome engineering by controlled timing of CRISPR/Cas9 delivery. eLIFE. Dec. 15, 2014;3:e04766, 13pages. doi: 10.7554/eLife.04766.

Mansilla-Soto et al., Cell and Gene Therapy for the Beta-Thalassemias: Advances and Prospects. Hum Gene Ther. Apr. 2016;27(4):295-304. doi: 10.1089/hum.2016.037.

Maresca et al., Obligate ligation-gated recombination (ObLiGaRe): custom-designed nuclease-mediated targeted integration through nonhomologous end joining. Genome Res. Mar. 2013;23(3):539-46. Doi: 10.1101/gr.145441.112. Epub Nov. 14, 2012.

Moreno-Mateos et al., CRISPRscan: designing highly efficient sgRNAs for CRISPR-Cas9 targeting in vivo. Nat Methods. Oct. 2015; 12(10):982-8. doi: 10.1038/nmeth.3543. Epub Aug. 31, 2015.

Mullin, CRISPR eliminated symptoms of genetic disease in 2 patients. One Zero. Nov. 20, 2019. 5 pages.

Orkin et al., Recent advances in globin research using genome-wide association studies and gene editing. Ann N Y Acad Sci. Mar. 2016;1368(1):1-11.

Parsons, Vertex reveals promising data from first CRISPR-treated patients. PMLive. Nov. 20, 2020. Retrieved from: <http://www.pmlive.com/pharma_news/vertex_reveals_promising_data_from_first_crispr-treated_patients_1317564>. 2 pages.

Roosjen et al., Transcriptional regulators Myb and BCL11A interplay with DNA methyltransferase 1 in developmental silencing of embryonic and fetal ?-like globin genes. FASEB J. Apr. 2014;28(4):1610-20. Epub Dec. 26, 2013.

Sanjana et al., Improved vectors and genome-wide libraries for CRISPR screening. Nat Methods. Aug. 2014;11(8):783-4. doi: 10.1038/nmeth.3047.

Sanjana et al., Supplementary Materials: Improved vectors and genome-wide libraries for CRISPR screening. Nat Methods. Aug. 2014;11(8):22 pages. doi: 10.1038/nmeth.3047.

Stein et al., Compilation of Press Releases. Vertex, CRISPR Therapeutics. Nov. 19, 2019. 40 pages.

(56) References Cited

OTHER PUBLICATIONS

Stein, A Year In, 1st Patient To Get Gene Editing For Sickle Cell Disease Is Thriving. NPR. Jun. 23, 2020. Retrieved from: <https://www.npr.org/sections/health-shots/2020/06/23/877543610/a-year-in-1st-patient-to-get-gene-editing-for-sickle-cell-disease-is-thriving>. 26 pages.
Suzuki et al., Fetal globin gene repressors as drug targets for molecular therapies to treat the β- globinopathies. Mol Cell Biol. Oct. 1, 2014;34(19):3560-9. Epub Jul. 14, 2014.
Young, "Gene therapy cures patient with sickle cell disease" Article Image. The Sunday Times. Dec. 1, 2019. Accessed Jun. 2020. 1 page.
Zhu, Overview of guide RNA design tools for CRISPR-Cas9 genome editing technology. Front Biol. Aug. 2015;10(4):289-296. doi: 10.1007/s11515-015-1366-y.
Zipkin, CRISPR's "magnificent moment" in the clinic. Nat Biotechnol. Dec. 6, 2019. 4 pages.
U.S. Appl. No. 17/591,563, filed Feb. 2, 2022, Cowan et al.
[No Author Listed] EMA's Summary of Opinion for initial authorization of CASGEVY™, dated Dec. 14, 2023—//www.ema.europa.eu/en/documents/smop-initial/chmp-summary-positive-opinion-casgevy_en.pdf.
[No Author Listed] FDA Approved Label for CASGEVY™, https://www.fda.gov/media/174615/download?attachment, Dec. 2023, 19 pages.
[No Author Listed] FDA News Release, FDA Approves First Gene Therapies to Treat Patients with Sickle Cell Disease, https://www.fda.gov/news-events/press-announcements/fda-approves-first-gene-therapies-treat-patients-sickle-cell-disease, Dec. 8, 2023, 4 pages.
[No Author Listed] Press Release, MHRA authorizes world-first gene therapy that aims to cure sickle-cell disease and transfusion-dependent β-thalassemia, Medicines and Healthcare Products Regulatory Agency, Nov. 16, 2023.
[No Author Listed] Vertex Press Release, "Vertex Receives CHMP Positive Opinion for the First CRISPR/Cas9 Gene-Edited Therapy, CASGEVY™ (exagamglogene autotemcel), for the Treatment of Sickle Cell Disease and Transfusion-Dependent Beta Thalassemia", Boston Business Wire, Dec. 15, 2023, 4 pages.
Frangoul, H., et al., "CRISPR-Cas9 Gene Editing for Sickle Cell Disease and β-Thalassemia," The New England Journal of Medicine, Brief Report, vol. 384, No. 3, Jan. 21, 2021, pp. 252-260.
Frangoul, H., et al., "Supplementary Appendix to: CRISPR-Cas9 Gene Editing for SCD and Transfusion-Dependent β-Thalassemia," The New England Journal of Medicine, 2021;384:252-60. 29 pages.
Renault, Marion, "Gene-editing treatment shows promise for sickle cell disease," Associated Press News, published on Dec. 5, 2020. 5 pages.
Stein, Rob, "1st Patients to get CRISPR Gene-Editing Treatment Continue to Thrive", npr—MPR News, published on Dec. 15, 2020, 17 pages.
Williams, Thomas N., et al. "World Distribution, Population Genetics, and Health Burden of the Hemoglobinopathies," Cold Springs Harbor Perspectives in Medicine, Sep. 2012; 2(9):a011692 article, 14 pages.

\* cited by examiner

CRISPR-CAS9 MODIFIED CD34+ HUMAN HEMATOPOIETIC STEM AND PROGENITOR CELLS AND USES THEREOF

This application is a national stage filing under 35 U.S.C. § 371 of international application number PCT/US2018/063973, filed Dec. 5, 2018, and claims the benefit of priority under 35 U.S.C. § 119(e) of U.S. provisional application No. 62/594,689, filed Dec. 5, 2017, U.S. provisional application No. 62/664,023, filed Apr. 27, 2018, U.S. provisional application No. 62/671,770, filed May 15, 2018, U.S. provisional application No. 62/734,431, filed Sep. 21, 2018 and U.S. provisional application No. 62/734,543, filed Sep. 21, 2018; the contents of each of which are incorporated by reference herein in their entirety.

BACKGROUND

Hemoglobin (Hb), is a tetramer formed of four globin peptides, each tightly associated with a heme group that contains an atom of iron. During gestation, the predominant form of hemoglobin is fetal hemoglobin (HbF), which is composed of two α-globin chains and two γ-globin chains. Shortly before birth, there is a switch from HbF to adult hemoglobin, which contains two α-globin and two β-globin polypeptide chains. The switch from HbF to adult hemoglobin is mediated by a transcriptional switch from γ-globin to β-globin within the β-globin gene cluster located on chromosome 11.

Hemoglobinopathies are disorders caused by genetic defects that affect the production or function of hemoglobin molecules. Two of the most common of the hemoglobinopathies are β-thalassemia and sickle cell disease (SCD).

β-thalassemia is one of the most common autosomal recessive disorders worldwide with high prevalence in populations in the Mediterranean (5-15%), Middle-East and West Asia (2-5%), South-East Asia (up to 10%), and South Asia (up to 18%) (Colah, R. et al. 2010. *Expert Rev Hematol* 3, 103-117). Due to population migration, β-thalassemia is also found in Northern Europe, North and South America, Caribbean, and Australia. Currently, the worldwide living population of β-thalassemia major patients is estimated to be 200,000 that are registered and receiving treatment (Galanello, R., Origa, R., 2010. *Orphanet J Rare Dis* 5, 11).

β-thalassemia is caused by a spectrum of mutations that result in reduced or absent production of adult hemoglobin (HbA). Different forms of Hb are produced during different stages of development. Fetal hemoglobin (HbF) is the predominant Hb prior to birth and extending into the newborn period. HbF is a tetrameric globin protein containing 2γ-globin and 2α-globin chains (α2γ2). After the newborn period, the main form of Hb is HbA, a heterotetramer comprised of 2β-globin and 2α-globin chains (α2β2). HbA normally accounts for >95% of the total Hb in the blood of adults.

Treatment of transfusion-dependent β-thalassemia (TDT), in particular, includes lifelong blood transfusions every 3-6 weeks. The aim of transfusion therapy is to keep Hb levels ≥9 g/dL in order to ameliorate the symptoms and physiologic sequela of severe anemia and to maintain normal growth and development. Though chronic blood transfusion regimens are effective at preventing the hallmark symptoms and physical manifestations of disease, they introduce a large iron overload that may lead to mortality through iron associated heart and liver toxicity. To prevent this, iron overload is managed with iron chelation regimens that are usually initiated at an early age. Poor compliance with chelation regimens remains a key challenge. Despite the improvements with current therapies, there is poor quality of life and overall survival until the age of 30 years is only 55%.

SCD is one of the most common monogenic disorders affecting millions of people. It is estimated to affect over 100,000 individuals in the US and about 42,000 individuals in Europe. The most severe and prevalent form of SCD, referred to as sickle cell anemia, is an autosomal recessive disease due to homozygous mutations in which a valine replaces a glutamic acid at position 6 in the β-globin protein which leads to polymerization of deoxygenated hemoglobin and red blood cell (RBC) sickling.

SCD is a chronic disease, characterized by recurrent acute VOC that lead to acute pain, chronic hemolysis, anemia, progressive tissue injury, and organ dysfunction. The disease affects multiple organs causing acute and chronic complications such as acute chest syndrome, stroke, priapism, splenic sequestration, osteonecrosis, renal failure, pulmonary hypertension, liver disease, bone damage, limited growth, increased susceptibility to infections, fatigue, and progressive cognitive decline.

About 90% of children born with SCD in the US or EU will survive into adulthood, but their lifespan is shortened by two to three decades compared to the general population with a median age of death of approximately forty to fifty years.

SUMMARY

The present disclosure provides, in some embodiments, methods and compositions for the treatment of hemoglobinopathies, such as β-thalassemia or sickle cell disease. A gene editing technology is used to accurately and efficiently introduce genetic changes into a non-coding erythroid lineage-specific enhancer of the BCL11A gene, thus specifically down-regulating BCL11A in erythroid precursors without affecting other hematopoietic lineages. Without being bound by theory, it is thought that this noncoding change will reactivate γ-globin gene transcription, and elevate fetal hemoglobin (HbF) protein in red blood cells (RBCs), thereby ameliorate disease severity.

Thus, in some aspects, the present disclosure provides compositions that include CD34+ human hematopoietic stem and progenitor cells (hHSPCs) that have a genetic modification within a +58 DNase I hypersensitive site (DHS) within the erythroid lineage-specific enhancer of a human B-cell lymphoma 11A (BCL11A) gene. In some embodiments, the composition further comprises a serum-free cryopreservation medium, 5% dimethylsulfoxide (DMSO), dextran-40, or any combination of two or more of the foregoing reagents.

In some embodiments, the genetic modification is or comprises an (at least one) insertion, deletion, mutation, or combination thereof. In some embodiments, the genetic modification comprises an insertion and a deletion (i.e., an indel) resulting from a CRISR-Cas9-mediated modification.

In some embodiments, the genetic modification is producing by delivering to the CD34+ hHSPCs a Cas9 endonuclease (e.g., of *S. pyogenes*) (or a nucleic acid encoding a Cas9 nuclease) and a guide RNA (gRNA, such as a sgRNA) (or a nucleic acid encoding a gRNA) that targets the +58 DHS within the erythroid lineage-specific enhancer of a human BCL11A gene. In some embodiments, the gRNA comprises SEQ ID NO:1 or SEQ ID NO:2 (a modified version of SEQ ID NO:1). In some embodiments, the gRNA comprises three 2'-O-methyl-phosphorothioate residues at or near each of its 5' and 3' ends. In some embodiments, the endonuclease comprises a N-terminal SV40 nuclear localization signal (NLS) and/or a C-terminal SV40 nuclear localization signal (NLS). In some embodiments, the Cas9 and gRNA are delivered as a ribonucleoprotein complex, optionally wherein the weight ratio of the gRNA to said endonuclease is 1:1.

In some embodiments, a genetically modified hHSPC or population of hHSPCs exhibit(s) an increase in γ/(γ+α)-globin mRNA ratios of 0.1 to 0.5 relative to unmodified CD34+ hHSPCs, and/or wherein the modified CD34+ hHSPCs exhibit an increase in γ/(γ+β)-globin mRNA ratios of 0.2 to 0.6 relative to unmodified CD34+ hHSPCs. In some embodiments, a genetically modified hHSPC or population of hHSPCs exhibit(s) a HbF mean percentage of HbF/(HbF+HbA) protein levels of 15% to 50%. In some embodiments, a genetically modified hHSPC or population of hHSPCs exhibit(s) a mean allele editing frequency of 70% to 90%.

In some embodiments, at least 75% of a population of modified CD34+ hHSPCs maintain multi-lineage potential for at least sixteen weeks after administration of the modified CD34+ hHSPCs to a subject. In some embodiments, a population of modified CD34+ hHSPCs exhibit an on-target indel rate of at least 40% or at least 80%. In some embodiments, a population of modified CD34+ hHSPCs exhibit an off-target indel rate of less than 5% or less than 1%.

In other aspects, the present disclosure provides methods that include administering (e.g., via injection/IV transfusion) to a subject (e.g., a human subject) having a hemoglobinopathy a dose of CD34+ hHSPCs that comprise a genetic modification within a +58 DHS within the erythroid lineage-specific enhancer of a human BCL11A gene, wherein the hHSPCs are administered in an effective amount to reduce the number of blood transfusions administered the subject (e.g., by 50%, by 60%, by 70%, by 80%, by 90%, and/or by 2-fold, 3-fold, 4-fold, 5-fold, or more) relative to baseline and/or to increase fetal hemoglobin (HbF) levels in the subject to at least 20%. In some embodiments, the methods are methods of treating a hemoglobinopathy in a subject, such as β-thalassemia or sickle cell disease. In some embodiments, the method are methods of increasing HbF in a subject.

In some embodiments, the subject is 18 years of age or older. In some embodiments, the subject is 18 to 35 years of age. In some embodiments, the subject is older than 35 years of age. In other embodiments, the subject is younger than 18 years of age. In some embodiments, the subject is 11 years of age or older. In some embodiments, the subject is 11 to 35 years of age. In some embodiments, the subject is 2 years of age or older. In some embodiments, the subject is 2 to 35 years of age.

In some embodiments, the methods include (a) mobilizing stem cells in a subject having a hemoglobinopathy; (b) collecting CD34+ hHSPCs from the subject; (c) producing modified CD34+ hHSPCs that comprise a genetic modification in within a +58 DHS within the erythroid lineage-specific enhancer of a human BCL11A gene; and (d) administering to the subject a dose of the modified CD34+ hHSPCs of step (c) in an effective amount to reduce the number of blood transfusions administered the subject (e.g., by 50%, by 60%, by 70%, by 80%, by 90%, and/or by 2-fold, 3-fold, 4-fold, 5-fold, or more) relative to baseline and/or to increase fetal hemoglobin (HbF) levels in the subject to at least 20%. In some embodiments, the methods are methods of treating a hemoglobinopathy, such as β-thalassemia or sickle cell disease. In some embodiments, the method are methods of increasing HbF in a subject. In some embodiments, step (a) comprises administering an inhibitor of CXCR4 chemokine receptor, optionally wherein the inhibitor of CXCR4 chemokine receptor is Plerixafor, to the subject. In some embodiments, step (a) further comprises administering granulocyte colony stimulating factor (GCSF) to the subject.

In some embodiments, methods comprise administering red blood cells to the subject, optionally before mobilizing stem cells in the subject (step (a)) and/or after collecting CD34+ hHSPCs from the subject (step (b)).

In some embodiments, at least $15 \times 10^6$ CD34+ hHSPCs/kg are collected from the subject, e.g., in step (b).

In some embodiments, methods comprise administering busulfan to the subject, optionally after producing modified CD34+ hHSPCs (step (c)) and before administering a dose of said modified CD34+ hHSPCs to the subject (step (d)). In some embodiments, busulfan is administered intravenously in 4 mg/kg to 5 mg/kg doses for four days or intravenously in 0.5 mg/kg to 1 mg/kg doses every six hours for four days. In some embodiments, a dose of busulfan is adjusted based on pharmacokinetic level to achieve an area under the curve (AUC) of 4500 to 5500 µM/min, preferably 5000 µM/min.

In some embodiments, the modification of step (c) is an indel, optionally produced by delivering to the CD34+ hHSPCs a Cas9 endonuclease (e.g., a *S. pyogenes* Cas9 endonuclease) and a guide RNA (e.g., gRNA comprising a nucleotide sequence of SEQ ID NO:1 or SEQ ID NO:2) that targets the +58 DHS of a human BCL11A gene.

In some embodiments, neutrophil engraftment occurs in the subject within 35-45 days, e.g., 42 days, after administration of the modified CD34+ hHSPCs (step (d)).

In some embodiments, a subject having a hemoglobinopathy is a subject having β-thalassemia. In other embodiments, a subject having a hemoglobinopathy is a subject having sickle cell disease.

In some embodiments, the subject requires fewer (e.g., at least 50%, at least 60%, at least 70%, at least 80%, at least 90% fewer) blood transfusions within a 2-year period of the time of administration of the modified CD34+ hHSPCs, or within a 2-year period after the time of administration of the modified CD34+ hHSPCs, relative to a 2-year period before the time of administration of the modified CD34+ hHSPCs.

In some embodiments, the subject achieves transfusion reduction or transfusion independence for at least three months, at least six months, or at least twelve months following administration of the modified CD34+ hHSPCs starting three months after administration of the modified CD34+ hHSPCs.

In some embodiments, the subject exhibits a decrease (e.g., at least 10%, at least 20%, at least 30%, at least 40%, or at least 50% decrease) in parameters of iron overload relative to baseline as assessed by magnetic resonance imaging (MRI) or by change in serum ferritin level over time. In some embodiments, the decrease in parameters of iron overload includes a decrease (e.g., at least 10%, at least 20%, at least 30%, at least 40%, or at least 50% decrease) in liver iron concentration (LIC) and/or cardiac iron content (CIC).

In some embodiments, the subject is no longer in need of iron chelation therapy within a 2 to 5 year period (e.g., within 2, 3, 4, or 5 years) of the time of administration of the modified CD34+ hHSPCs, or within a 2 to 5 year period after the time of administration of the modified CD34+ hHSPCs, relative to a 2 to 5 year period before the time of administration of the modified CD34+ hHSPCs.

In some embodiments, the subject exhibits HbF levels of at least 20% for at least three months, at least six months, starting at any time at or after the time of administration of the modified CD34+ hHSPCs. In some embodiments, the subject exhibits HbF levels of at least 20% for at least three months, at least six months, starting three months or six months after the time of administration of the modified CD34+ hHSPCs. In some embodiments, the subject exhibits HbF levels of at least 20% in the absence of treatment with a secondary drug, e.g., hydroxyurea (HU).

In some embodiments, the subject exhibits a relative change, e.g., a reduction, in annualized rate of severe vaso-occlusive crises (VOC) from baseline, starting six months after administration of the modified CD34+ hHSPCs. In some embodiments, the subject exhibits an absence of VOC for at least 12 months or at least 24 months, starting six months after administration of the modified CD34+ hHSPCs.

In some embodiments, the subject experiences a change in patient reported outcomes (PROs) over time, e.g., after administration of the modified CD34+ hHSPCs, using at least one of the following assays selected from: Pain scale (11 point numerical rating scale [NRS]), EuroQol Quality of Life Scale (EQ 5D 5L), functional assessment of cancer therapy-bone marrow transplant (FACT-BMT), Patient-reported Outcome Measurement Information System (PROMIS)-Fatigue, PROMIS-Cognitive function, and Adult Sickle Cell Quality of Life Measurement System (ASCQ-Me).

In some embodiments, the subject exhibits a change in hemolytic index as measured by principal component analysis of the following four markers of hemolysis over time: reticulocyte count, serum concentrations of aspartate transaminase, lactate dehydrogenase [LDH], and total bilirubin. In some embodiments, the subject exhibits a change in tricuspid regurgitant jet velocity (TRV) over time.

In some embodiments, a method further comprises administering red blood cells to the subject, wherein the red blood cells are administered before the step of administering the modified CD34+ hHSPCs. In some embodiments, the subject has received a red blood cell (RBC) transfusion before the step of administering the modified CD34+ hHSPCs. the subject has a hemoglobin S (HbS) level of less than 30% of total Hb and/or a total Hb concentration of 11 g/dL or less.

In some embodiments, the subject exhibits an increase, optionally at least a 10% increase, in the proportion of circulating erythrocytes expressing fetal hemoglobin (F-cells) over a period of time. In some embodiments, the subject exhibits a change in inflammatory and endothelial activation markers, a change in the proportion of alleles with the genetic modification present in peripheral blood leukocytes, and/or a change in the proportion of alleles with the genetic modification present in bone marrow cells over a period of time, optionally wherein the period of time is at least three months or at least six months following administration of the modified CD34+ hHSPCs.

In some embodiments, modified CD34+ hHSPCs that are administered to a subject are modified CD34+ hHSPCs that exhibit an increase in $\gamma/(\gamma+\alpha)$-globin mRNA ratios of 0.1 to 0.5 relative to unmodified CD34+ hHSPCs, and/or wherein the modified CD34+ hHSPCs exhibit an increase in $\gamma/(\gamma+\beta)$-globin mRNA ratios of 0.2 to 0.6 relative to unmodified CD34+ hHSPCs. In some embodiments, modified CD34+ hHSPCs that are administered to a subject are modified CD34+ hHSPCs that exhibit a HbF mean percentage of HbF/(HbF+HbA) protein levels of 15% to 50%, exhibit a ratio of $(\gamma+\beta)/\alpha$-globin mRNA that is at or above 0.4, and/or exhibit a mean allele editing frequency of 70% to 90%. In some embodiments, at least 50% of the modified CD34+ hHSPCs that are administered to a subject maintain multi-lineage potential for at least sixteen weeks after administration to the subject. In some embodiments, modified CD34+ hHSPCs that are administered to a subject are modified CD34+ hHSPCs that exhibit an on-target indel rate of at least 40% or at least 80%.

In some embodiments, a subject does not exhibit neoplastic and/or myeloproliferative lesions resulting from administration of the modified CD34+ hHSPCs.

In some embodiments, a dose comprises at least $2\times10^6$ or at least $3\times10^6$ modified CD34+ hHSPCs/kg.

In some embodiments, a method further comprises administering plerixafor to the subject, wherein red blood cells are administered before the step of administering the modified CD34+ hHSPCs. In some embodiments, a method further comprises administering a granulocyte colony stimulating factor to the subject.

The details of one or more embodiments of the invention are set forth in the description below. Other features or advantages of the present invention will be apparent from the following drawings and detailed description of several embodiments, and also from the appended claims.

DETAILED DESCRIPTION

Figure 1:
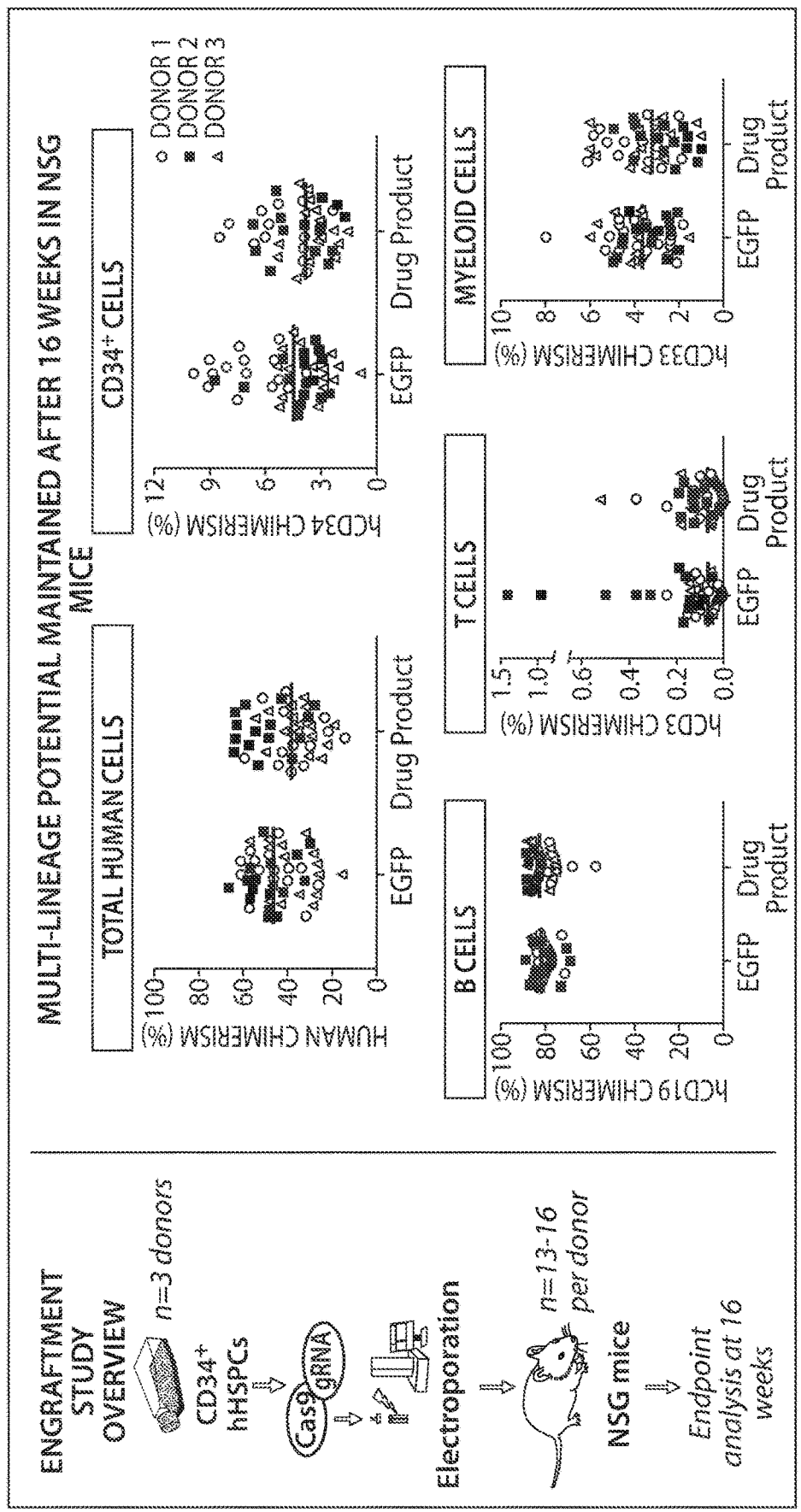
FIG. 1 is a series of graphs showing that edited cells maintain the ability to engraft and differentiate.

Currently, the only curative treatment option for transfusion-dependent β-thalassemia (TDT) is allogeneic hematopoietic stem cell transplant (allo-HSCT). There are significant risks associated with allo-HSCT such as serious infections, graft failure and graft-versus-host disease (GvHD), some of which can be fatal. As such, transplants are infrequently performed, and are offered primarily to subjects who have available human leukocyte antigen (HLA)-matched sibling donors, who are young (<16 years of age), and who do not have significant iron overload. Because of the need of a HLA-matched sibling donor, allo-HSCT is available to only <25% of eligible patients with remainder of the patients requiring lifelong transfusions and chelation. Transplants using alternative donor sources such as unrelated cord blood and haploidentical donors remain experimental due to high risk of engraftment failure and GvHD. The absence of suitable donors, the significant risks associated with transplantation, and the requirement for post-transplant immunosuppression therapy to prevent GvHD indicate an unmet medical need for novel therapies with transformative potential for subjects with TDT.

Approved therapies to prevent complications of sickle cell disease (SCD) include hydroxyurea (HU) in the US and EU and L-glutamine oral powder in the US. These therapies reduce complications of SCD; however, patients can still have breakthrough vaso-occlusive crisis (VOC). Furthermore, HU is not effective in all patients, is not well-tolerated and has carcinogenic and teratogenic risks. Allogeneic hematopoietic stem cell transplant (HSCT) is the only known cure for SCD, but HSCT is only available to about 20% of patients who have a matched donor, and graft versus-host disease (GvHD) is a known risk. Therefore, there is also significant unmet medical need for the treatment of SCD and other hemoglobinopathies.

Gene editing with the methods and compositions provided herein induce changes in the DNA sequence in autologous CD34+ hHSPCs such that upon erythroid differentiation in a patient, the expression of γ-globin is increased, leading to an increase in HbF expression levels in adult erythroid cells. The increase in HbF ameliorates the clinical manifestations of β-thalassemia and SCD.

The CRISPR-Cas9 editing therapeutic approach of the present disclosure is to restore HbF production through editing of a non-coding region in the BCL11A gene. BCL11A is a transcriptional silencer of γ-globin gene expression and hence a negative modulator of HbF.

Hemoglobinopathies

β Thalassemia

Aspects of the present disclosure provide methods for treating (e.g., ameliorating the symptoms and/or clinical manifestations) of beta thalassemia (β thalassemia). Beta thalassemia is a blood disorder that reduces the production of hemoglobin. Hemoglobin is the iron-containing protein in red blood cells that carries oxygen to cells throughout the body. A lack of beta-globin leads to a reduced amount of functional hemoglobin.

In a subject with beta thalassemia, low levels of hemoglobin lead to a lack of oxygen in many parts of the body. Without sufficient hemoglobin, red blood cells do not develop normally, causing a shortage of mature red blood cells. The low number of mature red blood cells leads to anemia, which can cause pale skin, weakness, fatigue, and more serious complications. People with beta thalassemia are at an increased risk of developing abnormal blood clots.

Beta thalassemia is classified into two types depending on the severity of symptoms: thalassemia major (also known as Cooley's anemia) and thalassemia intermedia. Of the two types, thalassemia major is more severe.

The signs and symptoms of thalassemia major appear within the first two years of life. Children develop life-threatening anemia. They do not gain weight and grow at the expected rate (failure to thrive) and may develop yellowing of the skin and whites of the eyes (jaundice). Affected individuals may have an enlarged spleen, liver, and heart, and their bones may be misshapen. Some adolescents with thalassemia major experience delayed puberty. Many people with thalassemia major have such severe symptoms that they need frequent blood transfusions to replenish their red blood cell supply. Over time, an influx of iron-containing hemoglobin from chronic blood transfusions can lead to a buildup of iron in the body, resulting in liver, heart, and hormone problems.

Thalassemia intermedia is milder than thalassemia major. The signs and symptoms of thalassemia intermedia appear in early childhood or later in life. Affected individuals have mild to moderate anemia and may also have slow growth and bone abnormalities.

Mutations in the hemoglobin gene cause beta thalassemia. Some mutations in the hemoglobin gene prevent the production of any beta-globin. The absence of beta-globin is referred to as beta-zero (β0) thalassemia. Other hemoglobin gene mutations allow some beta-globin to be produced but in reduced amounts. A reduced amount of beta-globin is called beta-plus (β+) thalassemia. The degree of impaired HbA production, resulting from the extent of incomplete (β+) or absent (β0) β-globin expression, determines the severity of β-thalassemia. Reduction in β-globin production results in an accumulation of excess, uncomplexed α-globin in erythroblasts. The clinical implications of this α-globin/β-globin imbalance are:

1) Hemolysis leading to a lack of sufficient erythrocytes and Hb to effectively transport oxygen throughout the body;
2) Oxidative damage of the cell membrane, thereby resulting in apoptosis of erythrocyte precursors and therefore ineffective erythropoiesis; and
3) Ineffective erythropoiesis which leads to morbidities such as splenomegaly, bone marrow expansion, concomitant bone deformities, and iron overload.

Having either B0 or B+ thalassemia does not necessarily predict disease severity, however; people with both types have been diagnosed with thalassemia major and thalassemia intermedia.

Patients with the HPFH phenotype have sustained HbF levels of 10% to 30% of total Hb throughout their lives, with often a pan-cellular distribution of HbF. A number of people with HPFH also carry the genetic defects for β-thalassemia or sickle cell disease. These patients who co-inherit both the HPFH and a β globin mutation have no clinical symptoms of their underlying β-thalassemia or sickle cell disease or suffer a mild form of the disease.

An increased HbF level is an ameliorating and protecting factor in β thalassemia in patients with non-transfusion-dependent thalassemia (NTDT) where HbF levels can be measured (Musallam, K. M. et al. 2012. Blood 119, 364-367).

Increased γ-globin production mitigates the pathology resulting from excess unpaired α-globin and the α/β-protein imbalance that is a hallmark of β-thalassemia. As a result, there are improvements in the ineffective erythropoiesis seen in the disease, decreased hemolysis, and increased total hemoglobin levels from the improved survival of erythrocytes containing higher levels of HbF. There appears to be no minimum threshold of HbF that is associated with lower morbidity in patients with β thalassemia, as any amount of HbF appeared to be beneficial in non-transfusion-dependent patients with β-thalassemia intermedia (Musallam, K. M. et al. 2013. *Blood* 121, 2199-2212). Resultant decrease in ineffective erythropoiesis due to increased HbF levels may also have a positive effect on iron overload and end-organ damage (Tanno, T. and Miller, J. L., 2010. *Adv Hematol* 358283).

Treatment of transfusion-dependent β-thalassemia (TDT), in particular, includes lifelong blood transfusions every 3-6 weeks. The aim of transfusion therapy is to keep Hb levels ≥9 g/dL in order to ameliorate the symptoms and physiologic sequela of severe anemia and to maintain normal growth and development. Though chronic blood transfusion regimens are effective at preventing the hallmark symptoms and physical manifestations of disease, they introduce a large iron overload that may lead to mortality through iron associated heart and liver toxicity. To prevent this, iron overload is managed with iron chelation regimens that are usually initiated at an early age. Poor compliance with chelation regimens remains a key challenge. Despite the improvements with current therapies, there is poor quality of life and overall survival until the age of 30 years is only 55%.

Sickle Cell Disease

Aspects of the present disclosure provide methods for treating (e.g., ameliorating the symptoms and/or clinical manifestations) of sickle cell disease (SCD). Sickle cell disease is a group of disorders that affects hemoglobin, the molecule in red blood cells that delivers oxygen to cells throughout the body. Subjects with this disorder have atypical hemoglobin molecules called hemoglobin S, which can distort red blood cells into a sickle, or crescent, shape.

Signs and symptoms of SCD usually begin in early childhood. Characteristic features of this disorder include a low number of red blood cells (anemia), repeated infections, and periodic episodes of pain. The severity of symptoms varies from person to person. Some subjects have mild symptoms, while others are frequently hospitalized for more serious complications.

SCD is a chronic disease, characterized by recurrent acute VOC that lead to acute pain, chronic hemolysis, anemia, progressive tissue injury, and organ dysfunction. The disease affects multiple organs causing acute and chronic complications such as acute chest syndrome, stroke, priapism, splenic sequestration, osteonecrosis, renal failure, pulmonary hypertension, liver disease, bone damage, limited growth, increased susceptibility to infections, fatigue, and progressive cognitive decline.

About 90% of children born with SCD in the US or EU will survive into adulthood, but their lifespan is shortened by two to three decades compared to the general population with a median age of death of approximately forty to fifty years.

The signs and symptoms of SCD are caused by the sickling of red blood cells. When red blood cells sickle, they break down prematurely, which can lead to anemia. Anemia can cause shortness of breath, fatigue, and delayed growth and development in children. The rapid breakdown of red blood cells may also cause yellowing of the eyes and skin, which are signs of jaundice. Painful episodes can occur when sickled red blood cells, which are stiff and inflexible, get stuck in small blood vessels. These episodes deprive tissues and organs of oxygen-rich blood and can lead to organ damage, especially in the lungs, kidneys, spleen, and brain. A particularly serious complication of SCD is high blood pressure in the blood vessels that supply the lungs (pulmonary hypertension). Pulmonary hypertension occurs in about one-third of adults with SCD and can lead to heart failure.

Mutations in the hemoglobin gene cause SCD. Hemoglobin consists of four protein subunits, typically, two subunits called alpha-globin and two subunits called beta-globin. The hemoglobin gene provides instructions for making beta-globin. Beta-globin is a component (subunit) of hemoglobin. Hemoglobin consists of four protein subunits, typically two subunits of beta-globin and two subunits of another protein called alpha-globin. Various versions of beta-globin result from different mutations in the hemoglobin gene. One particular hemoglobin gene mutation produces an abnormal version of beta-globin known as hemoglobin S (HbS). Other mutations in the hemoglobin gene lead to additional abnormal versions of beta-globin such as hemoglobin C (HbC) and hemoglobin E (HbE).

Fetal Hemoglobin

Some aspects of the present disclosure provide methods that elevate fetal hemoglobin levels in a subject, e.g., a subject having β-thalassemia, sickle cell disease, or other hemoglobinopathy. Red blood cells function mainly to transport gases into and out of cells. This is facilitated by a structural component of hemoglobin, which has the ability to bind with gases. Three types of hemoglobin are synthesized in humans depending on the stage of development. Embryonic hemoglobin is produced before birth, fetal hemoglobin (HbF) during fetal life, and adult hemoglobin after birth. Fetal hemoglobin (HbF, $\alpha_2\gamma_2$) is the main oxygen transport protein in a human fetus and includes alpha (α) and gamma (γ) subunits. HbF expression ceases about 6 months after birth. Adult hemoglobin (HbA, $\alpha_2\beta_2$) is the main oxygen transport protein in a human after ~34 weeks from birth, and includes alpha (α) and beta (β) subunits. After 34 weeks, a developmental switch results in decreased transcription of the γ-globin genes and increased transcription of β-globin genes. A replacement of glutamic acid of the beta chain by valine at the 6th position gives rise to a sickle cell disorder. This change, called hemoglobin S (HbS), is an abnormal hemoglobin. On exposure to low oxygen concentration, the HbS precipitates into elongated crystals appearing as sickled, instead of a biconcave disc. Sickle cell disease is characterized by occlusion events in the vascular that results in pain, organ failure and, occasionally, death. Since many of the forms of hemoglobinopathies are a result of the failure to produce normal β-globin protein in sufficient amounts or failure to produce normal β-globin protein entirely, increased expression of γ-globin (HbF) will ameliorate β-globin disease severity.

BCL11A Erythroid-Lineage Specific Enhancer

In some embodiments, cells of the present disclosure (e.g., CD34+ hHSPCs) comprise a genetic modification within the +58 DNase I hypersensitive site (DHS) within the erythroid lineage-specific enhancer of a human B-cell lymphoma 11A (BCL11A) gene. BCL11A is a transcriptional silencer of γ globin gene expression and hence a negative modulator of HbF (see Menzel S et al. *Nature Genetics*. 2007; 39(10):1197-9; Lettre G et. al. *PNAS*. 2008; 105(33): 11869-74; and Uda M et. al. *PNAS*. 2008; 105(5):1620-5, each of which is incorporated herein in its entirety). BCL11A is located on Chromosome 2 and ranges from 60,451,167-60,553,567 base pairs (bp) (GRCh38). This gene encodes a zinc finger transcription factor that represses fetal hemoglobin (HbF) and downregulates HbF expression starting at about 6 weeks after birth. The BCL11A gene contains four exons, spanning 102.4 kb of genomic DNA and includes a binding domain in intron 2 for the transcription factor GATA-1. GATA-1 binding enhances BCL11A expression which, in turn, represses HbF expression. Intron 2 contains multiple DNase I hypersensitive sites (DHS), including sites referred to as +55, +58, and +62 based on the distance in kilobases from the transcriptional start site. Naturally occurring SNPs within this region are associated with decreased BCL11A expression and increased fetal Hb levels. These SNPs are organized around three DNA Hypersensitivity sites, +55DHS, +58DHS and +62DHS. Of the three regions, the +58 DHS region, appears to be the key region associated with increased fetal Hb levels and also harbors a GATA1 transcriptional control region.

In some embodiments, the gene editing strategies, e.g., CRISPR-Cas9 gene editing strategies, of the present disclosure (for instance, through the NHEJ repair process discussed below) generate indels within the non-coding BCL11A erythroid lineage-specific enhancer on chromosome 2, thus down-regulating BCL11A in erythroid precursors with no effect expected in other hematopoietic lineages. Thus, in some embodiments, the genetic modification within the +58 DHS of a human BCL11A gene comprises at least one (on or more) indel. Without being bound by theory, it is thought that this noncoding change will reactivate γ-globin gene transcription, and elevate HbF protein in RBCs.

The transcriptional control sequence of the BCL11A gene can also be modulated or inactivated by inserting a wild-type BCL11A gene or cDNA comprising a modified transcriptional control sequence. For example, the donor for modulating or inactivating by homology directed repair (HDR)

contains the modified transcriptional control sequence of the BCL11A gene with small or large flanking homology arms to allow for annealing. HDR is essentially an error-free mechanism that uses a supplied homologous DNA sequence as a template during DSB repair. The rate of homology directed repair (HDR) is a function of the distance between the transcriptional control sequence and the cut site so choosing overlapping or nearby target sites is important. Templates can include extra sequences flanked by the homologous regions or can contain a sequence that differs from the genomic sequence, thus allowing sequence editing.

In addition to deleting, modulating, or inactivating the transcriptional control sequence of the BCL11A gene by NHEJ or HDR, a range of other options are possible. If there are small or large deletions, a cDNA can be knocked in that contains a modified transcriptional control sequence of the BCL11A gene. A full length cDNA can be knocked into any "safe harbor"—i.e., non-deleterious insertion point that is not the BCL11A gene itself—, with or without suitable regulatory sequences. If this construct is knocked-in near the BCL11A regulatory elements, it should have physiological control, similar to the normal gene. Two or more (e.g., a pair) nucleases can be used to delete transcriptional control sequence regions, though a donor would usually have to be provided to modulate or inactivate the function. In this case two gRNA and one donor sequence would be supplied.

Provided herein are cellular, ex vivo and in vivo methods for using genome engineering tools to create permanent changes to the genome by: 1) modulating or inactivating the transcriptional control sequence of the BCL11A gene, by deletions that arise due to the NHEJ pathway; 2) modulating or inactivating the transcriptional control sequence of the BCL11A gene, by HDR; 3) modulating or inactivating the transcriptional control sequence of the BCL11A gene, by deletions of at least a portion of the transcriptional control sequence and/or knocking-in a wild-type BCL11A gene or cDNA comprising a modified transcriptional control sequence into the gene locus or a safe harbour locus. Such methods use endonucleases, such as CRISPR-associated (Cas9, Cpf1 and the like) nucleases, to permanently delete, insert, or edit the transcriptional control sequence within or near the genomic locus of the BCL11A gene or other DNA sequence that encodes a regulatory element of the BCL11A gene. In this way, examples set forth in the present disclosure can help to delete, modulate, or inactivate the transcriptional control sequence of the BCL11A gene with a single treatment or a limited number of treatments (rather than deliver potential therapies for the lifetime of the patient).

Genome Editing

Genome editing generally refers to the process of modifying the nucleotide sequence of a genome, preferably in a precise or pre-determined manner. Examples of methods of genome editing described herein include methods of using site-directed nucleases to cut deoxyribonucleic acid (DNA) at precise target locations in the genome, thereby creating single-strand or double-strand DNA breaks at particular locations within the genome. Such breaks can be and regularly are repaired by natural, endogenous cellular processes, such as homology-directed repair (HDR) and NHEJ, as recently reviewed in Cox et al., Nature Medicine 21(2), 121-31 (2015). These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor can be an exogenous nucleic acid, such as a plasmid, a single-strand oligonucleotide, a double-stranded oligonucleotide, a duplex oligonucleotide or a virus, that has regions of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ", in which the genetic outcome is similar to NHEJ in that small deletions and insertions can occur at the cleavage site. MMEJ can make use of homologous sequences of a few basepairs flanking the DNA break site to drive a more favored DNA end joining repair outcome, and recent reports have further elucidated the molecular mechanism of this process; see, e.g., Cho and Greenberg, Nature 518, 174-76 (2015); Kent et al., Nature Structural and Molecular Biology, Adv. Online doi:10.1038/nsmb.2961 (2015); Mateos-Gomez et al., Nature 518, 254-57 (2015); Ceccaldi et al., Nature 528, 258-62 (2015). In some instances it may be possible to predict likely repair outcomes based on analysis of potential microhomologies at the site of the DNA break.

Each of these genome editing mechanisms can be used to create desired genomic alterations. A step in the genome editing process can be to create one or two DNA breaks, the latter as double-strand breaks or as two single-stranded breaks, in the target locus as near the site of intended mutation. This can be achieved via the use of site-directed polypeptides, as described and illustrated herein.

Site-directed polypeptides, such as a DNA endonuclease, can introduce double-strand breaks or single-strand breaks in nucleic acids, e.g., genomic DNA. The double-strand break can stimulate a cell's endogenous DNA-repair pathways (e.g., homology-dependent repair or non-homologous end joining or alternative non-homologous end joining (A-NHEJ) or microhomology-mediated end joining). NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or donor, is available. The homologous donor template can comprise sequences that can be homologous to sequences flanking the target nucleic acid cleavage site. The sister chromatid can be used by the cell as the repair template. However, for the purposes of genome editing, the repair template can be supplied as an exogenous nucleic acid, such as a plasmid, duplex oligonucleotide, single-strand oligonucleotide, double-stranded oligonucleotide, or viral nucleic acid. With exogenous donor templates, an additional nucleic acid sequence (such as a transgene) or modification (such as a single or multiple base change or a deletion) can be introduced between the flanking regions of homology so that the additional or altered nucleic acid sequence also becomes incorporated into the target locus. MMEJ can result in a genetic outcome that is similar to NHEJ in that small deletions and insertions can occur at the cleavage site. MMEJ can make use of homologous sequences of a few basepairs flanking the cleavage site to drive a favored end-joining DNA repair outcome. In some instances it may be possible to predict likely repair outcomes based on analysis of potential microhomologies in the nuclease target regions.

Thus, in some cases, homologous recombination can be used to insert an exogenous polynucleotide sequence into the target nucleic acid cleavage site. An exogenous polynucleotide sequence is termed a donor polynucleotide (or donor or donor sequence or polynucleotide donor template) herein. The donor polynucleotide, a portion of the donor polynucleotide, a copy of the donor polynucleotide, or a portion of a copy of the donor polynucleotide can be inserted into the target nucleic acid cleavage site. The donor polynucleotide can be an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

CRISPR Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders, such as virus and phage. There are three stages of CRISPR locus function: integration of new sequences into the CRISPR locus, expression of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats." When expressed, the repeats can form secondary structures (e.g., hairpins) and/or comprise unstructured single-stranded sequences. The repeats usually occur in clusters and frequently diverge between species. The repeats are regularly interspaced with unique intervening sequences referred to as "spacers," resulting in a repeat-spacer-repeat locus architecture. The spacers are identical to or have high homology with known foreign invader sequences. A spacer-repeat unit encodes a crisprRNA (crRNA), which is processed into a mature form of the spacer-repeat unit. A crRNA comprises a "seed" or spacer sequence that is involved in targeting a target nucleic acid (in the naturally occurring form in prokaryotes, the spacer sequence targets the foreign invader nucleic acid). A spacer sequence is located at the 5' or 3' end of the crRNA.

A CRISPR locus also comprises polynucleotide sequences encoding CRISPR Associated (Cas) genes. Cas genes encode endonucleases involved in the biogenesis and the interference stages of crRNA function in prokaryotes. Some Cas genes comprise homologous secondary and/or tertiary structures.

Type II CRISPR Systems crRNA biogenesis in a Type II CRISPR system in nature requires a trans-activating CRISPR RNA (tracrRNA). The tracrRNA can be modified by endogenous RNaseIII, and then hybridizes to a crRNA repeat in the pre-crRNA array. Endogenous RNaseIII can be recruited to cleave the pre-crRNA. Cleaved crRNAs can be subjected to exoribonuclease trimming to produce the mature crRNA form (e.g., 5' trimming). The tracrRNA can remain hybridized to the crRNA, and the tracrRNA and the crRNA associate with a site-directed polypeptide (e.g., Cas9). The crRNA of the crRNA-tracrRNA-Cas9 complex can guide the complex to a target nucleic acid to which the crRNA can hybridize. Hybridization of the crRNA to the target nucleic acid can activate Cas9 for targeted nucleic acid cleavage. The target nucleic acid in a Type II CRISPR system is referred to as a protospacer adjacent motif (PAM). In nature, the PAM is essential to facilitate binding of a site-directed polypeptide (e.g., Cas9) to the target nucleic acid. Type II systems (also referred to as Nmeni or CASS4) are further subdivided into Type II-A (CASS4) and II-B (CASS4a). Jinek et al., Science, 337(6096):816-821 (2012) showed that the CRISPR/Cas9 system is useful for RNA-programmable genome editing, and international patent application publication number WO2013/176772 provides numerous examples and applications of the CRISPR/Cas endonuclease system for site-specific gene editing.

Cas Genes/Polypeptides and Protospacer Adjacent Motifs

Exemplary CRISPR/Cas polypeptides include the Cas9 polypeptides in FIG. 1 of Fonfara et al., Nucleic Acids Research, 42: 2577-2590 (2014). The CRISPR/Cas gene naming system has undergone extensive rewriting since the Cas genes were discovered. FIG. 5 of Fonfara, supra, provides PAM sequences for the Cas9 polypeptides from various species.

Site-Directed Polypeptides

A site-directed polypeptide is a nuclease used in genome editing to cleave DNA. The site-directed nuclease or polypeptide can be administered to a cell or a patient as either: one or more polypeptides, or one or more mRNAs encoding the polypeptide.

In the context of a CRISPR/Cas system, the site-directed polypeptide can bind to a guide RNA that, in turn, specifies the site in the target DNA to which the polypeptide is directed. In the CRISPR/Cas system disclosed herein, the site-directed polypeptide can be an endonuclease, such as a DNA endonuclease.

A site-directed polypeptide can comprises a plurality of nucleic acid-cleaving (i.e., nuclease) domains. Two or more nucleic acid-cleaving domains can be linked together via a linker. For example, the linker can comprise a flexible linker. Linkers can comprise 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length.

Naturally-occurring wild-type Cas9 enzymes comprise two nuclease domains, a HNH nuclease domain and a RuvC domain. Herein, the "Cas9" refers to both naturally-occurring and recombinant Cas9s. Cas9 enzymes contemplated herein can comprise a HNH or HNH-like nuclease domain, and/or a RuvC or RuvC-like nuclease domain.

HNH or HNH-like domains comprise a McrA-like fold. HNH or HNH-like domains comprises two antiparallel β-strands and an α-helix. HNH or HNH-like domains comprises a metal binding site (e.g., a divalent cation binding site). HNH or HNH-like domains can cleave one strand of a target nucleic acid (e.g., the complementary strand of the crRNA targeted strand).

RuvC or RuvC-like domains comprise an RNaseH or RnaseH-like fold. RuvC/RnaseH domains are involved in a diverse set of nucleic acid-based functions including acting on both RNA and DNA. The RnaseH domain comprises 5β-strands surrounded by a plurality of α-helices. RuvC/RnaseH or RuvC/RnaseH-like domains comprise a metal binding site (e.g., a divalent cation binding site). RuvC/RnaseH or RuvC/RnaseH-like domains can cleave one strand of a target nucleic acid (e.g., the non-complementary strand of a double-stranded target DNA).

Site-directed polypeptides can introduce double-strand breaks or single-strand breaks in nucleic acids, e.g., genomic DNA. The double-strand break can stimulate a cell's endogenous DNA-repair pathways (e.g., homology-dependent repair (HDR) or NHEJ or alternative non-homologous end joining (A-NHEJ) or microhomology-mediated end joining (MMEJ)). NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or donor, is available. The homologous donor template can comprise sequences that are homologous to sequences flanking the target nucleic acid cleavage site. The sister chromatid can be used by the cell as the repair template. However, for the purposes of genome editing, the repair template can be supplied as an exogenous nucleic acid, such as a plasmid, duplex oligonucleotide, single-strand oligonucleotide or viral nucleic acid. With exogenous donor templates, an additional nucleic acid sequence (such as a transgene) or modification (such as a single or multiple base change or a deletion) can be introduced between the flanking regions of homology so that the additional or altered nucleic acid sequence also becomes incorporated into the target locus. MMEJ can result in a genetic outcome that is similar to NHEJ in that small deletions and insertions can occur at the cleavage site. MMEJ can make use of homologous sequences of a few basepairs flanking the cleavage site to drive a favored end-joining DNA repair outcome. In some instances it may be possible to predict likely repair outcomes based on analysis of potential microhomologies in the nuclease target regions.

Thus, in some cases, homologous recombination can be used to insert an exogenous polynucleotide sequence into the target nucleic acid cleavage site. An exogenous polynucleotide sequence is termed a donor polynucleotide (or donor or donor sequence) herein. The donor polynucleotide, a portion of the donor polynucleotide, a copy of the donor polynucleotide, or a portion of a copy of the donor polynucleotide can be inserted into the target nucleic acid cleavage site. The donor polynucleotide can be an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

The site-directed polypeptide can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary site-directed polypeptide [e.g., Cas9 from *S. pyogenes*, US2014/0068797 Sequence ID No. 8 or Sapranauskas et al., Nucleic Acids Res, 39(21): 9275-9282 (2011)], and various other site-directed polypeptides. The site-directed polypeptide can comprise at least 70, 75, 80, 85, 90, 95, 97, 99, or 100% identity to a wild-type site-directed polypeptide (e.g., Cas9 from *S. pyogenes*, supra) over 10 contiguous amino acids. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids. The site-directed polypeptide can comprise at least: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. The site-directed polypeptide can comprise at least: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide.

The site-directed polypeptide can comprise a modified form of a wild-type exemplary site-directed polypeptide. The modified form of the wild-type exemplary site-directed polypeptide can comprise a mutation that reduces the nucleic acid-cleaving activity of the site-directed polypeptide. The modified form of the wild-type exemplary site-directed polypeptide can have less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary site-directed polypeptide (e.g., Cas9 from *S. pyogenes*, supra). The modified form of the site-directed polypeptide can have no substantial nucleic acid-cleaving activity. When a site-directed polypeptide is a modified form that has no substantial nucleic acid-cleaving activity, it is referred to herein as "enzymatically inactive."

The modified form of the site-directed polypeptide can comprise a mutation such that it can induce a single-strand break (SSB) on a target nucleic acid (e.g., by cutting only one of the sugar-phosphate backbones of a double-strand target nucleic acid). The mutation can result in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type site directed polypeptide (e.g., Cas9 from *S. pyogenes*, supra). The mutation can result in one or more of the plurality of nucleic acid-cleaving domains retaining the ability to cleave the complementary strand of the target nucleic acid, but reducing its ability to cleave the non-complementary strand of the target nucleic acid. The mutation can result in one or more of the plurality of nucleic acid-cleaving domains retaining the ability to cleave the non-complementary strand of the target nucleic acid, but reducing its ability to cleave the complementary strand of the target nucleic acid. For example, residues in the wild-type exemplary *S. pyogenes* Cas9 polypeptide, such as Asp10, His840, Asn854 and Asn856, are mutated to inactivate one or more of the plurality of nucleic acid-cleaving domains (e.g., nuclease domains). The residues to be mutated can correspond to residues Asp10, His840, Asn854 and Asn856 in the wild-type exemplary *S. pyogenes* Cas9 polypeptide (e.g., as determined by sequence and/or structural alignment). Non-limiting examples of mutations include D10A, H840A, N854A or N856A. One skilled in the art will recognize that mutations other than alanine substitutions can be suitable.

A D10A mutation can be combined with one or more of H840A, N854A, or N856A mutations to produce a site-directed polypeptide substantially lacking DNA cleavage activity. A H840A mutation can be combined with one or more of D10A, N854A, or N856A mutations to produce a site-directed polypeptide substantially lacking DNA cleavage activity. A N854A mutation can be combined with one or more of H840A, D10A, or N856A mutations to produce a site-directed polypeptide substantially lacking DNA cleavage activity. A N856A mutation can be combined with one or more of H840A, N854A, or D10A mutations to produce a site-directed polypeptide substantially lacking DNA cleavage activity. Site-directed polypeptides that comprise one substantially inactive nuclease domain are referred to as "nickases".

Nickase variants of RNA-guided endonucleases, for example Cas9, can be used to increase the specificity of CRISPR-mediated genome editing. Wild type Cas9 is typically guided by a single guide RNA designed to hybridize with a specified ~20 nucleotide sequence in the target sequence (such as an endogenous genomic locus). However, several mismatches can be tolerated between the guide RNA and the target locus, effectively reducing the length of required homology in the target site to, for example, as little as 13 nt of homology, and thereby resulting in elevated potential for binding and double-strand nucleic acid cleavage by the CRISPR/Cas9 complex elsewhere in the target genome—also known as off-target cleavage. Because nickase variants of Cas9 each only cut one strand, in order to create a double-strand break it is necessary for a pair of nickases to bind in close proximity and on opposite strands of the target nucleic acid, thereby creating a pair of nicks, which is the equivalent of a double-strand break. This requires that two separate guide RNAs—one for each nickase—must bind in close proximity and on opposite strands of the target nucleic acid. This requirement essentially doubles the minimum length of homology needed for the double-strand break to occur, thereby reducing the likelihood that a double-strand cleavage event will occur elsewhere in the genome, where the two guide RNA sites—if they exist—are unlikely to be sufficiently close to each other to enable the double-strand break to form. As described in the art, nickases can also be used to promote HDR versus NHEJ. HDR can be used to introduce selected changes into target sites in the genome through the use of specific donor sequences that effectively mediate the desired changes.

Mutations contemplated can include substitutions, additions, and deletions, or any combination thereof. The mutation converts the mutated amino acid to alanine. The mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagines, glutamine, histidine, lysine, or arginine). The mutation converts the mutated amino acid to a non-natural amino acid (e.g., selenomethionine). The mutation converts the mutated amino acid to amino acid mimics (e.g., phosphomimics). The mutation can be a conservative mutation. For example, the mutation converts the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). The mutation can cause a shift in reading frame and/or the creation of a premature stop codon. Mutations can cause changes to regulatory regions of genes or loci that affect expression of one or more genes.

The site-directed polypeptide (e.g., variant, mutated, enzymatically inactive and/or conditionally enzymatically inactive site-directed polypeptide) can target nucleic acid. The site-directed polypeptide (e.g., variant, mutated, enzymatically inactive and/or conditionally enzymatically inactive endoribonuclease) can target DNA. The site-directed polypeptide (e.g., variant, mutated, enzymatically inactive and/or conditionally enzymatically inactive endoribonuclease) can target RNA.

The site-directed polypeptide can comprise one or more non-native sequences (e.g., the site-directed polypeptide is a fusion protein).

The site-directed polypeptide can comprise an amino acid sequence comprising at least 15% amino acid identity to a Cas9 from a bacterium (e.g., S. pyogenes), a nucleic acid binding domain, and two nucleic acid cleaving domains (i.e., a HNH domain and a RuvC domain).

The site-directed polypeptide can comprise an amino acid sequence comprising at least 15% amino acid identity to a Cas9 from a bacterium (e.g., S. pyogenes), and two nucleic acid cleaving domains (i.e., a HNH domain and a RuvC domain).

The site-directed polypeptide can comprise an amino acid sequence comprising at least 15% amino acid identity to a Cas9 from a bacterium (e.g., S. pyogenes), and two nucleic acid cleaving domains, wherein one or both of the nucleic acid cleaving domains comprise at least 50% amino acid identity to a nuclease domain from Cas9 from a bacterium (e.g., S. pyogenes).

The site-directed polypeptide can comprise an amino acid sequence comprising at least 15% amino acid identity to a Cas9 from a bacterium (e.g., S. pyogenes), two nucleic acid cleaving domains (i.e., a HNH domain and a RuvC domain), and non-native sequence (for example, a nuclear localization signal) or a linker linking the site-directed polypeptide to a non-native sequence.

The site-directed polypeptide can comprise an amino acid sequence comprising at least 15% amino acid identity to a Cas9 from a bacterium (e.g., S. pyogenes), two nucleic acid cleaving domains (i.e., a HNH domain and a RuvC domain), wherein the site-directed polypeptide comprises a mutation in one or both of the nucleic acid cleaving domains that reduces the cleaving activity of the nuclease domains by at least 50%.

The site-directed polypeptide can comprise an amino acid sequence comprising at least 15% amino acid identity to a Cas9 from a bacterium (e.g., S. pyogenes), and two nucleic acid cleaving domains (i.e., a HNH domain and a RuvC domain), wherein one of the nuclease domains comprises mutation of aspartic acid 10, and/or wherein one of the nuclease domains can comprise a mutation of histidine 840, and wherein the mutation reduces the cleaving activity of the nuclease domain(s) by at least 50%.

The one or more site-directed polypeptides, e.g. DNA endonucleases, can comprise two nickases that together effect one double-strand break at a specific locus in the genome, or four nickases that together effect or cause two double-strand breaks at specific loci in the genome. Alternatively, one site-directed polypeptide, e.g. DNA endonuclease, can effect or cause one double-strand break at a specific locus in the genome.

The site-directed polypeptide can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS.

Genome-Targeting Nucleic Acid

The present disclosure provides a genome-targeting nucleic acid that can direct the activities of an associated polypeptide (e.g., a site-directed polypeptide) to a specific target sequence within a target nucleic acid. The genome-targeting nucleic acid can be an RNA. A genome-targeting RNA is referred to as a "guide RNA" or "gRNA" herein. A guide RNA can comprise at least a spacer sequence that hybridizes to a target nucleic acid sequence of interest, and a CRISPR repeat sequence. In Type II systems, the gRNA also comprises a second RNA called the tracrRNA sequence. In the Type II guide RNA (gRNA), the CRISPR repeat sequence and tracrRNA sequence hybridize to each other to form a duplex. In the Type V guide RNA (gRNA), the crRNA forms a duplex. In both systems, the duplex can bind a site-directed polypeptide, such that the guide RNA and site-direct polypeptide form a complex. The genome-targeting nucleic acid can provide target specificity to the complex by virtue of its association with the site-directed polypeptide. The genome-targeting nucleic acid thus can direct the activity of the site-directed polypeptide.

Exemplary guide RNAs include the spacer sequences in SEQ ID NO: 1 or 2 and the sgRNA sequences in SEQ ID NO: 1 or 2 of the Sequence Listing. As is understood by the person of ordinary skill in the art, each guide RNA can be designed to include a spacer sequence complementary to its genomic target sequence. For example, each of the spacer sequences in SEQ ID NOs: 1-3 of the Sequence Listing can be put into a single RNA chimera or a crRNA (along with a corresponding tracrRNA). See Jinek et al., Science, 337, 816-821 (2012) and Deltcheva et al., Nature, 471, 602-607 (2011).

The genome-targeting nucleic acid can be a double-molecule guide RNA. The genome-targeting nucleic acid can be a single-molecule guide RNA.

A double-molecule guide RNA can comprise two strands of RNA. The first strand comprises in the 5' to 3' direction, an optional spacer extension sequence, a spacer sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) in a Type II system can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

A single-molecule guide RNA (sgRNA) in a Type V system can comprise, in the 5' to 3' direction, a minimum CRISPR repeat sequence and a spacer sequence.

The sgRNA can comprise a 20 nucleotide spacer sequence at the 5' end of the sgRNA sequence. The sgRNA can comprise a less than a 20 nucleotide spacer sequence at the 5' end of the sgRNA sequence. The sgRNA can comprise a more than 20 nucleotide spacer sequence at the 5' end of the sgRNA sequence. The sgRNA can comprise a variable length spacer sequence with 17-30 nucleotides at the 5' end of the sgRNA sequence.

The sgRNA can comprise no uracil at the 3' end of the sgRNA sequence. The sgRNA can comprise one or more uracil at the 3' end of the sgRNA sequence. For example, the sgRNA can comprise 1 uracil (U) at the 3' end of the sgRNA sequence. The sgRNA can comprise 2 uracil (UU) at the 3' end of the sgRNA sequence. The sgRNA can comprise 3 uracil (UUU) at the 3' end of the sgRNA sequence. The sgRNA can comprise 4 uracil (UUUU) at the 3' end of the sgRNA sequence. The sgRNA can comprise 5 uracil (UUUUU) at the 3' end of the sgRNA sequence. The sgRNA can comprise 6 uracil (UUUUUU) at the 3' end of the sgRNA sequence. The sgRNA can comprise 7 uracil (UUUUUUU) at the 3' end of the sgRNA sequence. The sgRNA can comprise 8 uracil (UUUUUUUU) at the 3' end of the sgRNA sequence.

The sgRNA can be unmodified or modified. For example, modified sgRNAs can comprise one or more 2'-O-methyl phosphorothioate nucleotides.

By way of illustration, guide RNAs used in the CRISPR/Cas system, or other smaller RNAs can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

Spacer Extension Sequence

In some examples of genome-targeting nucleic acids, a spacer extension sequence can modify activity, provide stability and/or provide a location for modifications of a genome-targeting nucleic acid. A spacer extension sequence can modify on- or off-target activity or specificity. In some examples, a spacer extension sequence can be provided. The spacer extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. The spacer extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. The spacer extension sequence can be less than 10 nucleotides in length. The spacer extension sequence can be between 10-30 nucleotides in length. The spacer extension sequence can be between 30-70 nucleotides in length.

The spacer extension sequence can comprise another moiety (e.g., a stability control sequence, an endoribonuclease binding sequence, a ribozyme). The moiety can decrease or increase the stability of a nucleic acid targeting nucleic acid. The moiety can be a transcriptional terminator segment (i.e., a transcription termination sequence). The moiety can function in a eukaryotic cell. The moiety can function in a prokaryotic cell. The moiety can function in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional controls, DNA methyltransferases, DNA demethylases, histone acetyltransferases, histone deacetylases, and the like).

Spacer Sequence

The spacer sequence hybridizes to a sequence in a target nucleic acid of interest. The spacer of a genome-targeting nucleic acid can interact with a target nucleic acid in a sequence-specific manner via hybridization (i.e., base pairing). The nucleotide sequence of the spacer can vary depending on the sequence of the target nucleic acid of interest.

In a CRISPR/Cas system herein, the spacer sequence can be designed to hybridize to a target nucleic acid that is located 5' of a PAM of the Cas9 enzyme used in the system. The spacer may perfectly match the target sequence or may have mismatches. Each Cas9 enzyme has a particular PAM sequence that it recognizes in a target DNA. For example, S. pyogenes recognizes in a target nucleic acid a PAM that comprises the sequence 5'-NRG-3', where R comprises either A or G, where N is any nucleotide and N is immediately 3' of the target nucleic acid sequence targeted by the spacer sequence.

The target nucleic acid sequence can comprise 20 nucleotides. The target nucleic acid can comprise less than 20 nucleotides. The target nucleic acid can comprise more than 20 nucleotides. The target nucleic acid can comprise at least: 5, 10, 15, 16, 17, 18, 19, 20, 21, 22, 23, 24, 25, 30 or more nucleotides. The target nucleic acid can comprise at most: 5, 10, 15, 16, 17, 18, 19, 20, 21, 22, 23, 24, 25, 30 or more nucleotides. The target nucleic acid sequence can comprise 20 bases immediately 5' of the first nucleotide of the PAM. For example, in a sequence comprising 5'-NNNNNNNNNNNNNNNNNNNNNRG-3' (SEQ ID NO: 3), the target nucleic acid can comprise the sequence that corresponds to the Ns, wherein N is any nucleotide, and the underlined NRG sequence is the S. pyogenes PAM.

The spacer sequence that hybridizes to the target nucleic acid can have a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some examples, the spacer sequence can comprise 20 nucleotides. In some examples, the spacer can comprise 19 nucleotides.

In some examples, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the spacer sequence and the target nucleic acid is 100% over the six contiguous 5'-most nucleotides of the target sequence of the complementary strand of the target nucleic acid. The percent complementarity between the spacer sequence and the target nucleic acid can be at least 60% over about 20 contiguous nucleotides. The length of the spacer sequence and the target nucleic acid can differ by 1 to 6 nucleotides, which may be thought of as a bulge or bulges.

The spacer sequence can be designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like.

Minimum CRISPR Repeat Sequence

A minimum CRISPR repeat sequence can be a sequence with at least about 30%, about 40%, about 50%, about 60%, about 65%, about 70%, about 75%, about 80%, about 85%, about 90%, about 95%, or 100% sequence identity to a reference CRISPR repeat sequence (e.g., crRNA from S. pyogenes).

A minimum CRISPR repeat sequence can comprise nucleotides that can hybridize to a minimum tracrRNA sequence in a cell. The minimum CRISPR repeat sequence and a minimum tracrRNA sequence can form a duplex, i.e. a base-paired double-stranded structure. Together, the minimum CRISPR repeat sequence and the minimum tracrRNA sequence can bind to the site-directed polypeptide. At least a part of the minimum CRISPR repeat sequence can hybridize to the minimum tracrRNA sequence. At least a part of the minimum CRISPR repeat sequence can comprise at least about 30%, about 40%, about 50%, about 60%, about 65%, about 70%, about 75%, about 80%, about 85%, about 90%, about 95%, or 100% complementary to the minimum tracrRNA sequence. At least a part of the minimum CRISPR repeat sequence can comprise at most about 30%, about 40%, about 50%, about 60%, about 65%, about 70%, about 75%, about 80%, about 85%, about 90%, about 95%, or 100% complementary to the minimum tracrRNA sequence.

The minimum CRISPR repeat sequence can have a length from about 7 nucleotides to about 100 nucleotides. For example, the length of the minimum CRISPR repeat sequence is from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. In some examples, the minimum CRISPR repeat sequence can be approximately 9 nucleotides in length. The minimum CRISPR repeat sequence can be approximately 12 nucleotides in length.

The minimum CRISPR repeat sequence can be at least about 60% identical to a reference minimum CRISPR repeat sequence (e.g., wild-type crRNA from *S. pyogenes*) over a stretch of at least 6, 7, or 8 contiguous nucleotides. For example, the minimum CRISPR repeat sequence can be at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum CRISPR repeat sequence over a stretch of at least 6, 7, or 8 contiguous nucleotides.

Minimum tracrRNA Sequence

A minimum tracrRNA sequence can be a sequence with at least about 30%, about 40%, about 50%, about 60%, about 65%, about 70%, about 75%, about 80%, about 85%, about 90%, about 95%, or 100% sequence identity to a reference tracrRNA sequence (e.g., wild type tracrRNA from *S. pyogenes*).

A minimum tracrRNA sequence can comprise nucleotides that hybridize to a minimum CRISPR repeat sequence in a cell. A minimum tracrRNA sequence and a minimum CRISPR repeat sequence form a duplex, i.e. a base-paired double-stranded structure. Together, the minimum tracrRNA sequence and the minimum CRISPR repeat can bind to a site-directed polypeptide. At least a part of the minimum tracrRNA sequence can hybridize to the minimum CRISPR repeat sequence. The minimum tracrRNA sequence can be at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA nt 23-48 described in Jinek et al., supra.

The minimum tracrRNA sequence can be at least about 60% identical to a reference minimum tracrRNA (e.g., wild type, tracrRNA from *S. pyogenes*) sequence over a stretch of at least 6, 7, or 8 contiguous nucleotides. For example, the minimum tracrRNA sequence can be at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about 1, 2, 3, 4, 5, 6, 7, 8, 9, or 10 or more nucleotides. The duplex between the minimum CRISPR RNA and the minimum tracrRNA can comprise at most about 1, 2, 3, 4, 5, 6, 7, 8, 9, or 10 or more nucleotides.

The duplex can comprise a mismatch (i.e., the two strands of the duplex are not 100% complementary). The duplex can comprise at least about 1, 2, 3, 4, or 5 or mismatches. The duplex can comprise at most about 1, 2, 3, 4, or 5 or mismatches. The duplex can comprise no more than 2 mismatches.

Bulges

In some cases, there can be a "bulge" in the duplex between the minimum CRISPR RNA and the minimum tracrRNA. A bulge is an unpaired region of nucleotides within the duplex. A bulge can contribute to the binding of the duplex to the site-directed polypeptide. The bulge can comprise, on one side of the duplex, an unpaired 5'-XXXY-3' where X is any purine and Y comprises a nucleotide that can form a wobble pair with a nucleotide on the opposite strand, and an unpaired nucleotide region on the other side of the duplex. The number of unpaired nucleotides on the two sides of the duplex can be different.

In one example, the bulge can comprise an unpaired purine (e.g., adenine) on the minimum CRISPR repeat strand of the bulge. In some examples, the bulge can comprise an unpaired 5'-AAGY-3' of the minimum tracrRNA sequence strand of the bulge, where Y comprises a nucleotide that can form a wobble pairing with a nucleotide on the minimum CRISPR repeat strand.

A bulge on the minimum CRISPR repeat side of the duplex can comprise at least 1, 2, 3, 4, or 5 or more unpaired nucleotides. A bulge on the minimum CRISPR repeat side of the duplex can comprise at most 1, 2, 3, 4, or 5 or more unpaired nucleotides. A bulge on the minimum CRISPR repeat side of the duplex can comprise 1 unpaired nucleotide.

A bulge on the minimum tracrRNA sequence side of the duplex can comprise at least 1, 2, 3, 4, 5, 6, 7, 8, 9, or 10 or more unpaired nucleotides. A bulge on the minimum tracrRNA sequence side of the duplex can comprise at most 1, 2, 3, 4, 5, 6, 7, 8, 9, or 10 or more unpaired nucleotides. A bulge on a second side of the duplex (e.g., the minimum tracrRNA sequence side of the duplex) can comprise 4 unpaired nucleotides.

A bulge can comprise at least one wobble pairing. In some examples, a bulge can comprise at most one wobble pairing. A bulge can comprise at least one purine nucleotide. A bulge can comprise at least 3 purine nucleotides. A bulge sequence can comprises at least 5 purine nucleotides. A bulge sequence can comprise at least one guanine nucleotide. In some examples, a bulge sequence can comprise at least one adenine nucleotide.

Hairpins

In various examples, one or more hairpins can be located 3' to the minimum tracrRNA in the 3' tracrRNA sequence.

The hairpin can start at least about 1, 2, 3, 4, 5, 6, 7, 8, 9, 10, 15, or 20 or more nucleotides 3' from the last paired nucleotide in the minimum CRISPR repeat and minimum tracrRNA sequence duplex. The hairpin can start at most about 1, 2, 3, 4, 5, 6, 7, 8, 9 or 10 or more nucleotides 3' of the last paired nucleotide in the minimum CRISPR repeat and minimum tracrRNA sequence duplex.

The hairpin can comprise at least about 1, 2, 3, 4, 5, 6, 7, 8, 9, 10, 15, or 20 or more consecutive nucleotides. The hairpin can comprise at most about 1, 2, 3, 4, 5, 6, 7, 8, 9, 10, 15, or more consecutive nucleotides.

The hairpin can comprise a CC dinucleotide (i.e., two consecutive cytosine nucleotides).

The hairpin can comprise duplexed nucleotides (e.g., nucleotides in a hairpin, hybridized together). For example, a hairpin can comprise a CC dinucleotide that is hybridized to a GG dinucleotide in a hairpin duplex of the 3' tracrRNA sequence.

One or more of the hairpins can interact with guide RNA-interacting regions of a site-directed polypeptide.

In some examples, there are two or more hairpins, and in other examples there are three or more hairpins.

3' tracrRNA Sequence

A 3' tracrRNA sequence can comprise a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from S. pyogenes).

The 3' tracrRNA sequence can have a length from about 6 nucleotides to about 100 nucleotides. For example, the 3' tracrRNA sequence can have a length from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. The 3' tracrRNA sequence can have a length of approximately 14 nucleotides.

The 3' tracrRNA sequence can be at least about 60% identical to a reference 3' tracrRNA sequence (e.g., wild type 3' tracrRNA sequence from S. pyogenes) over a stretch of at least 6, 7, or 8 contiguous nucleotides. For example, the 3' tracrRNA sequence can be at least about 60% identical, about 65% identical, about 70% identical, about 75% identical, about 80% identical, about 85% identical, about 90% identical, about 95% identical, about 98% identical, about 99% identical, or 100% identical, to a reference 3' tracrRNA sequence (e.g., wild type 3' tracrRNA sequence from S. pyogenes) over a stretch of at least 6, 7, or 8 contiguous nucleotides.

The 3' tracrRNA sequence can comprise more than one duplexed region (e.g., hairpin, hybridized region). The 3' tracrRNA sequence can comprise two duplexed regions.

The 3' tracrRNA sequence can comprise a stem loop structure. The stem loop structure in the 3' tracrRNA can comprise at least 1, 2, 3, 4, 5, 6, 7, 8, 9, 10, 15 or 20 or more nucleotides. The stem loop structure in the 3' tracrRNA can comprise at most 1, 2, 3, 4, 5, 6, 7, 8, 9 or 10 or more nucleotides. The stem loop structure can comprise a functional moiety. For example, the stem loop structure can comprise an aptamer, a ribozyme, a protein-interacting hairpin, a CRISPR array, an intron, or an exon. The stem loop structure can comprise at least about 1, 2, 3, 4, or 5 or more functional moieties. The stem loop structure can comprise at most about 1, 2, 3, 4, or 5 or more functional moieties.

The hairpin in the 3' tracrRNA sequence can comprise a P-domain. In some examples, the P-domain can comprise a double-stranded region in the hairpin.

tracrRNA Extension Sequence

A tracrRNA extension sequence may be provided whether the tracrRNA is in the context of single-molecule guides or double-molecule guides. The tracrRNA extension sequence can have a length from about 1 nucleotide to about 400 nucleotides. The tracrRNA extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, or 400 nucleotides. The tracrRNA extension sequence can have a length from about 20 to about 5000 or more nucleotides. The tracrRNA extension sequence can have a length of more than 1000 nucleotides. The tracrRNA extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. The tracrRNA extension sequence can have a length of less than 1000 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonuclease binding sequence). The functional moiety can comprise a transcriptional terminator segment (i.e., a transcription termination sequence). The functional moiety can have a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt. The functional moiety can function in a eukaryotic cell. The functional moiety can function in a prokaryotic cell. The functional moiety can function in both eukaryotic and prokaryotic cells.

Non-limiting examples of suitable tracrRNA extension functional moieties include a 3' poly-adenylated tail, a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional controls, DNA methyltransferases, DNA demethylases, histone acetyltransferases, histone deacetylases, and the like). The tracrRNA extension sequence can comprise a primer binding site or a molecular index (e.g., barcode sequence). The tracrRNA extension sequence can comprise one or more affinity tags.

Single-Molecule Guide Linker Sequence

The linker sequence of a single-molecule guide nucleic acid can have a length from about 3 nucleotides to about 100 nucleotides. In Jinek et al., supra, for example, a simple 4 nucleotide "tetraloop" (-GAAA-) was used, Science, 337 (6096):816-821 (2012). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about 100, 500, 1000, 1500, 2000, 2500, 3000, 3500, 4000, 4500, 5000, 5500, 6000, 6500, or 7000 or more nucleotides. The linker can be at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used, Science, 337 (6096):816-821 (2012), but numerous other sequences, including longer sequences can likewise be used.

The linker sequence can comprise a functional moiety. For example, the linker sequence can comprise one or more features, including an aptamer, a ribozyme, a protein-interacting hairpin, a protein binding site, a CRISPR array, an intron, or an exon. The linker sequence can comprise at least about 1, 2, 3, 4, or 5 or more functional moieties. In some examples, the linker sequence can comprise at most about 1, 2, 3, 4, or 5 or more functional moieties.

A step of the ex vivo methods of the present disclosure can comprise editing the patient specific iPSC cells using genome engineering. Alternatively, a step of the ex vivo methods of the present disclosure can comprise editing mesenchymal stem cell, or hematopoietic progenitor cell. Likewise, a step of the in vivo methods of the present disclosure can comprise editing the cells in a patient having hemoglobinopathy using genome engineering. Similarly, a step in the cellular methods of the present disclosure can comprise editing within or near a BCL11A gene or other DNA sequence that encodes a regulatory element of the BCL11A gene in a human cell by genome engineering.

Different patients with hemoglobinopathy will generally require different deletion, modulation, or inactivation strategies. Any CRISPR endonuclease may be used in the methods of the present disclosure, each CRISPR endonuclease having its own associated PAM, which may or may not be disease specific.

For example, the transcriptional control sequence of the BCL11A gene can be modulated or inactivated by deletions that arise due to the NHEJ pathway. NHEJ can be used to delete segments of the transcriptional control sequence of the BCL11A gene, either directly or by altering splice donor or acceptor sites through cleavage by one gRNA targeting several locations, or several gRNAs.

The transcriptional control sequence of the BCL11A gene can also be modulated or inactivated by inserting a wild-type BCL11A gene or cDNA comprising a modified transcriptional control sequence. For example, the donor for modulating or activating by HDR contains the modified transcriptional control sequence of the BCL11A gene with small or large flanking homology arms to allow for annealing. HDR is essentially an error-free mechanism that uses a supplied homologous DNA sequence as a template during DSB repair. The rate of homology directed repair (HDR) is a function of the distance between the transcriptional control sequence and the cut site so choosing overlapping or nearest target sites is important. Templates can include extra sequences flanked by the homologous regions or can contain a sequence that differs from the genomic sequence, thus allowing sequence editing.

In addition to modulating or inactivating the transcriptional control sequence of the BCL11A gene by NHEJ or HDR, a range of other options are possible. If there are small or large deletions, a cDNA can be knocked in that contains a modified transcriptional control sequence. A full length cDNA can be knocked into any "safe harbor", but must use a supplied or other promoter. If this construct is knocked into the correct location, it will have physiological control, similar to the normal gene. Pairs of nucleases can be used to delete gene regions, though a donor would usually have to be provided to modulate or inactivate the function. In this case two gRNA would be supplied and one donor sequence.

Some genome engineering strategies involve modulating or inactivating a transcriptional control sequence of the BCL11A gene by deleting at least a portion of the transcriptional control sequence of the BCL11A gene and/or knocking-in a wild-type BCL11A gene or cDNA comprising a modified transcriptional control sequence into the locus of the corresponding gene or a safe harbour locus by homology directed repair (HDR), which is also known as homologous recombination (HR). This strategy can modulate or inactivate the transcriptional control sequence of the BCL11A gene and reverse, treat, and/or mitigate the diseased state. Donor nucleotides for modulating/inactivating transcriptional control sequences often are small (<300 bp). This is advantageous, as HDR efficiencies may be inversely related to the size of the donor molecule. Also, it is expected that the donor templates can fit into size constrained adeno-associated virus (AAV) molecules, which have been shown to be an effective means of donor template delivery.

Homology direct repair is a cellular mechanism for repairing double-stranded breaks (DSBs). The most common form is homologous recombination. There are additional pathways for HDR, including single-strand annealing and alternative-HDR. Genome engineering tools allow researchers to manipulate the cellular homologous recombination pathways to create site-specific modifications to the genome. It has been found that cells can repair a double-stranded break using a synthetic donor molecule provided in trans. Therefore, by introducing a double-stranded break near a specific mutation and providing a suitable donor, targeted changes can be made in the genome. Specific cleavage increases the rate of HDR more than 1,000 fold above the rate of 1 in 106 cells receiving a homologous donor alone. The rate of homology directed repair (HDR) at a particular nucleotide is a function of the distance to the cut site, so choosing overlapping or nearest target sites is important. Gene editing offers the advantage over gene addition, as correcting in situ leaves the rest of the genome unperturbed.

Supplied donors for editing by HDR vary markedly but can contain the intended sequence with small or large flanking homology arms to allow annealing to the genomic DNA. The homology regions flanking the introduced genetic changes can be 30 bp or smaller, or as large as a multi-kilobase cassette that can contain promoters, cDNAs, etc. Both single-stranded and double-stranded oligonucleotide donors have been used. These oligonucleotides range in size from less than 100 nt to over many kb, though longer ssDNA can also be generated and used. Double-stranded donors can be used, including PCR amplicons, plasmids, and mini-circles. In general, it has been found that an AAV vector can be a very effective means of delivery of a donor template, though the packaging limits for individual donors is <5 kb. Active transcription of the donor increased HDR three-fold, indicating the inclusion of promoter may increase conversion. Conversely, CpG methylation of the donor decreased gene expression and HDR.

In addition to wildtype endonucleases, such as Cas9, nickase variants exist that have one or the other nuclease domain inactivated resulting in cutting of only one DNA strand. HDR can be directed from individual Cas nickases or using pairs of nickases that flank the target area. Donors can be single-stranded, nicked, or dsDNA.

The donor DNA can be supplied with the nuclease or independently by a variety of different methods, for example by transfection, nano-particle, micro-injection, or viral transduction. A range of tethering options have been proposed to increase the availability of the donors for HDR. Examples include attaching the donor to the nuclease, attaching to DNA binding proteins that bind nearby, or attaching to proteins that are involved in DNA end binding or repair.

The repair pathway choice can be guided by a number of culture conditions, such as those that influence cell cycling, or by targeting of DNA repair and associated proteins. For example, to increase HDR, key NHEJ molecules can be suppressed, such as KU70, KU80 or DNA ligase IV.

Without a donor present, the ends from a DNA break or ends from different breaks can be joined using the several nonhomologous repair pathways in which the DNA ends are joined with little or no base-pairing at the junction. In addition to canonical NHEJ, there are similar repair mechanisms, such as alt-NHEJ. If there are two breaks, the intervening segment can be deleted or inverted. NHEJ repair pathways can lead to insertions, deletions or mutations at the joints.

NHEJ was used to insert a 15-kb inducible gene expression cassette into a defined locus in human cell lines after nuclease cleavage. Maresca, M., Lin, V. G., Guo, N. & Yang, Y., Genome Res 23, 539-546 (2013).

In addition to genome editing by NHEJ or HDR, site-specific gene insertions have been conducted that use both the NHEJ pathway and HR. A combination approach may be applicable in certain settings, possibly including intron/exon borders. NHEJ may prove effective for ligation in the intron, while the error-free HDR may be better suited in the coding region.

As a further alternative, wild-type BCL11A gene or cDNA comprising a modified transcriptional control sequence can be knocked-in to the locus of the corresponding gene or knocked-in to a safe harbor site, such as AAVS1. In some examples, the methods can provide one gRNA or a pair of gRNAs that can be used to facilitate incorporation of a new sequence from a polynucleotide donor template to knock-in a part of or the entire wild-type BCL11A gene or cDNA comprising a modified transcriptional control sequence.

The methods can provide gRNA pairs that make a deletion by cutting the gene twice, one gRNA cutting at the 5' end of one or more mutations and the other gRNA cutting at the 3' end of one or more mutations that facilitates insertion of a new sequence from a polynucleotide donor template to replace the transcriptional control sequence of the BCL11A gene. The cutting can be accomplished by a pair of DNA endonucleases that each makes a DSB in the genome, or by multiple nickases that together make a DSB in the genome.

Alternatively, the methods can provide one gRNA to make one double-strand cut around a transcriptional control sequence of the BCL11A gene that facilitates insertion of a new sequence from a polynucleotide donor template to replace the transcriptional control sequence of the BCL11A gene with a wild-type BCL11A gene or cDNA comprising a modified transcriptional control sequence. The double-strand cut can be made by a single DNA endonuclease or multiple nickases that together make a DSB in the genome.

Illustrative modifications within or near the BCL11A gene or other DNA sequence that encodes a regulatory element of the BCL11A gene include replacements within or near (proximal) the transcriptional control sequence of the BCL11A gene referred to above, such as within the region of less than 3 kb, less than 2 kb, less than 1 kb, less than 0.5 kb upstream or downstream of the transcriptional control sequence.

Such variants can include replacements that are larger in the 5' and/or 3' direction than the specific replacement in question, or smaller in either direction. Accordingly, by "near" or "proximal" with respect to specific replacements, it is intended that the SSB or DSB locus associated with a desired replacement boundary (also referred to herein as an endpoint) can be within a region that is less than about 3 kb from the reference locus noted. The SSB or DSB locus can be more proximal and within 2 kb, within 1 kb, within 0.5 kb, or within 0.1 kb. In the case of small replacement, the desired endpoint can be at or "adjacent to" the reference locus, by which it is intended that the endpoint can be within 100 bp, within 50 bp, within 25 bp, or less than about 10 bp to 5 bp from the reference locus.

Examples comprising larger or smaller replacements can be expected to provide the same benefit, as long as the transcriptional control activity is modulated or inactivated. It is thus expected that many variations of the replacements described and illustrated herein can be effective for ameliorating hemoglobinopathies.

Another genome engineering strategy involves exon or intron deletion. Targeted deletion of specific exons or introns can be an attractive strategy for treating a large subset of patients with a single therapeutic cocktail. Deletions can either be single exon or intron deletions or multi-exon or intron deletions. While multi-exon deletions can reach a larger number of patients, for larger deletions the efficiency of deletion greatly decreases with increased size. Therefore, deletions range can be from 40 to 10,000 base pairs (bp) in size. For example, deletions can range from 40-100; 100-300; 300-500; 500-1,000; 1,000-2,000; 2,000-3,000; 3,000-5,000; or 5,000-10,000 base pairs in size. It may be desirable to delete an intron if the intron contains a regulatory element, such as a transcriptional control element (e.g., a transcription factor binding site).

In order to ensure that the pre-mRNA is properly processed following deletion, the surrounding splicing signals can be deleted. Splicing donor and acceptors are generally within 100 base pairs of the neighboring intron. Therefore, in some examples, methods can provide all gRNAs that cut approximately +/−100-3100 bp with respect to each exon/intron junction of interest.

For any of the genome editing strategies, gene editing can be confirmed by sequencing or PCR analysis.

Target Sequence Selection

Shifts in the location of the 5' boundary and/or the 3' boundary relative to particular reference loci can be used to facilitate or enhance particular applications of gene editing, which depend in part on the endonuclease system selected for the editing, as further described and illustrated herein.

In a first nonlimiting example of such target sequence selection, many endonuclease systems have rules or criteria that can guide the initial selection of potential target sites for cleavage, such as the requirement of a PAM sequence motif in a particular position adjacent to the DNA cleavage sites in the case of CRISPR Type II or Type V endonucleases.

In another nonlimiting example of target sequence selection or optimization, the frequency of off-target activity for a particular combination of target sequence and gene editing endonuclease (i.e. the frequency of DSBs occurring at sites other than the selected target sequence) can be assessed relative to the frequency of on-target activity. In some cases, cells that have been correctly edited at the desired locus can have a selective advantage relative to other cells. Illustrative, but nonlimiting, examples of a selective advantage include the acquisition of attributes such as enhanced rates of replication, persistence, resistance to certain conditions, enhanced rates of successful engraftment or persistence in vivo following introduction into a patient, and other attributes associated with the maintenance or increased numbers or viability of such cells. In other cases, cells that have been correctly edited at the desired locus can be positively selected for by one or more screening methods used to identify, sort or otherwise select for cells that have been correctly edited. Both selective advantage and directed selection methods can take advantage of the phenotype associated with the correction. In some cases, cells can be edited two or more times in order to create a second modification that creates a new phenotype that is used to select or purify the intended population of cells. Such a second modification could be created by adding a second gRNA for a selectable or screenable marker. In some cases, cells can be correctly edited at the desired locus using a DNA fragment that contains the cDNA and also a selectable marker.

Whether any selective advantage is applicable or any directed selection is to be applied in a particular case, target sequence selection can also be guided by consideration of off-target frequencies in order to enhance the effectiveness of the application and/or reduce the potential for undesired alterations at sites other than the desired target. As described further and illustrated herein and in the art, the occurrence of off-target activity can be influenced by a number of factors including similarities and dissimilarities between the target site and various off-target sites, as well as the particular endonuclease used. Bioinformatics tools are available that assist in the prediction of off-target activity, and frequently such tools can also be used to identify the most likely sites of off-target activity, which can then be assessed in experimental settings to evaluate relative frequencies of off-target to on-target activity, thereby allowing the selection of sequences that have higher relative on-target activities. Illustrative examples of such techniques are provided herein, and others are known in the art.

Another aspect of target sequence selection relates to homologous recombination events. Sequences sharing regions of homology can serve as focal points for homologous recombination events that result in deletion of intervening sequences. Such recombination events occur during the normal course of replication of chromosomes and other DNA sequences, and also at other times when DNA sequences are being synthesized, such as in the case of repairs of double-strand breaks (DSBs), which occur on a regular basis during the normal cell replication cycle but can also be enhanced by the occurrence of various events (such as UV light and other inducers of DNA breakage) or the presence of certain agents (such as various chemical inducers). Many such inducers cause DSBs to occur indiscriminately in the genome, and DSBs can be regularly induced and repaired in normal cells. During repair, the original sequence can be reconstructed with complete fidelity, however, in some cases, small insertions or deletions (referred to as "indels") are introduced at the DSB site.

DSBs can also be specifically induced at particular locations, as in the case of the endonucleases systems described herein, which can be used to cause directed or preferential gene modification events at selected chromosomal locations. The tendency for homologous sequences to be subject to recombination in the context of DNA repair (as well as replication) can be taken advantage of in a number of circumstances, and is the basis for one application of gene editing systems, such as CRISPR, in which homology directed repair is used to insert a sequence of interest, provided through use of a "donor" polynucleotide, into a desired chromosomal location.

Regions of homology between particular sequences, which can be small regions of "microhomology" that can comprise as few as ten basepairs or less, can also be used to bring about desired deletions. For example, a single DSB can be introduced at a site that exhibits microhomology with a nearby sequence. During the normal course of repair of such DSB, a result that occurs with high frequency is the deletion of the intervening sequence as a result of recombination being facilitated by the DSB and concomitant cellular repair process.

In some circumstances, however, selecting target sequences within regions of homology can also give rise to much larger deletions, including gene fusions (when the deletions are in coding regions), which may or may not be desired given the particular circumstances.

The examples provided herein further illustrate the selection of various target regions for the creation of DSBs designed to induce replacements that result in the modulation or inactivation of transcriptional control protein activity, as well as the selection of specific target sequences within such regions that are designed to minimize off-target events relative to on-target events.

Nucleic Acid Modifications

In some cases, polynucleotides introduced into cells can comprise one or more modifications that can be used individually or in combination, for example, to enhance activity, stability or specificity, alter delivery, reduce innate immune responses in host cells, or for other enhancements, as further described herein and known in the art.

In certain examples, modified polynucleotides can be used in the CRISPR/Cas9 system, in which case the guide RNAs (either single-molecule guides or double-molecule guides) and/or a DNA or an RNA encoding a Cas endonuclease introduced into a cell can be modified, as described and illustrated below. Such modified polynucleotides can be used in the CRISPR/Cas9 system to edit any one or more genomic loci.

Using the CRISPR/Cas9 system for purposes of nonlimiting illustrations of such uses, modifications of guide RNAs can be used to enhance the formation or stability of the CRISPR/Cas9 genome editing complex comprising guide RNAs, which can be single-molecule guides or double-molecule, and a Cas endonuclease. Modifications of guide RNAs can also or alternatively be used to enhance the initiation, stability or kinetics of interactions between the genome editing complex with the target sequence in the genome, which can be used, for example, to enhance on-target activity. Modifications of guide RNAs can also or alternatively be used to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in aspects in which a Cas endonuclease is introduced into the cell to be edited via an RNA that needs to be translated in order to generate endonuclease, because increasing the half-life of guide RNAs introduced at the same time as the RNA encoding the endonuclease can be used to increase the time that the guide RNAs and the encoded Cas endonuclease co-exist in the cell.

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease that are introduced into a cell, including, without limitation, modifications that enhance the stability of the RNA (such as by increasing its degradation by RNAses present in the cell), modifications that enhance translation of the resulting product (i.e. the endonuclease), and/or modifications that decrease the likelihood or degree to which the RNAs introduced into cells elicit innate immune responses.

Combinations of modifications, such as the foregoing and others, can likewise be used. In the case of CRISPR/Cas9, for example, one or more types of modifications can be made to guide RNAs (including those exemplified above), and/or one or more types of modifications can be made to RNAs encoding Cas endonuclease (including those exemplified above).

By way of illustration, guide RNAs used in the CRISPR/Cas9 system, or other smaller RNAs can be readily synthesized by chemical means, enabling a number of modifications to be readily incorporated, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach that can be used for generating chemically-modified RNAs of greater length is to produce two or more molecules that are ligated together. Much longer RNAs, such as those encoding a Cas9 endonuclease, are more readily generated enzymatically. While fewer types of modifications are available for use in enzymatically produced RNAs, there are still modifications that can be used to, e.g., enhance stability, reduce the likelihood or degree of innate immune response, and/or enhance other attributes, as described further below and in the art; and new types of modifications are regularly being developed.

By way of illustration of various types of modifications, especially those used frequently with smaller chemically synthesized RNAs, modifications can comprise one or more nucleotides modified at the 2' position of the sugar, in some aspects a 2'-O-alkyl, 2'-O-alkyl-O-alkyl, or 2'-fluoro-modified nucleotide. In some examples, RNA modifications can comprise 2'-fluoro, 2'-amino or 2' O-methyl modifications on the ribose of pyrimidines, abasic residues, or an inverted base at the 3' end of the RNA. Such modifications can be routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligonucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly CH2-NH—O—CH2, CH, ~N(CH3)~O~CH2 (known as a methylene(methylimino) or MMI backbone), CH—O—N (CH3)-CH2, CH2-N(CH3)-N(CH3)-CH2 and O—N(CH3)-CH2-CH2 backbones, wherein the native phosphodiester backbone is represented as O— P—O—CH); amide backbones [see De Mesmaeker et al., Ace. Chem. Res., 28:366-374 (1995)]; morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch and David Corey, Biochemistry, 41(14): 4503-4510 (2002); Genesis, Volume 30, Issue 3, (2001); Heasman, Dev. Biol., 243: 209-214 (2002); Nasevicius et al., Nat. Genet., 26:216-220 (2000); Lacerra et al., Proc. Natl. Acad. Sci., 97: 9591-9596 (2000); and U.S. Pat. No. 5,034,506, issued Jul. 23, 1991.

Cyclohexenyl nucleic acid oligonucleotide mimetics are described in Wang et al., J. Am. Chem. Soc., 122: 8595-8602 (2000).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

One or more substituted sugar moieties can also be included, e.g., one of the following at the 2' position: OH, SH, SCH3, F, OCN, OCH3, OCH3 O(CH2)n CH3, O(CH2)n NH2, or O(CH2)n CH3, where n is from 1 to about 10; C1 to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some aspects, a modification includes 2'-methoxyethoxy (2'-O—CH2CH2OCH3, also known as 2'-O-(2-methoxyethyl)) (Martin et al, Helv. Chim. Acta, 1995, 78, 486). Other modifications include 2'-methoxy (2'-O—CH3), 2'-propoxy (2'-OCH2 CH2CH3) and 2'-fluoro (2'-F). Similar modifications can also be made at other positions on the oligonucleotide, particularly the 3' position of the sugar on the 3' terminal nucleotide and the 5' position of 5' terminal nucleotide. Oligonucleotides can also have sugar mimetics, such as cyclobutyls in place of the pentofuranosyl group.

In some examples, both a sugar and an internucleoside linkage, i.e., the backbone, of the nucleotide units can be replaced with novel groups. The base units can be maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide can be replaced with an amide containing backbone, for example, an aminoethylglycine backbone. The nucleobases can be retained and bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262. Further teaching of PNA compounds can be found in Nielsen et al, Science, 254: 1497-1500 (1991).

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. Kornberg, A., DNA Replication, W. H. Freeman & Co., San Francisco, pp 75-77 (1980); Gebeyehu et al., Nucl. Acids Res. 15:4513 (1997). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Further, nucleobases can comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are aspects of base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096; and US Patent Application Publication 2003/0158403.

Thus, the term "modified" refers to a non-natural sugar, phosphate, or base that is incorporated into a guide RNA, an endonuclease, or transcriptional control sequence of BCL11A or both a guide RNA and an endonuclease. It is not necessary for all positions in a given oligonucleotide to be uniformly modified, and in fact more than one of the aforementioned modifications can be incorporated in a single oligonucleotide, or even in a single nucleoside within an oligonucleotide.

The guide RNAs and/or mRNA (or DNA) encoding an endonuclease can be chemically linked to one or more moieties or conjugates that enhance the activity, cellular distribution, or cellular uptake of the oligonucleotide. Such moieties comprise, but are not limited to, lipid moieties such as a cholesterol moiety [Letsinger et al., Proc. Natl. Acad. Sci. USA, 86: 6553-6556 (1989)]; cholic acid [Manoharan et al., Bioorg. Med. Chem. Let., 4: 1053-1060 (1994)]; a thioether, e.g., hexyl-S-tritylthiol [Manoharan et al, Ann. N. Y. Acad. Sci., 660: 306-309 (1992) and Manoharan et al., Bioorg. Med. Chem. Let., 3: 2765-2770 (1993)]; a thiocholesterol [Oberhauser et al., Nucl. Acids Res., 20: 533-538 (1992)]; an aliphatic chain, e.g., dodecandiol or undecyl residues [Kabanov et al., FEBS Lett., 259: 327-330 (1990) and Svinarchuk et al., Biochimie, 75: 49-54 (1993)]; a phospholipid, e.g., di-hexadecyl-rac-glycerol or triethylammonium 1,2-di-O-hexadecyl-rac-glycero-3-H-phosphonate [Manoharan et al., Tetrahedron Lett., 36: 3651-3654 (1995) and Shea et al., Nucl. Acids Res., 18: 3777-3783 (1990)]; a polyamine or a polyethylene glycol chain [Mancharan et al., Nucleosides & Nucleotides, 14: 969-973 (1995)]; adamantane acetic acid [Manoharan et al., Tetrahedron Lett., 36: 3651-3654 (1995)]; a palmityl moiety [(Mishra et al., Biochim. Biophys. Acta, 1264: 229-237 (1995)]; or an octadecylamine or hexylamino-carbonyl-t oxycholesterol moiety [Crooke et al., J. Pharmacol. Exp. Ther., 277: 923-937 (1996)]. See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Sugars and other moieties can be used to target proteins and complexes comprising nucleotides, such as cationic polysomes and liposomes, to particular sites. For example, hepatic cell directed transfer can be mediated via asialoglycoprotein receptors (ASGPRs); see, e.g., Hu, et al., Protein Pept Lett. 21(10):1025-30 (2014). Other systems known in the art and regularly developed can be used to target biomolecules of use in the present case and/or complexes thereof to particular target cells of interest.

These targeting moieties or conjugates can include conjugate groups covalently bound to functional groups, such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this disclosure, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are typically produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that is often observed in cells following introduction of exogenous RNAs, particularly longer RNAs such as that encoding Cas9.

Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs are regularly being developed.

There are numerous commercial suppliers of modified RNAs, including for example, TriLink Biotech, AxoLabs, Bio-Synthesis Inc., Dharmacon and many others. As described by TriLink, for example, 5-Methyl-CTP can be used to impart desirable characteristics, such as increased nuclease stability, increased translation or reduced interaction of innate immune receptors with in vitro transcribed RNA. 5-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation, as illustrated in publications by Kormann et al. and Warren et al. referred to below.

It has been shown that chemically modified mRNA delivered in vivo can be used to achieve improved therapeutic effects; see, e.g., Kormann et al., Nature Biotechnology 29, 154-157 (2011). Such modifications can be used, for example, to increase the stability of the RNA molecule and/or reduce its immunogenicity. Using chemical modifications such as Pseudo-U, N6-Methyl-A, 2-Thio-U and 5-Methyl-C, it was found that substituting just one quarter of the uridine and cytidine residues with 2-Thio-U and 5-Methyl-C respectively resulted in a significant decrease in toll-like receptor (TLR) mediated recognition of the mRNA in mice. By reducing the activation of the innate immune system, these modifications can be used to effectively increase the stability and longevity of the mRNA in vivo; see, e.g., Kormann et al., supra.

It has also been shown that repeated administration of synthetic messenger RNAs incorporating modifications designed to bypass innate anti-viral responses can reprogram differentiated human cells to pluripotency. See, e.g., Warren, et al., Cell Stem Cell, 7(5):618-30 (2010). Such modified mRNAs that act as primary reprogramming proteins can be an efficient means of reprogramming multiple human cell types. Such cells are referred to as induced pluripotency stem cells (iPSCs), and it was found that enzymatically synthesized RNA incorporating 5-Methyl-CTP, Pseudo-UTP and an Anti Reverse Cap Analog (ARCA) could be used to effectively evade the cell's antiviral response; see, e.g., Warren et al., supra.

Other modifications of polynucleotides described in the art include, for example, the use of polyA tails, the addition of 5' cap analogs (such as m7G(5')ppp(5')G (mCAP)), modifications of 5' or 3' untranslated regions (UTRs), or treatment with phosphatase to remove 5' terminal phosphates—and new approaches are regularly being developed.

A number of compositions and techniques applicable to the generation of modified RNAs for use herein have been developed in connection with the modification of RNA interference (RNAi), including small-interfering RNAs (siRNAs). siRNAs present particular challenges in vivo because their effects on gene silencing via mRNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-I), that can mediate cellular responses to dsRNA, as well as Toll-like receptors (such as TLR3, TLR7 and TLR8) that can trigger the induction of cytokines in response to such molecules; see, e.g., the reviews by Angart et al., Pharmaceuticals (Basel) 6(4): 440-468 (2013); Kanasty et al., Molecular Therapy 20(3): 513-524 (2012); Burnett et al., Biotechnol J. 6(9):1130-46 (2011); Judge and MacLachlan, Hum Gene Ther 19(2):111-24 (2008); and references cited therein.

A large variety of modifications have been developed and applied to enhance RNA stability, reduce innate immune responses, and/or achieve other benefits that can be useful in connection with the introduction of polynucleotides into human cells, as described herein; see, e.g., the reviews by Whitehead K A et al., Annual Review of Chemical and Biomolecular Engineering, 2: 77-96 (2011); Gaglione and Messere, Mini Rev Med Chem, 10(7):578-95 (2010); Chernolovskaya et al, Curr Opin Mol Ther., 12(2):158-67 (2010); Deleavey et al., Curr Protoc Nucleic Acid Chem Chapter 16: Unit 16.3 (2009); Behlke, Oligonucleotides 18(4):305-19 (2008); Fucini et al., Nucleic Acid Ther 22(3): 205-210 (2012); Bremsen et al., Front Genet 3:154 (2012).

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kole, Nature Reviews Drug Discovery 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-Methyl, 2'-Fluoro, 2'-Hydro) have been associated with highly stable siRNAs for applications in vivo, as reported by Soutschek et al. Nature 432:173-178 (2004); and 2'-O-Methyl modifications have been reported to be effective in improving stability as reported by Volkov, Oligonucleotides 19:191-202 (2009). With respect to decreasing the induction of innate immune responses, modifying specific sequences with 2'-O-Methyl, 2'-Fluoro, 2'-Hydro have been reported to reduce TLR7/TLR8 interaction while generally preserving silencing activity; see, e.g., Judge et al., Mol. Ther. 13:494-505 (2006); and Cekaite et al., J. Mol. Biol. 365:90-108 (2007). Additional modifications, such as 2-thiouracil, pseudouracil, 5-methylcytosine, 5-methyluracil, and N6-methyladenosine have also been shown to minimize the immune effects mediated by TLR3, TLR7, and TLR8; see, e.g., Kariko, K. et al., Immunity 23:165-175 (2005).

As is also known in the art, and commercially available, a number of conjugates can be applied to polynucleotides, such as RNAs, for use herein that can enhance their delivery and/or uptake by cells, including for example, cholesterol, tocopherol and folic acid, lipids, peptides, polymers, linkers and aptamers; see, e.g., the review by Winkler, Ther. Deliv. 4:791-809 (2013), and references cited therein.

Codon-Optimization

A polynucleotide encoding a site-directed polypeptide can be codon-optimized according to methods standard in the art for expression in the cell containing the target DNA of interest. For example, if the intended target nucleic acid is in a human cell, a human codon-optimized polynucleotide encoding Cas9 is contemplated for use for producing the Cas9 polypeptide.

Complexes of a Genome-Targeting Nucleic Acid and a Site-Directed Polypeptide

A genome-targeting nucleic acid interacts with a site-directed polypeptide (e.g., a nucleic acid-guided nuclease such as Cas9), thereby forming a complex. The genome-targeting nucleic acid guides the site-directed polypeptide to a target nucleic acid.

RNPs

The site-directed polypeptide and genome-targeting nucleic acid can each be administered separately to a cell or a patient. On the other hand, the site-directed polypeptide can be pre-complexed with one or more genome-targeting nucleic acids (guide RNA, sgRNA, or crRNA together with a tracrRNA). The pre-complexed material can then be administered to a cell or a patient. Such pre-complexed material is known as a ribonucleoprotein particle (RNP). The site-directed polypeptide in the RNP can be, for example, a Cas9 endonuclease. The site-directed polypeptide can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS. The weight ratio of genome-targeting nucleic acid to site-directed polypeptide in the RNP can be 1:1. For example, the weight ratio of sgRNA to Cas9 endonuclease in the RNP can be 1:1. For example, the sgRNA can comprise the nucleic acid sequence of SEQ ID NO: 1 or 2, the Cas9 endonuclease can be a S. pyogenes Cas9 comprising a N-terminus SV40 NLS and a C-terminus SV40 NLS, and the weight ratio of sgRNA to Cas9 endonuclease can be 1:1.

Nucleic Acids Encoding System Components

The present disclosure provides a nucleic acid comprising a nucleotide sequence encoding a genome-targeting nucleic acid of the disclosure, a site-directed polypeptide of the disclosure, and/or any nucleic acid or proteinaceous molecule necessary to carry out the aspects of the methods of the disclosure.

The nucleic acid encoding a genome-targeting nucleic acid of the disclosure, a site-directed polypeptide of the disclosure, and/or any nucleic acid or proteinaceous molecule necessary to carry out the aspects of the methods of the disclosure can comprise a vector (e.g., a recombinant expression vector).

The term "vector" refers to a nucleic acid molecule capable of transporting another nucleic acid to which it has been linked. One type of vector is a "plasmid", which refers to a circular double-stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some examples, vectors can be capable of directing the expression of nucleic acids to which they are operatively linked. Such vectors are referred to herein as "recombinant expression vectors", or more simply "expression vectors", which serve equivalent functions.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, CA (1990). Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Additional vectors contemplated for eukaryotic target cells include, but are not limited to, the vectors pCTx-1, pCTx-2, and pCTx-3. Other vectors can be used so long as they are compatible with the host cell.

In some examples, a vector can comprise one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. The vector can be a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

For expressing small RNAs, including guide RNAs used in connection with Cas endonuclease, various promoters such as RNA polymerase III promoters, including for example U6 and H1, can be advantageous. Descriptions of and parameters for enhancing the use of such promoters are known in art, and additional information and approaches are regularly being described; see, e.g., Ma, H. et al., Molecular Therapy—Nucleic Acids 3, e161 (2014) doi:10.1038/mtna.2014.12.

The expression vector can also contain a ribosome binding site for translation initiation and a transcription terminator. The expression vector can also comprise appropriate sequences for amplifying expression. The expression vector can also include nucleotide sequences encoding non-native tags (e.g., histidine tag, hemagglutinin tag, green fluorescent protein, etc.) that are fused to the site-directed polypeptide, thus resulting in a fusion protein.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter). In some cases, the promoter can be a spatially restricted and/or temporally restricted promoter (e.g., a tissue specific promoter, a cell type specific promoter, etc.).

The nucleic acid encoding a genome-targeting nucleic acid of the disclosure and/or a site-directed polypeptide can be packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Delivery of Guide RNAs and/or Endonuclease Polynucleotides

Guide RNA polynucleotides (RNA or DNA) and/or endonuclease polynucleotide(s) (RNA or DNA) can be delivered by viral or non-viral delivery vehicles known in the art, such as electroporation, mechanical force, cell deformation (SQZ Biotech), and cell penetrating peptides. Alternatively, endonuclease polypeptide(s) can be delivered by viral or non-viral delivery vehicles known in the art, such as electroporation or lipid nanoparticles. In further alternative aspects, the DNA endonuclease can be delivered as one or more polypeptides, either alone or pre-complexed with one or more guide RNAs, or one or more crRNA together with a tracrRNA.

Electroporation is a delivery technique in which an electrical field is applied to one or more cells in order to increase the permeability of the cell membrane, which allows substances such as drugs, nucleic acids (genome-targeting nucleic acids), proteins (site-directed polypeptides), or RNPs, to be introduced into the cell. In general, electroporation works by passing thousands of volts across a distance of one to two millimeters of suspended cells in an electroporation cuvette (1.0-1.5 kV, 250-750 V/cm).

Gene Editing Using CRISPR-Cas9

Gene editing using CRISPR-Cas9 can be used, in some embodiments, to create genetic modifications within the non-coding BCL11A erythroid lineage-specific enhancer on chromosome 2 in CD34$^+$ human hematopoietic stem and progenitor cells (hHSPCs) and induced pluripotent stems cells (iPSCs) with high specificity and frequency, which will result in a phenotype similar to the naturally-occurring hereditary persistence of fetal hemoglobin (HPFH)-associated variants. These genetic modifications increase the production of HbF, which in turn ameliorate β-globin disease severity.

The CRISPR-Cas9 system is a naturally occurring defense mechanism in prokaryotes that has been repurposed as a RNA-guided DNA-targeting platform used for gene editing. It relies on the DNA nuclease Cas9, and two noncoding RNAs-crisprRNA (crRNA) and trans-activating RNA (tracrRNA)—to target the cleavage of DNA.

crRNA drives sequence recognition and specificity of the CRISPR-Cas9 complex through Watson-Crick base pairing typically with a 20 nucleotide (nt) sequence in the target DNA. Changing the sequence of the 5' 20 nt in the crRNA allows targeting of the CRISPR-Cas9 complex to specific loci. The CRISPR-Cas9 complex only binds DNA sequences that contain a sequence match to the first 20 nt of the single-guide RNA (sgRNA) if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands three bases upstream of the PAM site, leaving a double-strand break (DSB) where both strands of the DNA terminate in a base pair (a blunt end).

For the molecular reagents used in drug product production, the two RNA molecules (crRNA and tracrRNA) are joined by a linker loop (e.g., a four-nucleotide linker loop as shown in WO2017/182881 or WO2017/191503, each of which is incorporated herein by reference in its entirety) to form a chimeric single-guide RNA (sgRNA). The sgRNA (e.g., sgRNA comprising or consisting of SEQ ID NO: 1 or SEQ ID NO: 2) targets a critical erythroid-lineage specific transcription factor-binding site (GATA1). The transcription factor-binding site is located within the erythroid-lineage specific enhancer in the second intron of the BCL11A gene.

The CRISPR-Cas9 (sgRNA/Cas9) complex together forms a ribonucleoprotein complex (RNP) in situ.

After binding of CRISPR-Cas9 complex to DNA at a specific target site and formation of the site-specific DSB, the next key step is repair of the DSB. Cells use two main DNA repair pathways to repair the DSB: non-homologous end-joining (NHEJ) and homology-directed repair (HDR).

NHEJ is a robust repair mechanism that appears highly active in the majority of cell types, including non-dividing cells. NHEJ is error-prone and can often result in the removal or addition of between one and several hundred nucleotides at the site of the DSB, though such modifications are typically <20 nt. The resulting insertions and deletions (indels) can disrupt coding or noncoding regions of genes. Alternatively, HDR uses a long stretch of homologous donor DNA, provided endogenously or exogenously, to repair the DSB with high fidelity. HDR is active only in dividing cells, and occurs at a relatively low frequency in most cell types. In many embodiments of the present disclosure, NHEJ is utilized as the repair operant.

In some embodiments, the sgRNA used to produce the cells of the drug product comprises or consists of the following sequence: CUAACAGUUGCUUUUAUCACGUUUUAGAGCUAGAAAUAGCAAGUUAAAAUAA GGCUAGUCCGUUAUCAACUUGAAAAAGUGGCACCGAGUCGGUGCUUUU (SEQ ID NO: 1). In some embodiments, the sgRNA is modified. For example, the sgRNA may comprise 2'-O-methyl-phosphorothioate residues at the 5' end/or the 3' end. In some embodiments, the sgRNA comprises three 2'-O-methyl-phosphorothioate residues at the 5' end and 2'-O-methyl-phosphorothioate residues at the 3' end, as follows:
c*u*a*ACAGUUGCUUUUAUCACGUUUUAGAGCUAGAAAUAGCAAGUUAAAAUA AGGCUAGUCCGUUAUCAACUUGAAAAAGUGGCACCGAGUCGGUGCu*u*u*U (SEQ ID NO: 2), wherein the "*" denotes a 2'-O-methyl-phosphorothioate residue.

In some embodiments, the Cas9 (CRISPR associated protein 9) endonuclease is from *Streptococcus pyogenes*, although other Cas9 homologs may be used. It should be understood, that wild-type Cas9 may be used or modified versions of Cas9 (e.g., evolved versions of Cas9) may be used (e.g., Cas9 orthologues or variants), as provided herein. In some embodiments, Cas9 may be substituted with another RNA-guided endonuclease, such as Cpf1 (of a class II CRISPR/Cas system) or any known target-specific endonuclease.

Guide RNA Formulation

Guide RNAs of the present disclosure can be formulated with pharmaceutically acceptable excipients such as carriers, solvents, stabilizers, adjuvants, diluents, etc., depending upon the particular mode of administration and dosage form. Guide RNA compositions can be formulated to achieve a physiologically compatible pH, and range from a pH of about 3 to a pH of about 11, about pH 3 to about pH 7, depending on the formulation and route of administration. In some cases, the pH can be adjusted to a range from about pH 5.0 to about pH 8. In some cases, the compositions can comprise a therapeutically effective amount of at least one compound as described herein, together with one or more pharmaceutically acceptable excipients. Optionally, the compositions can comprise a combination of the compounds described herein, or can include a second active ingredient useful in the treatment or prevention of bacterial growth (for example and without limitation, anti-bacterial or anti-microbial agents), or can include a combination of reagents of the present disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

On- and Off-Target Mutation Detection by Sequencing

To sequence on-target sites and putative off-target sites, the appropriate amplification primers may be identified and reactions may be set up with these primers using the genomic DNA harvested using QuickExtract DNA extraction solution (Epicentre) from treated cells three days post-transfection. The amplification primers contain the gene specific portion flanked by adapters. The forward primer's 5' end includes a modified forward (read1) primer-binding site. The reverse primer's 5' end contains a combined modified reverse (read2) and barcode primer-binding site, in opposite orientation. The individual PCR reactions may be validated by separating on agarose gels, then purified and re-amplified. The second round forward primers contain the Illumina P5 sequence, followed by a proportion of the modified forward (read1) primer binding site. The second round reverse primers contain the Illumina P7 sequence (at the 5' end), followed by the 6-base barcode and the combined modified reverse (read2) and barcode primer binding site. The second round amplifications may be also checked on agarose gels, then purified, and quantitated using a Nano-Drop spectrophotometer. The amplification products may be pooled to match concentration and then submitted to the Emory Integrated Genomic core for library prepping and sequencing on an Illumina Miseq machine.

The sequencing reads may be sorted by barcode and then aligned to the reference sequences supplied by bioinformatics for each product. Insertion and deletion rates in the aligned sequencing reads may be detected in the region of the putative cut sites using software previously described; see, e.g., Lin et al., Nucleic Acids Res., 42: 7473-7485 (2014). The levels of insertions and deletions detected in this window may be then compared to the level seen in the same location in genomic DNA isolated from in mock transfected cells to minimize the effects of sequencing artifacts.

Mutation Detection Assays

The on- and off-target cleavage activities of Cas9 and guide RNA combinations may be measured using the mutation rates resulting from the imperfect repair of double-strand breaks by NHEJ.

On-target loci may be amplified using AccuPrime Taq DNA Polymerase High Fidelity (Life Technologies, Carlsbad, CA) following manufacturer's instructions for 40 cycles (94° C., 30 s; 52-60° C., 30 s; 68° C., 60 s) in 50 µl reactions containing 1 µl of the cell lysate, and 1 µl of each 10 µM amplification primer. T7EI mutation detection assays were performed, as per manufacturers protocol [Reyon et al., Nat. Biotechnol., 30: 460-465 (2012)], with the digestions separated on 2% agarose gels and quantified using ImageJ [Guschin et al., Methods Mol. Biol., 649: 247-256 (2010)]. The assays may determine the percentage of insertions/deletions ("indels") in the bulk population of cells.

Human Cells

For ameliorating hemoglobinopathies, as described and illustrated herein, the principal targets for gene editing are human cells. For example, in the ex vivo methods, the human cells can be somatic cells, which after being modified using the techniques as described, can give rise to progenitor cells (e.g., CD34+ hHSPCs). For example, in the in vivo methods, the human cells can be a bone marrow cell, a hematopoietic progenitor cell, or a CD34+ cell.

By performing gene editing in autologous cells that are derived from and therefore already completely matched with the patient in need, it is possible to generate cells that can be safely re-introduced into the patient, and effectively give rise to a population of cells that can be effective in ameliorating one or more clinical conditions associated with the patient's disease.

Progenitor cells (also referred to as stem cells herein) are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one aspect, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell that itself is derived from a multipotent cell, and so on. While each of these multipotent cells may be considered stem cells, the range of cell types that each can give rise to may vary considerably. Some differentiated cells also have the capacity to give rise to cells of greater developmental potential. Such capacity may be natural or may be induced artificially upon treatment with various factors. In many biological instances, stem cells can also be "multipotent" because they can produce progeny of more than one distinct cell type, but this is not required for "stem-ness."

Self-renewal can be another important aspect of the stem cell. In theory, self-renewal can occur by either of two major mechanisms. Stem cells can divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

In the context of cell ontogeny, the adjective "differentiated," or "differentiating" is a relative term. A "differentiated cell" is a cell that has progressed further down the developmental pathway than the cell to which it is being compared. Thus, stem cells can differentiate into lineage-restricted precursor cells (such as a hematopoietic progenitor cell), which in turn can differentiate into other types of precursor cells further down the pathway (such as a hematopoietic precursor), and then to an end-stage differentiated cell, such as a erythrocyte, which plays a characteristic role in a certain tissue type, and may or may not retain the capacity to proliferate further.

The term "hematopoietic progenitor cell" refers to cells of a stem cell lineage that give rise to all the blood cell types, including erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells).

A "cell of the erythroid lineage" indicates that the cell being contacted is a cell that undergoes erythropoiesis, such that upon final differentiation it forms an erythrocyte or red blood cell. Such cells originate from bone marrow hematopoietic progenitor cells. Upon exposure to specific growth factors and other components of the hematopoietic microenvironment, hematopoietic progenitor cells can mature through a series of intermediate differentiation cellular types, all intermediates of the erythroid lineage, into RBCs. Thus, cells of the "erythroid lineage" comprise hematopoietic progenitor cells, rubriblasts, prorubricytes, erythroblasts, metarubricytes, reticulocytes, and erythrocytes.

The hematopoietic progenitor cell can express at least one of the following cell surface markers characteristic of hematopoietic progenitor cells: CD34+, CD59+, Thy1/CD90+, CD38lo/−, and C-kit/CD1 17+. In some examples provided herein, the hematopoietic progenitors can be CD34+.

The hematopoietic progenitor cell can be a peripheral blood stem cell obtained from the patient after the patient has been treated with one or more factors such as granulocyte colony stimulating factor (optionally in combination with Plerixaflor). CD34+ cells can be enriched using CliniMACS® Cell Selection System (Miltenyi Biotec). CD34+ cells can be stimulated in serum-free medium (e.g., CellGrow SCGM media, CellGenix) with cytokines (e.g., SCF, rhTPO, rhFLT3) before genome editing. Addition of SR1 and dmPGE2 and/or other factors is contemplated to improve long-term engraftment.

The hematopoietic progenitor cells of the erythroid lineage can have a cell surface marker characteristic of the erythroid lineage: such as CD71 and Ter1 19.

Hematopoietic stem cells (HSCs) can be an important target for gene therapy as they provide a prolonged source of the corrected cells. HSCs give rise to both the myeloid and lymphoid lineages of blood cells. Mature blood cells have a finite life-span and must be continuously replaced throughout life. Blood cells are continually produced by the proliferation and differentiation of a population of pluripotent HSCs that can be replenished by self-renewal. Bone marrow (BM) is the major site of hematopoiesis in humans and a good source for hematopoietic stem and progenitor cells (HSPCs). HSPCs can be found in small numbers in the peripheral blood (PB). In some indications or treatments their numbers increase. The progeny of HSCs mature through stages, generating multi-potential and lineage-committed progenitor cells including the lymphoid progenitor cells giving rise to the cells expressing BCL11A. B and T cell progenitors are the two cell populations requiring the activity of BCL11A, so they could be edited at the stages prior to re-arrangement, though correcting progenitors has the advantage of continuing to be a source of corrected cells. Treated cells, such as CD34+ cells, would be returned to the patient. The level of engraftment can be important, as is the ability of the cells' multilineage engraftment of gene-edited cells following CD34+ infusion in vivo.

Induced Pluripotent Stem Cells

The genetically engineered human cells described herein can be induced pluripotent stem cells (iPSCs). An advantage of using iPSCs is that the cells can be derived from the same subject to which the progenitor cells are to be administered. That is, a somatic cell can be obtained from a subject, reprogrammed to an induced pluripotent stem cell, and then re-differentiated into a progenitor cell to be administered to the subject (e.g., autologous cells). Because the progenitors are essentially derived from an autologous source, the risk of engraftment rejection or allergic response can be reduced compared to the use of cells from another subject or group of subjects. In addition, the use of iPSCs negates the need for cells obtained from an embryonic source. Thus, in one aspect, the stem cells used in the disclosed methods are not embryonic stem cells.

Although differentiation is generally irreversible under physiological contexts, several methods have been recently developed to reprogram somatic cells to iPSCs. Exemplary methods are known to those of skill in the art and are described briefly herein below.

The term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. Reprogramming can encompass complete reversion of the differentiation state of a differentiated cell (e.g., a somatic cell) to a pluripotent state or a multipotent state. Reprogramming can encompass complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain examples described herein, reprogramming of a differentiated cell (e.g., a somatic cell) can cause the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell).

Reprogramming is also distinct from promoting the self-renewal or proliferation of cells that are already pluripotent or multipotent, although the compositions and methods described herein can also be of use for such purposes, in some examples.

Many methods are known in the art that can be used to generate pluripotent stem cells from somatic cells. Any such method that reprograms a somatic cell to the pluripotent phenotype would be appropriate for use in the methods described herein.

Reprogramming methodologies for generating pluripotent cells using defined combinations of transcription factors have been described. Mouse somatic cells can be converted to ES cell-like cells with expanded developmental potential by the direct transduction of Oct4, Sox2, Klf4, and c-Myc; see, e.g., Takahashi and Yamanaka, Cell 126(4): 663-76 (2006). iPSCs resemble ES cells, as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission [see, e.g., Maherali and Hochedlinger, Cell Stem Cell. 3(6):595-605 (2008)], and tetraploid complementation.

Human iPSCs can be obtained using similar transduction methods, and the transcription factor trio, OCT4, SOX2, and NANOG, has been established as the core set of transcription factors that govern pluripotency; see, e.g., Budniatzky and Gepstein, Stem Cells Transl Med. 3(4):448-57 (2014); Barrett et al., Stem Cells Trans Med 3:1-6 sctm.2014-0121 (2014); Focosi et al., Blood Cancer Journal 4: e211 (2014); and references cited therein. The production of iPSCs can be achieved by the introduction of nucleic acid sequences encoding stem cell-associated genes into an adult, somatic cell, historically using viral vectors.

iPSCs can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 7(5):618-30 (2010). Reprogramming can be achieved by introducing a combination of nucleic acids encoding stem cell-associated genes, including, for example, Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. Reprogramming using the methods and compositions described herein can further comprise introducing one or more of Oct-3/4, a member of the Sox family, a member of the Klf family, and a member of the Myc family to a somatic cell. The methods and compositions described herein can further comprise introducing one or more of each of Oct-4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one aspect the reprogramming is not effected by a method that alters the genome. Thus, in such examples, reprogramming can be achieved, e.g., without the use of viral or plasmid vectors.

The efficiency of reprogramming (i.e., the number of reprogrammed cells) derived from a population of starting cells can be enhanced by the addition of various agents, e.g., small molecules, as shown by Shi et al., Cell-Stem Cell 2:525-528 (2008); Huangfu et al., Nature Biotechnology 26(7):795-797 (2008) and Marson et al., Cell-Stem Cell 3: 132-135 (2008). Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido)caproic hydroxamic acid), AOE (2-amino-8-oxo-9, 10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Titan Pharmaceuticals, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one case, for example, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. Detection can involve not only RT-PCR, but can also include detection of protein markers. Intracellular markers may be best identified via RT-PCR, or protein detection methods such as immunocytochemistry, while cell surface markers are readily identified, e.g., by immunocytochemistry.

The pluripotent stem cell character of isolated cells can be confirmed by tests evaluating the ability of the iPSCs to differentiate into cells of each of the three germ layers. As one example, teratoma formation in nude mice can be used to evaluate the pluripotent character of the isolated clones. The cells can be introduced into nude mice and histology and/or immunohistochemistry can be performed on a tumor arising from the cells. The growth of a tumor comprising cells from all three germ layers, for example, further indicates that the cells are pluripotent stem cells.

Creating Patient Specific iPSCs

In some embodiments, one step of the ex vivo methods of the present disclosure can involve creating a patient specific iPS cell, patient specific iPS cells, or a patient specific iPS cell line. There are many established methods in the art for creating patient specific iPS cells, as described in Takahashi and Yamanaka 2006; Takahashi, Tanabe et al. 2007. For example, the creating step can comprise: a) isolating a somatic cell, such as a skin cell or fibroblast, from the patient; and b) introducing a set of pluripotency-associated genes into the somatic cell in order to induce the cell to become a pluripotent stem cell. The set of pluripotency-associated genes can be one or more of the genes selected from the group consisting of OCT4, SOX2, KLF4, Lin28, NANOG, and cMYC.

Performing a Biopsy or Aspirate of the Patient's Bone Marrow

In some embodiments, a biopsy or aspirate is a sample of tissue or fluid taken from the body. There are many different kinds of biopsies or aspirates. Nearly all of them involve using a sharp tool to remove a small amount of tissue. If the biopsy will be on the skin or other sensitive area, numbing medicine can be applied first. A biopsy or aspirate can be performed according to any of the known methods in the art. For example, in a bone marrow aspirate, a large needle is used to enter the pelvis bone to collect bone marrow.

Isolating a Mesenchymal Stem Cell

Mesenchymal stem cells can be isolated according to any method known in the art, such as from a patient's bone marrow or peripheral blood. For example, marrow aspirate can be collected into a syringe with heparin. Cells can be washed and centrifuged on a Percoll™ density gradient. Cells, such as blood cells, liver cells, interstitial cells, macrophages, mast cells, and thymocytes, can be separated using Percoll™. The cells can be cultured in Dulbecco's modified Eagle's medium (DMEM) (low glucose) containing 10% fetal bovine serum (FBS) (Pittinger M F, Mackay A M, Beck S C et al., Science 1999; 284:143-147).

Isolating a Hematopoietic Progenitor Cell from a Patient

A hematopoietic progenitor cell can be isolated from a patient by any method known in the art. CD34+ cells can be enriched, e.g., using CliniMACS® Cell Selection System (Miltenyi Biotec). CD34+ cells can be weakly stimulated, e.g., in serum-free medium (e.g., CellGrow SCGM media, CellGenix) with cytokines (e.g., SCF, rhTPO, rhFLT3), before genome editing.

Human Hematopoietic Stem and Progenitor Cells

In some embodiments, the genetically modified cells of the present disclosure are human hematopoietic stem and progenitor cells (hHSPCs). This stem cell lineage gives rise to all blood cell types, including erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells). Blood cells are produced by the proliferation and differentiation of a very small population of pluripotent hematopoietic stem cells (HSCs) that also have the ability to replenish themselves by self-renewal. During differentiation, the progeny of HSCs progress through various intermediate maturational stages, generating multi-potential and lineage-committed progenitor cells prior to reaching maturity. Bone marrow (BM) is the major site of hematopoiesis in humans and, under normal conditions, only small numbers of hematopoietic stem and progenitor cells (HSPCs) can be found in the peripheral blood (PB). Treatment with cytokines (in particular granulocyte colony-stimulating factor; G-CSF), some myelosuppressive drugs used in cancer treatment, and compounds that disrupt the interaction between hematopoietic and BM stromal cells can rapidly mobilize large numbers of stem and progenitors into the circulation.

In some embodiments of the present disclosure, G-CSF is used in a subject to improve stem cell mobilization, while in other embodiments, plerixafor (Mozobil®) is used. In some embodiments, plerixafor is used in combination with G-CSF. Plerixafor is discussed in more detail below.

The best known marker of human HSPCs is the cell surface glycoprotein CD34. CD34 is routinely used to identify and isolate hHSPCs for use clinically in bone marrow transplantation. Thus, herein, the hHSPCs of the drug product are referred to as modified CD34+ hHSPCs.

Genetically Modified Cells

The term "genetically modified cell" refers to a cell that comprises at least one genetic modification introduced by genome editing (e.g., using the CRISPR/Cas9 system). In some ex vivo examples herein, the genetically modified cell can be genetically modified progenitor cell (e.g., CD34+ hHSPC). In some in vivo examples herein, the genetically modified cell can be a genetically modified hematopoietic progenitor cell (e.g., CD34+ hHSPC). A genetically modified cell comprising an exogenous genome-targeting nucleic acid and/or an exogenous nucleic acid encoding a genome-targeting nucleic acid is contemplated herein.

The term "control treated population" describes a population of cells that has been treated with identical media, viral induction, nucleic acid sequences, temperature, confluency, flask size, pH, etc., with the exception of the addition of the genome editing components. Any method known in the art can be used to measure the modulation or inactivation of the transcriptional control sequence of the BCL11A gene or protein expression or activity, for example Western Blot analysis of the of the transcriptional control sequence of the BCL11A gene protein or quantifying of the transcriptional control sequence of the BCL11A gene mRNA.

The term "isolated cell" refers to a cell that has been removed from an organism in which it was originally found, or a descendant of such a cell. Optionally, the cell can be cultured in vitro, e.g., under defined conditions or in the presence of other cells. Optionally, the cell can be later introduced into a second organism or re-introduced into the organism from which it (or the cell from which it is descended) was isolated.

The term "isolated population" with respect to an isolated population of cells refers to a population of cells that has been removed and separated from a mixed or heterogeneous population of cells. In some cases, the isolated population can be a substantially pure population of cells, as compared to the heterogeneous population from which the cells were isolated or enriched. In some cases, the isolated population can be an isolated population of human progenitor cells, e.g., a substantially pure population of human progenitor cells, as compared to a heterogeneous population of cells comprising human progenitor cells and cells from which the human progenitor cells were derived.

The term "substantially enhanced," with respect to a particular cell population, refers to a population of cells in which the occurrence of a particular type of cell is increased relative to pre-existing or reference levels, by at least 2-fold, at least 3-, at least 4-, at least 5-, at least 6-, at least 7-, at least 8-, at least 9, at least 10-, at least 20-, at least 50-, at least 100-, at least 400-, at least 1000-, at least 5000-, at least 20000-, at least 100000- or more fold depending, e.g., on the desired levels of such cells for ameliorating hemoglobinopathy.

The term "substantially enriched" with respect to a particular cell population, refers to a population of cells that is at least about 10%, about 20%, about 30%, about 40%, about 50%, about 60%, about 70% or more with respect to the cells making up a total cell population.

The term "substantially pure" with respect to a particular cell population, refers to a population of cells that is at least about 75%, at least about 85%, at least about 90%, or at least about 95% pure, with respect to the cells making up a total cell population. That is, the terms "substantially pure" or "essentially purified," with regard to a population of progenitor cells, refers to a population of cells that contain fewer than about 20%, about 15%, about 10%, about 9%, about 8%, about 7%, about 6%, about 5%, about 4%, about 3%, about 2%, about 1%, or less than 1%, of cells that are not progenitor cells as defined by the terms herein.

Differentiation of Genome-Edited iPSCs into Hematopoietic Progenitor Cells

In some embodiments, another step of the ex vivo methods of the present disclosure can comprise differentiating the genome-edited iPSCs into hematopoietic progenitor cells. The differentiating step can be performed according to any method known in the art.

Differentiation of Genome-Edited Mesenchymal Stem Cells into Hematopoietic Progenitor Cells In some embodiments, another step of the ex vivo methods of the present disclosure can comprise differentiating the genome-edited mesenchymal stem cells into hematopoietic progenitor cells. The differentiating step can be performed according to any method known in the art.

Drug Product

The drug product of the present disclosure is a cellular product that includes autologous $CD34^+$ hHSPCs modified by CRISPR-Cas9-mediated gene editing. The target of the CRISPR-Cas9 gene editing is the erythroid lineage-specific enhancer region of the BCL11A gene located on intron 2 between exons 2 and 3 on chromosome 2. The edits are created with a highly specific guide RNA, e.g., gRNAs comprising or consisting of SEQ ID NO: 1 or SEQ ID NO: 2, that targets a critical transcription factor binding site (GATA1) at the erythroid lineage-specific enhancer region, (identified as DNase I hypersensitive site +58, DHS+58) of the BCL11A gene (see, for example, WO2017/182881, incorporated herein by reference in its entirety). The gRNA-endonuclease RNP, e.g., gRNA-Cas9 RNP, in some embodiments, is delivered or introduced into cells of the present disclosure, e.g., $CD34^+$ hHSPCs, using viral or non-viral delivery mechanisms known in the art, e.g., electroporation. Following delivery into cells, the RNP introduces DSBs in DNA in a sequence-dependent manner. Repair of the DSB by NHEJ results in DNA indels, intended to disrupt GATA1 binding, thereby lowering BCL11A transcription, with concomitant increases in γ-globin and HbF levels. Since the gRNA-Cas9 RNP precisely targets the non-coding erythroid lineage-specific enhancer region of the BCL11A gene and not the BCL11A coding sequence itself, without being bound by theory, it is expected to modulate the levels of expression of the BCL11A gene and protein in cells solely of the erythroid lineage and not affect non-erythroid hematopoietic lineages.

The drug product, in some embodiments, is formulated in a serum-free (without serum or substantially free of serum) cryopreservation medium, such as CRYOSTOR® CS5 medium which contains 5% DMSO and Dextran 40. Other cryopreservation mediums and/or excipients may be used.

The modified CD34+ hHSPCs of the present disclosure, in some embodiments, exhibit an increase in γ/(γ+α)-globin mRNA ratios of 0.30±0.20 relative to unmodified CD34+ hHSPCs. In some embodiments, the modified CD34+ hHSPCs may exhibit an increase in γ/(γ+α)-globin mRNA ratio of 0.1 to 0.6 relative to unmodified CD34+ hHSPCs. In some embodiments, the modified CD34+ hHSPCs may exhibit an increase in γ/(γ+α)-globin mRNA ratio of 0.1, 0.2, 0.25, 0.3, 0.35, 0.4, 0.45, 0.5, 0.55, or 0.6 relative to unmodified CD34+ hHSPCs.

The modified CD34+ hHSPCs of the present disclosure, in some embodiments, exhibit an increase in γ/(γ+β)-globin mRNA ratios of 0.41±0.15 relative to unmodified CD34+ hHSPCs. In some embodiments, the modified CD34+ hHSPCs may exhibit an increase in γ/(γ+β)-globin mRNA ratio of 0.2 to 0.6 relative to unmodified CD34+ hHSPCs. In some embodiments, the modified CD34+ hHSPCs may exhibit an increase in γ/(γ+β)-globin mRNA ratio of 0.2, 0.25, 0.3, 0.35, 0.4, 0.45, 0.5, 0.55, or 0.6 relative to unmodified CD34+ hHSPCs.

In some embodiments, the modified CD34+ hHSPCs of the present disclosure exhibit a ratio of (γ+β)/α-globin mRNA that is at or above 0.4 (e.g., at or above 0.4, at or above 0.42, at or above 0.44, at or above 0.46, at or above 0.48, or at or above 0.5, such as above 0.4, at above 0.42, above 0.44, above 0.46, above 0.48, or above 0.5).

In some embodiments, the modified CD34+ hHSPCs exhibit a HbF mean percentage of HbF/(HbF+HbA) protein levels of 32%±9%. In some embodiments, the modified CD34+ hHSPCs exhibit a HbF mean percentage of HbF/(HbF+HbA) protein levels of 29%±11%. In some embodiments, the modified CD34+ hHSPCs exhibit a HbF mean percentage of HbF/(HbF+HbA) protein levels of 15%, 20%, 25%, 30%, 35%, 40%, 45%, or 50%.

In some embodiments, the modified CD34+ hHSPCs exhibit a mean allele editing frequency of 30% to 99%. In some embodiments, the modified CD34+ hHSPCs exhibit a mean allele editing frequency of 70% to 99%. In some embodiments, the modified CD34+ hHSPCs exhibit a mean allele editing frequency of 70% to 90%. In some embodiments, the modified CD34+ hHSPCs exhibit a mean allele editing frequency of 80%±4%. In some embodiments, the modified CD34+ hHSPCs exhibit a mean allele editing frequency of at least 30%, 35%, 40%, 45%, 50%, 55%, 60%, 65%, 70%, 75%, 80%, 85%, 90%, or 95%.

In some embodiments, at least 50% of the modified CD34+ hHSPCs maintain multi-lineage potential for at least sixteen weeks after administration of the modified CD34+ hHSPCs to a subject. In some embodiments, at least 30%, at least 35%, at least 40%, at least 45%, at least 50%, at least 55%, at least 60%, at least 65%, at least 70%, at least 75%, at least 80%, at least 85%, at least 85%, at least 90%, or at least 95% of the modified CD34+ hHSPCs maintain multi-lineage potential for at least sixteen (e.g., 16, 17, 18, 19, 20) weeks after administration of the modified CD34+ hHSPCs to a subject.

In some embodiments, the modified CD34+ hHSPCs exhibit an on-target indel rate of at least 80%. In some embodiments, the modified CD34+ hHSPCs exhibit an on-target indel rate of at least 40%, at least 45%, at least 50%, at least 55%, at least 60%, at least 65%, at least 70%, at least 75%, at least 80%, at least 85%, at least 90%, or at least 95%.

In some embodiments, the modified CD34+ hHSPCs exhibit an off-target indel rate of less than 5%, or less than 1%. In some embodiments, the modified CD34+ hHSPCs exhibit an off-target indel rate of less than 0.9%, less than 0.8%, 0.7%, 0.6%, 0.5%, 0.4%, 0.3%, 0.2%, or 0.1%.

Therapeutic Approach

Provided herein, in some aspects of the disclosure, are methods for treating a patient with a hemoglobinopathy. An aspect of such method is an ex vivo cell-based therapy using an iPSC. For example, a patient specific induced pluripotent stem cell (iPSC) can be created. Then, the chromosomal DNA of these iPS cells can be edited using the materials and methods described herein. Next, the genome-edited iPSCs can be differentiated into hematopoietic progenitor cells. Finally, the hematopoietic progenitor cells can be implanted into the patient.

Yet another aspect of such method is an ex vivo cell-based therapy using a mesenchymal stem cell. For example, a mesenchymal stem cell can be isolated from the patient, which can be isolated from the patient's bone marrow or peripheral blood. Next, the chromosomal DNA of these mesenchymal stem cells can be edited using the materials and methods described herein. Next, the genome-edited mesenchymal stem cells can be differentiated into hematopoietic progenitor cells. Finally, these hematopoietic progenitor cells can be implanted into the patient.

A further aspect of such method is an ex vivo cell-based therapy using a hematopoietic progenitor cell. For example, a hematopoietic progenitor cell can be isolated from the patient. Next, the chromosomal DNA of these cells can be edited using the materials and methods described herein. Finally, the genome-edited hematopoietic progenitor cells can be implanted into the patient.

One advantage of an ex vivo cell therapy approach is the ability to conduct a comprehensive analysis of the therapeutic prior to administration. Nuclease-based therapeutics can have some level of off-target effects. Performing gene correction ex vivo allows one to characterize the corrected cell population prior to implantation. The present disclosure includes sequencing part of or the entire genome of the corrected cells to ensure that the off-target effects, if any, can be in genomic locations associated with minimal risk to the patient. Furthermore, populations of specific cells, including clonal populations, can be isolated prior to implantation.

Another advantage of ex vivo cell therapy relates to genetic correction in iPSCs compared to other primary cell sources. iPSCs are prolific, making it easy to obtain the large number of cells that will be required for a cell-based therapy. Furthermore, iPSCs are an ideal cell type for performing clonal isolations. This allows screening for the correct genomic correction, without risking a decrease in viability. In contrast, other primary cells are viable for only a few passages and difficult to clonally expand. Thus, manipulation of iPSCs for the treatment of a hemoglobinopathy can be much easier, and can shorten the amount of time needed to make the desired genetic correction.

For ex vivo therapy, transplantation requires clearance of bone-marrow niches or the donor HSCs to engraft. Current methods rely on radiation and/or chemotherapy. Due to the limitations these impose, safer conditioning regiments have been and are being developed, such as immunodepletion of bone marrow cells by antibodies or antibody toxin conjugates directed against hematopoietic cell surface markers, for example CD117, c-kit and others. Success of HSC transplantation depends upon efficient homing to bone marrow, subsequent engraftment, and bone marrow repopulation. The level of gene-edited cells engrafted is important, as is the ability of the cells' multilineage engraftment.

Hematopoietic stem cells (HSCs) are an important target for ex vivo gene therapy as they provide a prolonged source of the corrected cells. Treated CD34+ cells would be returned to the patient.

Methods can also include an in vivo based therapy. Chromosomal DNA of the cells in the patient is edited using the materials and methods described herein. The cells can be bone marrow cells, hematopoietic progenitor cells, or CD34+ cells.

Although blood cells present an attractive target for ex vivo treatment and therapy, increased efficacy in delivery may permit direct in vivo delivery to the hematopoietic stem cells (HSCs) and/or other B and T cell progenitors, such as CD34+ cells. Ideally the targeting and editing would be directed to the relevant cells. Cleavage in other cells can also be prevented by the use of promoters only active in certain cells and or developmental stages. Additional promoters are inducible, and therefore can be temporally controlled if the nuclease is delivered as a plasmid. The amount of time that delivered RNA and protein remain in the cell can also be adjusted using treatments or domains added to change the half-life. In vivo treatment would eliminate a number of treatment steps, but a lower rate of delivery can require higher rates of editing. In vivo treatment can eliminate problems and losses from ex vivo treatment and engraftment.

An advantage of in vivo gene therapy can be the ease of therapeutic production and administration. The same therapeutic approach and therapy will have the potential to be used to treat more than one patient, for example a number of patients who share the same or similar genotype or allele. In contrast, ex vivo cell therapy typically requires using a patient's own cells, which are isolated, manipulated and returned to the same patient.

Also provided herein is a cellular method for editing the BCL11A gene in a cell by genome editing. For example, a cell can be isolated from a patient or animal. Then, the chromosomal DNA of the cell can be edited using the materials and methods described herein.

In some embodiments, the methods provided herein, regardless of whether a cellular or ex vivo or in vivo method, can involve one or a combination of the following: 1) modulating or inactivating the transcriptional control sequence of the BCL11A gene, by deletions that arise due to the NHEJ pathway, 2) modulating or inactivating the transcriptional control sequence of the BCL11A gene, by HDR, or 3) modulating or inactivating the transcriptional control sequence of the BCL11A gene, by deletion of at least a portion of the transcriptional control sequence and/or knocking-in wild-type BCL11A gene or cDNA comprising a modified transcriptional control sequence into the gene locus or at a heterologous location in the genome (such as a safe harbor site, such as AAVS1). Both the HDR and knock-in strategies may utilize a donor DNA template in Homology-Directed Repair (HDR). HDR in either strategy may be accomplished by making one or more single-stranded breaks (SSBs) or double-stranded breaks (DSBs) at specific sites in the genome by using one or more endonucleases.

For example, the NHEJ strategy can involve deleting at least a portion of the transcriptional control sequence of the BCL11A gene by inducing one single stranded break or double stranded break within or near the BCL11A gene or other DNA sequence that encodes a regulatory element of the BCL11A gene with one or more CRISPR endonucleases and a gRNA (e.g., crRNA+tracrRNA, or sgRNA), or two or more single stranded breaks or double stranded breaks within or near the BCL11A gene or other DNA sequence that encodes a regulatory element of the BCL11A gene with two or more CRISPR endonucleases and two or more sgRNAs. This approach can require development and optimization of sgRNAs for the transcriptional control sequence of the BCL11A gene.

For example, the HDR strategy can involve modulating or inactivating the transcriptional control sequence of the BCL11A gene by inducing one single stranded break or double stranded break within or near the BCL11A gene or other DNA sequence that encodes a regulatory element of the BCL11A gene with one or more CRISPR endonucleases and a gRNA (e.g., crRNA+tracrRNA, or sgRNA), or two or more single stranded breaks or double stranded breaks within or near the BCL11A gene or other DNA sequence that encodes a regulatory element of the BCL11A gene with one or more CRISPR endonucleases and two or more gRNAs, in the presence of a donor DNA template introduced exogenously to direct the cellular DSB response to Homology-Directed Repair (the donor DNA template can be a short single stranded oligonucleotide, a short double stranded oligonucleotide, a long single or double stranded DNA molecule). This approach can require development and optimization of gRNAs and donor DNA molecules comprising a wild-type BCL11A gene comprising a modified transcriptional control sequence.

For example, the knock-in strategy involves knocking-in a wild-type BCL11A gene or cDNA comprising a modified transcriptional control sequence into the locus of the BCL11A gene using a gRNA (e.g., crRNA+tracrRNA, or sgRNA) or a pair of gRNAs targeting upstream of or in the transcriptional control sequence of the BCL11A gene, or in a safe harbor site (such as AAVS1). The donor DNA can be single or double stranded DNA and comprises a wild-type BCL11A gene comprising a modified transcriptional control sequence. The advantages for the above strategies (deletion/modulation/inactivation and knock-in) are similar, including in principle both short and long term beneficial clinical and laboratory effects.

In addition to the editing options listed above, Cas9 or similar proteins can be used to target effector domains to the same target sites that can be identified for editing, or additional target sites within range of the effector domain. A range of chromatin modifying enzymes, methylases or demethylases can be used to alter expression of the target gene. These types of epigenetic regulation have some advantages, particularly as they are limited in possible off-target effects.

The regulation of transcription and translation implicates a number of different classes of sites that interact with cellular proteins or nucleotides. Often the DNA binding sites of transcription factors or other proteins can be targeted for mutation or deletion to study the role of the site, though they can also be targeted to change gene expression. Sites can be added through non-homologous end joining NHEJ or direct genome editing by homology directed repair (HDR). Increased use of genome sequencing, RNA expression and genome-wide studies of transcription factor binding have increased our ability to identify how the sites lead to developmental or temporal gene regulation. These control systems can be direct or can involve extensive cooperative regulation that can require the integration of activities from multiple enhancers. Transcription factors typically bind 6-12 bp-long degenerate DNA sequences. The low level of specificity provided by individual sites suggests that complex interactions and rules are involved in binding and the functional outcome. Binding sites with less degeneracy can provide simpler means of regulation. Artificial transcription factors can be designed to specify longer sequences that have less similar sequences in the genome and have lower potential for off-target cleavage. Any of these types of binding sites can be mutated, deleted or even created to enable changes in gene regulation or expression (Canver, M. C. et al., *Nature* (2015)). GATA transcription factors are a family of transcription factors characterized by their ability to bind to the GATA DNA binding sequence. A GATA binding sequence is located in the +58 DNA hypersensitive site (DHS) of the BCL11A gene. Another class of gene regulatory regions having these features is microRNA (miRNA) binding sites. miRNAs are non-coding RNAs that play key roles in post-transcriptional gene regulation. miRNA can regulate the expression of 30% of all mammalian protein-encoding genes. Specific and potent gene silencing by double stranded RNA (RNAi) was discovered, plus additional small noncoding RNA (Canver, M. C. et al., *Nature* (2015)). The largest class of noncoding RNAs important for gene silencing are miRNAs. In mammals, miRNAs are first transcribed as a long RNA transcripts, which can be separate transcriptional units, part of protein introns, or other transcripts. The long transcripts are called primary miRNA (pri-miRNA) that include imperfectly base-paired hairpin structures. These pri-miRNA can be cleaved into one or more shorter precursor miRNAs (pre-miRNAs) by Microprocessor, a protein complex in the nucleus, involving Drosha.

Pre-miRNAs are short stem loops ~70 nucleotides in length with a 2-nucleotide 3'-overhang that are exported, into the mature 19-25 nucleotide miRNA:miRNA* duplexes. The miRNA strand with lower base pairing stability (the guide strand) can be loaded onto the RNA-induced silencing complex (RISC). The passenger guide strand (marked with *), can be functional, but is usually degraded. The mature miRNA tethers RISC to partly complementary sequence motifs in target mRNAs predominantly found within the 3' untranslated regions (UTRs) and induces posttranscriptional gene silencing (Bartel, D. P. *Cell* 136, 215-233 (2009); Saj, A. & Lai, E. C. *Curr Opin Genet Dev* 21, 504-510 (2011)). miRNAs can be important in development, differentiation, cell cycle and growth control, and in virtually all biological pathways in mammals and other multicellular organisms. miRNAs can also be involved in cell cycle control, apoptosis and stem cell differentiation, hematopoiesis, hypoxia, muscle development, neurogenesis, insulin secretion, cholesterol metabolism, aging, viral replication and immune responses.

A single miRNA can target hundreds of different mRNA transcripts, while an individual transcript can be targeted by many different miRNAs. More than 28645 microRNAs have been annotated in the latest release of miRBase (v.21). Some miRNAs can be encoded by multiple loci, some of which can be expressed from tandemly co-transcribed clusters. The features allow for complex regulatory networks with multiple pathways and feedback controls. miRNAs can be integral parts of these feedback and regulatory circuits and can help regulate gene expression by keeping protein production within limits (Herranz, H. & Cohen, S. M. *Genes Dev* 24, 1339-1344 (2010); Posadas, D. M. & Carthew, R. W. *Curr Opin Genet Dev* 27, 1-6 (2014)).

miRNA can also be important in a large number of human diseases that are associated with abnormal miRNA expression. This association underscores the importance of the miRNA regulatory pathway. Recent miRNA deletion studies have linked miRNA with regulation of the immune responses (Stern-Ginossar, N. et al., *Science* 317, 376-381 (2007)). miRNA also have a strong link to cancer and can play a role in different types of cancer. miRNAs have been found to be downregulated in a number of tumors. miRNA can be important in the regulation of key cancer-related pathways, such as cell cycle control and the DNA damage response, and can therefore be used in diagnosis and can be targeted clinically. MicroRNAs can delicately regulate the balance of angiogenesis, such that experiments depleting all microRNAs suppresses tumor angiogenesis (Chen, S. et al., *Genes Dev* 28, 1054-1067 (2014)).

As has been shown for protein coding genes, miRNA genes can also be subject to epigenetic changes occurring with cancer. Many miRNA loci can be associated with CpG islands increasing their opportunity for regulation by DNA methylation (Weber, B., Stresemann, C., Brueckner, B. & Lyko, F. *Cell Cycle* 6, 1001-1005 (2007)). The majority of studies have used treatment with chromatin remodeling drugs to reveal epigenetically silenced miRNAs.

In addition to their role in RNA silencing, miRNA can also activate translation (Posadas, D. M. & Carthew, R. W. *Curr Opin Genet Dev* 27, 1-6 (2014)). Knocking out these sites may lead to decreased expression of the targeted gene, while introducing these sites may increase expression.

Individual miRNA can be knocked out most effectively by mutating the seed sequence (bases 2-8 of the microRNA), which can be important for binding specificity. Cleavage in this region, followed by mis-repair by NHEJ can effectively abolish miRNA function by blocking binding to target sites. miRNA could also be inhibited by specific targeting of the special loop region adjacent to the palindromic sequence. Catalytically inactive Cas9 can also be used to inhibit shRNA expression (Zhao, Y. et al., *Sci Rep* 4, 3943 (2014)). In addition to targeting the miRNA, the binding sites can also be targeted and mutated to prevent the silencing by miRNA.

Implanting Cells into Patients

In some embodiments, another step of the ex vivo methods of the present disclosure can comprise implanting the cells into patients. This implanting step can be accomplished using any method of implantation known in the art. For example, the genetically modified cells can be injected directly in the patient's blood or otherwise administered to the patient. The genetically modified cells may be purified ex vivo using a selected marker.

Treatment Methods—Autologous Stem Cell Transplantation

In some embodiments, the treatments methods of the present disclosure include an autologous stem cell transplantation procedure. The term "autologous" means that the donor cells used for the procedure are from the subject (patient). Herein, CD34+ hHSPCs are obtained from a subject, modified using CRISPR-Cas9 gene editing, and administered to the same subject. Generally, an autologous stem cell transplantation procedure as provided herein includes: administration (e.g., injection) of a (at least one) mobilizing agent (e.g., plerixafor and/or G-CSF), which results in mobilization of the stem cells (stem cells are stimulated to move into the bloodstream from the bone marrow space); collection of mobilized stem cells from the blood using apheresis; modification of the stem cells using CRISPR-Cas9 gene editing (e.g., modification within intron 2 of the BCL11A gene); and delivery of the modified stem cells to the subject.

Red Blood Cell Enrichment

During what is referred to as the pre-mobilization period, subjects, e.g., subjects with SCD, in some embodiments, may undergo red blood cell (RBC) transfusions. For example RBC transfusions may begin 8 (±2) weeks before the planned start of mobilization and can continue until the subject begins busulfan conditioning. The goal of these RBC transfusions, in some embodiments, is to target hemoglobin S (HbS) level of <30% of total Hb while keeping total Hb concentration ≤11 g/dL. Thus, in some embodiments, the methods of the present disclosure comprise administering red blood cells to a subject, prior to stem cell mobilization or at any other point during the treatment, as needed.

Stem Cell Mobilization

Because only small numbers of HSPCs are found in the peripheral blood, various different agents may be used to disrupt the interaction between hematopoietic and bone marrow stromal cells to rapidly mobilize large numbers of stem and progenitors into the circulation. Non-limiting examples of such agents include cytokines (e.g., granulocyte colony-stimulating factor (G-CSF)), some myelosuppressive drugs used in cancer treatment, and other compounds that disrupt the interaction between hematopoietic and bone marrow stromal cells. In some embodiments, the agent is plerixafor (MOZOBIL®).

Plerixafor is an inhibitor of the CXCR4 chemokine receptor and blocks binding of its cognate ligand stromal cell derived factor-1 (SDF-1α). SDF-1α and CXCR4 are recognized to play a role in the trafficking and homing of hematopoietic stem cells (HSCs) to the marrow compartment. Plerixafor (for injection) (NDC Number 0024-5862-01) is provided as a 20 mg/mL solution in a single use vial. Each vial is filled to deliver a volume of 1.2 mL and contains 24 mg of drug and 5.9 mg sodium chloride dissolved in water for injection adjusted to a pH of 6.0-7.5 with hydrochloric acid and with sodium hydroxide, if required. The recommended dose of plerixafor is 0.24 mg/kg of actual body weight, administered by subcutaneous (SC) injection. Thus, in some embodiments, plerixafor is administered to a subject at a dose of 0.24 mg/kg of actual body weight, although more or less may be administered. For example, plerixafor may be administered at a dose of 0.05, 0.1, 0.15, 0.2, 0.25, 0.3, or 0.35 mg/kg. In some embodiments, plerixafor is administered at a dose of 0.2, 0.21, 0.22, 0.23, 0.24, 0.25, 0.26, 0.27, 0.28, 0.29 mg/kg.

In some embodiments, a subject undergoes stem cell mobilization with plerixafor only, and then peripheral blood mononuclear cells (PBMC) are collected by apheresis. For example, on Day 1, subjects receive plerixafor 7 (±2) hours before planned apheresis.

In some embodiments, granulocyte-colony stimulating factor (G-CSF) (e.g., 10 micrograms/kg) is administered prior to the first dose of plerixafor. For example, G-CSF may be administered daily for four days prior to the first dose of plerixafor and on each day prior to apheresis. G-CSF may be referred to as filgrastim (ZARXIO®) or lenograstim (GRANOCYTE®). Subjects may undergo apheresis for 2 or 3 consecutive days to collect CD34+ hHSPC. The targeted CD34+ cell collection is at least $15 \times 10^6$ CD34+ cells/kg, in some embodiments, for manufacturing of the drug product in order to achieve a minimum target dose of $3 \times 10^6$ CD34+ cells/kg. Additional cells (e.g., an additional $2 \times 10^6$ CD34+ cells/kg) can be collected, in some embodiments, as backup for rescue therapy in an event of non-engraftment with drug product.

If the first mobilization and apheresis cycle does not yield enough cells for both the minimum drug product and safety backup or if a subject cannot complete apheresis, additional mobilization and apheresis cycles may be used to collect additional cells. The additional mobilization cycle may be initiated, for example, at least 14 days after the first day of the prior mobilization cycle and, in some embodiments, no more than 60 days after the end of the prior cycle.

Stem Cell Collection

Once mobilization has reached an optimal level, the stem cells are collected, primarily through apheresis. Established thresholds for apheresis initiation may vary, but typically range from 5 to 20 (e.g., 5, 10, 15, or 20) CD34+ cells/microlitre. Although useful in estimating mobilization efficacy, peripheral blood CD34+ counts can be variable. In some embodiments, at least $15 \times 10^6$ CD34+ hHSPCs/kg are collected, e.g., by apheresis. In some embodiments, $1 \times 10^6$ to $1 \times 10^8$ CD34+ hHSPCs/kg are collected.

Myeloablative Conditioning

Myeloablative chemotherapy is usually followed by a bone marrow or stem cell transplant to rebuild the bone marrow.

During drug product manufacturing and before the planned start of myeloablative (e.g., busulfan) conditioning, in some embodiments, subjects, e.g., subjects with SCD, will continue to receive simple or exchange RBC transfusions with the goal of maintaining HbS level of <30% of total Hb while keeping total Hb concentration ≤11 g/dL. If the planned start of myeloablative conditioning is greater than four months after completion of mobilization, for example, the RBC transfusion regimen may be stopped, and hydroxyurea (HU) treatment may be restarted for those subjects who have been previously treated with HU. If RBC transfusion regimen is interrupted, subjects can begin RBC transfusions (simple or exchange), in some embodiments, 8 (±2) weeks before the planned start of myeloablative conditioning with the goal to maintain HbS level of <30% of total Hb while keeping total Hb concentration ≤11 g/dL, for example. In some embodiments, if the HbS level is >30% of total Hb within 7 (±3) days before the planned start of myeloablative conditioning, subjects can receive one exchange transfusion with the goal to ensure HbS level is <30% before start of myeloablative conditioning.

In some embodiments, the myeloablative conditioning includes the administration of busulfan (BUSULFEX®, MYLERAN®). Busulfan is an anti-cancer (antineoplastic or cytotoxic) chemotherapy drug classified as an alkylating agent, often used in conditioning regimens prior to autologous stem cell transplant. The starting dose of busulfan, in some embodiments, is 3.2 mg/kg daily to target an area under the curve (AUC) of 4500 to 5500 µM/min, e.g., 4000 µM/min. Other doses may be used. For example, a dose of busulfan may be 2, 2.5, 3, 3.5, or 4 mg/kg. In some embodiments, the dose of busulfan is 2.5, 2.6, 2.7, 2.8, 2.9, 3.0, 3.1, 3.2, 3.3, 3.4, or 3.5 mg/kg. In some embodiments, the busulfan is administered intravenously (IV), for example, once daily for four consecutive days. In other embodiments, busulfan may be administered as 0.8 mg/kg every 6 hours (q6 h) for 4 consecutive days. Other dosing regimens may be used. In some embodiments, the dose is adjusted based on pharmacokinetic level to achieve an area under the curve (AUC) of 4500 to 5500 µM/min. In some embodiments, the dose is adjusted based on pharmacokinetic level to achieve an AUC of 5000 µM/min.

Pharmaceutically Acceptable Carriers

The ex vivo methods of administering progenitor cells (e.g., CD34+ hHSPCs) to a subject contemplated herein can involve the use of therapeutic compositions comprising progenitor cells (e.g., CD34+ hHSPCs).

Therapeutic compositions can contain a physiologically tolerable carrier together with the cell composition, and optionally at least one additional bioactive agent as described herein, dissolved or dispersed therein as an active ingredient. In some cases, the therapeutic composition is not substantially immunogenic when administered to a mammal or human patient for therapeutic purposes, unless so desired.

In general, the progenitor cells described herein (e.g., CD34+ hHSPCs) can be administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the progenitor cells, as described herein, using routine experimentation.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerine, vegetable oils such as cottonseed oil, and water-oil emulsions. The amount of an active compound used in the cell compositions that is effective in the treatment of a particular disorder or condition can depend on the nature of the disorder or condition, and can be determined by standard clinical techniques.

Administration & Efficacy

The terms "administering," "introducing" and "transplanting" are used interchangeably in the context of the placement of cells, e.g., progenitor cells such as CD34+ hHSPCs, into a subject, by a method or route that results in at least partial localization of the introduced cells at a desired site, such as a site of injury or repair, such that a desired effect(s) is produced. The cells e.g., progenitor cells such as CD34+ hHSPCs, or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the patient, i.e., long-term engraftment. For example, in some aspects described herein, an effective amount of myogenic progenitor cells is administered via a systemic route of administration, such as an intraperitoneal or intravenous route.

The terms "individual", "subject," "host" and "patient" are used interchangeably herein and refer to any subject for whom diagnosis, treatment or therapy is desired. In some aspects, the subject is a mammal. In some aspects, the subject is a human being.

When provided prophylactically, progenitor cells described herein (e.g., CD34+ hHSPCs) can be administered to a subject in advance of any symptom of a hemoglobinopathy, e.g., prior to the development of fatigue, shortness of breath, jaundice, slow growth late puberty, joint, bone and chest pain, enlarged spleen and liver. Accordingly, the prophylactic administration of a hematopoietic progenitor cell population serves to prevent a hemoglobinopathy, such as B-thalassemia or Sickle Cell Disease.

When provided therapeutically, hematopoietic progenitor cells are provided at (or after) the onset of a symptom or indication of hemoglobinopathy, e.g., upon the onset of disease.

The hematopoietic progenitor cell population being administered according to the methods described herein can comprise allogeneic hematopoietic progenitor cells obtained from one or more donors. "Allogeneic" refers to a hematopoietic progenitor cell or biological samples comprising hematopoietic progenitor cells obtained from one or more different donors of the same species, where the genes at one or more loci are not identical. For example, a hematopoietic progenitor cell population being administered to a subject can be derived from one more unrelated donor subjects, or from one or more non-identical siblings. In some cases, syngeneic hematopoietic progenitor cell populations can be used, such as those obtained from genetically identical animals, or from identical twins. The hematopoietic progenitor cells can be autologous cells; that is, the hematopoietic progenitor cells are obtained or isolated from a subject and administered to the same subject, i.e., the donor and recipient are the same.

The term "effective amount" refers to the amount of a population of progenitor cells (e.g., CD34+ hHSPCs) or their progeny needed to prevent or alleviate at least one or more signs or symptoms of hemoglobinopathy, and relates to a sufficient amount of a composition to provide the desired effect, e.g., to treat a subject having hemoglobinopathy. The term "therapeutically effective amount" therefore refers to an amount of progenitor cells (e.g., CD34+ hHSPCs) or a composition comprising progenitor cells (e.g., CD34+ hHSPCs) that is sufficient to promote a particular effect when administered to a typical subject, such as one who has or is at risk for hemoglobinopathy. An effective amount would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate "effective amount" can be determined by one of ordinary skill in the art using routine experimentation.

For use in the various aspects described herein, an effective amount of progenitor cells (e.g., CD34+ hHSPCs) comprises at least $10^2$ progenitor cells, at least $5\times10^2$ progenitor cells, at least $10^3$ progenitor cells, at least $5\times10^3$ progenitor cells, at least $10^4$ progenitor cells, at least $5\times10^4$ progenitor cells, at least $10^5$ progenitor cells, at least $2\times10^5$ progenitor cells, at least $3\times10^5$ progenitor cells, at least $4\times10^5$ progenitor cells, at least $5\times10^5$ progenitor cells, at least $6\times10^5$ progenitor cells, at least $7\times10^5$ progenitor cells, at least $8\times10^5$ progenitor cells, at least $9\times10^5$ progenitor cells, at least $1\times10^6$ progenitor cells, at least $2\times10^6$ progenitor cells, at least $3\times10^6$ progenitor cells, at least $4\times10^6$ progenitor cells, at least $5\times10^6$ progenitor cells, at least $6\times10^6$ progenitor cells, at least $7\times10^6$ progenitor cells, at least $8\times10^6$ progenitor cells, at least $9\times10^6$ progenitor cells, or multiples thereof. The progenitor cells can be derived from one or more donors, or can be obtained from an autologous source. In some examples described herein, the progenitor cells can be expanded in culture prior to administration to a subject in need thereof.

"Administered" refers to the delivery of a progenitor cell (e.g., CD34+ hHSPC) composition into a subject by a method or route that results in at least partial localization of the cell composition at a desired site. A cell composition can be administered by any appropriate route that results in effective treatment in the subject, i.e. administration results in delivery to a desired location in the subject where at least a portion of the composition delivered, i.e. at least $1\times10^4$ cells are delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some examples, the route is intravenous. For the delivery of cells, administration by injection or infusion can be made.

The cells can be administered systemically. The phrases "systemic administration," "administered systemically", "peripheral administration" and "administered peripherally" refer to the administration of a population of progenitor cells (e.g. CD34+ hHSPCs) other than directly into a target site, tissue, or organ, such that it enters, instead, the subject's circulatory system and, thus, is subject to metabolism and other like processes.

The efficacy of a treatment comprising a composition for the treatment of hemoglobinopathies can be determined by the skilled clinician. However, a treatment is considered "effective treatment," if any one or all of the signs or symptoms of, as but one example, levels of functional BCL11A and functional HbF are altered in a beneficial manner (e.g., decreased by at least 10% for BCL11A and/or increased by at least 10% for HbF), or other clinically accepted symptoms or markers of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

The treatment according to the present disclosure can ameliorate one or more symptoms associated with hemoglobinopathies by decreasing the amount of functional BCL11A and/or increasing the amount of functional HbF in the individual. Early signs typically associated with hemoglobinopathies include for example, fatigue, shortness of breath, jaundice, slow growth late puberty, joint, bone and chest pain, enlarged spleen and liver.

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "unit dosage form" refers to physically discrete units suitable as unitary dosages for human subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in animals or humans, as disclosed in this specification, these being features of the present invention. Examples of suitable unit dosage forms in accord with this invention are vials, tablets, capsules, troches, suppositories, powder packets, wafers, cachets, ampules, segregated multiples of any of the foregoing, and other forms as herein described or generally known in the art. One or more such unit dosage forms of the gene edited cells can be comprised in an article of manufacture of present invention.

Drug Product Dosage and Route of Administration

Autologous transplantation for various indications typically uses at least 2 to $2.5 \times 10^6$ CD34$^+$ cells/kg to support engraftment. To ensure engraftment in all subjects in the SCD study, a conservative minimum dose of $3 \times 10^6$ modified CD34$^+$ hHSPCs/kg may be used, which is 20% to 50% higher than the typical minimum dose for autologous transplantation. Without being bound by theory, infusion of a higher number of CD34$^+$ stem cells after myeloablation is associated with more rapid engraftment, durability, and efficacy of the treatment. In some embodiments, a lower or higher dose may be used. For example, a subject may be administered $2 \times 10^6$, $2.5 \times 10^6$, $3 \times 10^6$, $3.5 \times 10^6$, $4 \times 10^6$, $4.5 \times 10^6$, $5 \times 10^6$, $5.5 \times 10^6$, $6 \times 10^6$, $6.5 \times 10^6$, $7 \times 10^6$, $7.5 \times 10^6$, $8 \times 10^6$, $8.5 \times 10^6$, $9 \times 10^6$, $9.5 \times 10^6$, $1 \times 10^7$, $1.5 \times 10^7$, $2 \times 10^7$ modified CD34$^+$ hHSPCs/kg may be administered. In some embodiments, $3 \times 10^7$, $4 \times 10^7$, $5 \times 10^7$, $6 \times 10^7$, $7 \times 10^7$, $8 \times 10^7$, $9 \times 10^7$, or $1 \times 10^8$ modified CD34$^+$ hHSPCs/kg may be administered.

In some embodiments, a single dose of the drug product is administered at least 48 hours (e.g., at least 48, 54, 60, 66, or 72 hours) and within 7 days (e.g., 1, 2, 3, 4, 5, 6, or 7 days) after the last busulfan dose. In some embodiments, the entire dose of the drug product is infused within approximately 20 minutes of thaw.

In some embodiments, a subject receives the drug product on Day 1 via infusion through a central venous catheter. Other routes (e.g., intravenous routes) of administration may be used.

In some embodiments, neutrophil (and/or platelet) engraftment occurs in the subject within 42 days after administration of the modified CD34+ hHSPCs. Engraftment, generally, is the process by which collected stem cells received during transplant start to grow and make new blood cells. Neutrophil engraftment, in some embodiments, is defined as the first day of three consecutive days where the neutrophil count (absolute neutrophil count) is 500 cells/mm3 ($0.5 \times 10^9$/L) or greater. Platelet engraftment, in some embodiments, is defined as 20,000/mm3 ($20 \times 10^9$/L) unsupported by a platelet transfusion. In some embodiments, neutrophil (and/or platelet) engraftment occurs in the subject within 20, 25, 30, 35, or 40 days after administration of the modified CD34+ hHSPCs. In some embodiments, neutrophil (and/or platelet) engraftment occurs in the subject more than 40 days after administration of the modified CD34+ hHSPCs.

In some embodiments, there is a reduction in the number of transfusions for subjects with β-thalassemia from baseline following drug product infusion. In some embodiments, there is a reduction in the number of transfusions relative to baseline. For example, in some embodiments, there is a 2-fold reduction in the number of transfusions for subjects with β-thalassemia relative to baseline. In some embodiments, there is a 2.5-fold, 3-fold, 3.5-fold, 4-fold, 4.5-fold, or 5-fold reduction in the number of transfusions for subjects with β-thalassemia relative to baseline. In some embodiments, there is a 2-fold to 5-fold, 3-fold-to 5-fold, or 4-fold to 5-fold reduction in the number of transfusions for subjects with β-thalassemia relative to baseline. In some embodiments, the reduction in the number of transfusions is calculated starting at the time of administration (treatment), at least three months (or three months) after administration, or at least six months (or six months) after administration of the modified CD34+ hHSPCs. In some embodiments, there is a reduction in the number of transfusions for at least 6 months (e.g., at least 6 months, at least 12 months, at least 18 months, or at least 24 months), starting at the time of administration, three months after administration, or six months after administration of the modified CD34+ hHSPCs.

In some embodiments, there is a change from baseline in the number of subjects with β-thalassemia achieving transfusion independence (subjects not receiving regular disease-related transfusions) for at least 6 months, at least 12 months, at least 18 months, or at least 24 months, starting at the time of administration, at least 3 months after administration, at least six months after administration, or at least nine months after administration, of the modified CD34+ hHSPCs. It should be understood that a subject with β-thalassemia may be considered to have achieved transfusion independence, even if one or more transfusion(s) is/are required in certain clinical settings unrelated to the treatment of a hemoglobinopathy, such as a blood transfusion in connection with a surgery or excessive bleeding.

A baseline value is the most recent non missing measurement (scheduled or unscheduled) collected during screening and before start of mobilization.

For the number of transfusion events for subjects with β-thalassemia, pre-treatment baseline is defined as the number of transfusions during the 2 years prior to enrollment. Baseline can be calculated using records of all transfusion events during the 2 years before treatment. Change (absolute change) from baseline can be calculated as Post baseline value−Baseline value. Relative change from baseline can be calculated and expressed in percentage as 100%×(Post baseline value−Baseline value)/Baseline value.

In some embodiments, the HbF level in a subject with SCD is at least 20% in the absence of treatment with hydroxyurea (HU). In some embodiments, the HbF level in the subject with SCD is at least 30%, at least 40%, or at least 50% in the absence of treatment with HU. In some embodiments, the HbF level in the subject with SCD, in the absence of hydroxyurea (HU), is at least 20% for at least three months starting at the time of administration of the modified CD34+ hHSPCs. In some embodiments, the HbF level in the subject with SCD, in the absence of HU, is at least 30%, at least 40%, or at least 50% for at least three, at least four, at least five, or at least six months starting at the time of administration of the modified CD34+ hHSPCs. In some embodiments, the HbF level in the subject with SCD, in the absence of HU, is at least 20% for at least three months starting three months after administration of the modified CD34+ hHSPCs. In some embodiments, the HbF level in the subject with SCD, in the absence of HU, is at least 30%, at least 40%, or at least 50% for at least three, at least four, at least five, or at least six months starting three months after administration of the modified CD34+ hHSPC. In some embodiments, the HbF level in the subject with SCD, in the absence of HU, is at least 20% for at least three months starting six months after administration of the modified CD34+ hHSPCs. In some embodiments, the HbF level in the subject with SCD, in the absence of HU, is at least 30%, at least 40%, or at least 50% for at least three, at least four, at least five, or at least six months starting six months after administration of the modified CD34+ hHSPC.

In some embodiments, there is a relative change in annualized rate of severe vaso-occlusive crises (VOC) for subjects with SCD from baseline. In some embodiments, there is a reduction in annualized rate of severe VOC for subjects with SCD from baseline by at least 10%, at least 15%, at least 20%, at least 25%, at least 30%, at least 35%, at least 40%, at least 45%, at least 50%, at least 55%, at least 60%, at least 65%, at least 70%, or at least 75%, starting six months after administration of the modified CD34+ hHSPCs. In some embodiments, there is an absence of VOC for at least 12 months (e.g., at least 18 months or at least 24 months), starting six months after administration of the modified CD34+ hHSPCs.

In some embodiments, there is a change from baseline in annualized duration of hospitalization for severe VOC for subjects with SCD, starting six months after administration of the modified CD34+ hHSPCs.

A baseline value is the most recent non missing measurement (scheduled or unscheduled) collected during screening and before start of mobilization. For number of severe VOC events: Pre-treatment baseline is defined as the average annual severe VOC events during the 2 years prior to enrollment. Baseline can be calculated using records of all severe VOC events during the 2 years before treatment. Change (absolute change) from baseline can be calculated as Post baseline value−Baseline value. Relative change from baseline can be calculated and expressed in percentage as 100%×(Post baseline value−Baseline value)/Baseline value.

In some embodiments, in the subject there is a change in patient reported outcomes (PROs) over time using at least one of the following assays selected from: Pain scale (11 point numerical rating scale [NRS]), EuroQol Quality of Life Scale (EQ 5D 5L), functional assessment of cancer therapy-bone marrow transplant (FACT-BMT), Patient-reported Outcome Measurement Information System (PROMIS)-Fatigue, PROMIS-Cognitive function, and Adult Sickle Cell Quality of Life Measurement System (ASCQ-Me).

Pain-Scale (11 point NRS): Numerical rating scale is a 1-dimensional measure of reporting intensity of pain in adults. The 11 point NRS is a segmented visual analogue scale (VAS) including numbers from 0 to 10, '0' representing no pain to '10' representing worst possible pain. Each respondent will select a whole number on the scale that reflects their pain intensity. The score of NRS ranges from 0 to 10 points, with higher values indicating a higher level of pain.

EQ-5D-5L: The EQ-5D-5L questionnaire assesses a subject's health status in a standardized way and consists of 2 parts: the EQ-5D descriptive system and the EQ VAS. The EQ-5D-5L descriptive system comprises the same 5 dimensions; mobility, self-care, usual activities, pain/discomfort, and anxiety/depression. Each dimension has 5 levels: no problems, slight problems, moderate problems, severe problems, and extreme problems. The respondent is asked to indicate his/her health state by ticking (or placing a cross) in the box against the most appropriate statement in each of the 5 dimensions. This decision results in a 1-digit number expressing the level selected for that dimension. The digits for 5 dimensions can be combined in a 5-digit number describing the subject's health state.

The EQ VAS records the subject's self-rated health on a 100-point VAS with endpoints labeled 'the best health you can imagine' and 'the worst health you can imagine.' This information can be used as a quantitative measure of health as judged by the individual respondents.

FACT-BMT: The FACT-BMT questionnaire is a validated self-report questionnaire that includes physical, social, family, emotional, and functional well-being. The FACT-BMT consists of the FACT-General (constitutes the core of all subscales) and treatment-specific concerns of bone marrow transplantation.

Each statement in the FACT-BMT has a 5 point Likert-type response scale ranging from 0 to 4 (0="not at all"; 1="a little bit"; 2="somewhat"; 3="quite a bit"; and 4="very much"). The subject is asked to circle or mark 1 number per line to indicate his/her response to the statement as it applies to the past 7 days. Questionnaires are then scored, and the higher the score, the better the QOL. This information can be used to provide a holistic assessment that identifies subject's needs, which may not be revealed by a standard clinical consultation.

PROMIS-Fatigue and -Cognitive Function: PROMIS item bank contains over 300 items of illness-related PROs. PROMIS-Fatigue 7a contains 7 items and evaluates self-reported symptoms such as feeling tired and extreme exhaustion, and the impact of these symptoms on daily activities and normal functioning. PROMIS-Cognitive function 8a contains 8 items pertaining to the ability to think, concentrate, etc. Both measures have a 7-day recall period ("in the past 7 days"). Each question has 5 levels: never, almost never, sometimes, often, and almost always. PROMIS measures are scored using T-score metric with a mean of 50 for reference population and SD of 10. Scores can be interpreted by considering the direction of scoring and the difference between the reported score and the mean of 50 in reference population (SD 10).

ASCQ-Me: ASCQ-Me comprises of measures to assess physical, mental and social health along with information on severity of disease. It includes the following domains: emotional impact, pain impact, pain episodes, sleep impact, social functioning impact, stiffness impact and SCD medical history checklist. Most dimensions have 5 levels: never, rarely, sometimes, often, and always or not at all, a little bit, somewhat, quite a bit, and very much. Questions on SCD medical history checklist are indicated by yes or no options and pain episode frequency and severity are indicated by frequency of events. ASCQ-Me domains are scored using T-score metric with mean of 50 for reference population and SD of 10. Scores can be interpreted by considering the direction of scoring and the difference between the reported score and the mean of 50 in reference population (SD 10).

In some embodiments, in the subject there is a change in hemolytic index as measured by principal component analysis of the following four markers of hemolysis over time: reticulocyte count, serum concentrations of aspartate transaminase, lactate dehydrogenase [LDH], and total bilirubin.

Pulmonary hypertension (PHTN) is a potentially life-threatening complication, detected by echocardiographic evidence of elevated tricuspid regurgitant velocity (TRV). This condition has been described in adults with sickle cell disease (SCD) and other hemolytic disorders; however, there is little information on the occurrence of this condition in pediatric patients. In some embodiments, in the subject there is a change (e.g., reduction by at least 10%, at least 20%, or at least 30%) in tricuspid regurgitant jet velocity (TRV) over time.

In some embodiments, in the subject there is an increase in the proportion of circulating erythrocytes expressing fetal hemoglobin (F-cells) over time. In some embodiments, in the subject there is an least 10% (e.g., at least 20% or at least 30%) increase in the proportion of circulating erythrocytes expressing fetal hemoglobin (F-cells) over time.

In some embodiments, in the subject there is a change (e.g., reduction) in inflammatory and endothelial activation markers over time. In some embodiments, in the subject there is a reduction by at least 10%, at least 20%, or at least 30% in inflammatory and endothelial activation markers over time.

In some embodiments, in the subject there is a change (e.g., an increase) in the proportion of alleles with the genetic modification present in peripheral blood leukocytes over time. In some embodiments, in the subject there is an at least 10% (e.g., at least 20%, at least 30%, at least 40%, at least 50%) increase in the proportion of alleles with the genetic modification present in peripheral blood leukocytes over time.

In some embodiments, in the subject there is a change (e.g., an increase) in the proportion of alleles with the genetic modification present in bone marrow cells over time. In some embodiments, in the subject there is an at least 10% (e.g., at least 20%, at least 30%, at least 40%, at least 50%) increase in the proportion of alleles with the genetic modification present in peripheral blood leukocytes over time.

The period of time during which the above endpoints are measured may range from 3 months to 5 years or longer. For example, "over time" may include 3 months, 6 months, 9 months, 12 months, 18 months, 24 months, 30 months, 36 months, 42 months, 48 months, 54 months, or 60 months.

Kits

The present disclosure provides kits for carrying out the methods described herein. A kit can include one or more of a genome-targeting nucleic acid, a polynucleotide encoding a genome-targeting nucleic acid, a site-directed polypeptide, a polynucleotide encoding a site-directed polypeptide, and/or any nucleic acid or proteinaceous molecule necessary to carry out the aspects of the methods described herein, or any combination thereof.

A kit can comprise: (1) a vector comprising a nucleotide sequence encoding a genome-targeting nucleic acid, (2) the site-directed polypeptide or a vector comprising a nucleotide sequence encoding the site-directed polypeptide, and (3) a reagent for reconstitution and/or dilution of the vector(s) and or polypeptide.

A kit can comprise: (1) a vector comprising (i) a nucleotide sequence encoding a genome-targeting nucleic acid, and (ii) a nucleotide sequence encoding the site-directed polypeptide; and (2) a reagent for reconstitution and/or dilution of the vector.

In any of the above kits, the kit can comprise a single-molecule guide genome-targeting nucleic acid (e.g., SEQ ID NO: 1 or 2). In any of the above kits, the kit can comprise a double-molecule genome-targeting nucleic acid. In any of the above kits, the kit can comprise two or more double-molecule guides or single-molecule guides. The kits can comprise a vector that encodes the nucleic acid targeting nucleic acid.

In any of the above kits, the kit can further comprise a polynucleotide to be inserted to effect the desired genetic modification.

Components of a kit can be in separate containers, or combined in a single container.

Any kit described above can further comprise one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. A kit can also comprise one or more components that can be used to facilitate or enhance the on-target binding or the cleavage of DNA by the endonuclease, or improve the specificity of targeting.

In addition to the above-mentioned components, a kit can further comprise instructions for using the components of the kit to practice the methods. The instructions for practicing the methods can be recorded on a suitable recording medium. For example, the instructions can be printed on a substrate, such as paper or plastic, etc. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this case is a kit that comprises a web address where the instructions can be viewed and/or from which the instructions can be downloaded. As with the instructions, this means for obtaining the instructions can be recorded on a suitable substrate.

EXAMPLES

Example 1. Nonclinical Studies

The following nonclinical efficacy and toxicology studies were conducted.

Briefly, in pre-clinical studies investigating the drug product (CTX001), CRISPR-Cas9 gene editing at BCL11A gene erythroid enhancer of healthy donor CD34+ cells led to an increase in γ-globin mRNA (mean γ/α-globin ratios of 0.30 (standard deviation [SD]±0.20) and γ/(γ+β)-globin ratios of 0.41 (SD±0.15)) and HbF (mean percentage of HbF/(HbF+HbA) protein levels of 32% (SD±9%)). The mean allele editing frequency was 80% (SD±4%) and uniform across subpopulation of CD34+ cells, including long-term hematopoietic stem cells (LT-HSC). The majority of editing was bi-allelic.

In mice xenotransplantation studies, there was no difference in engraftment chimerism between NOD SCID gamma (NSG) mice infused with the drug product or control (EGFP) edited CD34+ hHSPCs at 16 weeks post-transplantation (FIG. 1). The average frequency of edited alleles present in the bone marrow samples at 16 weeks was 91% (SD±15%). Furthermore, the engrafted cells were able to maintain their multi-lineage potential (FIG. 1).

To further address the most relevant potential risks associated with the drug product, pre-clinical studies evaluating the safety of the drug product were also performed. In the non-clinical genotoxicity and toxicology assessment of the drug product, the on-target and potential off-target editing was extensively and systematically evaluated using multiple well-established methods. The drug product demonstrated high rate of on-target insertions and deletions (approximately 88%) and no off-target editing at detectable levels compared to unedited healthy donor cells. Karyotyping analysis did not identify any chromosomal translocations or other detectable abnormalities. Further, a tumorigenicity study did not reveal any neoplastic or myeloproliferative lesions in the mice receiving the drug product.

β-Thalassemia Patient Samples

The high frequency of allele editing was replicated in β-thalassemia patient (two $\beta^+/\beta^+$, one $\beta^0/\beta^0$) samples and resulted in γ/α-globin mRNA ratios of 0.42 and 0.58 in $\beta^+/\beta^+$ and 0.41 in $\beta^0/\beta^0$ after gRNA-RNP editing and elevated HbF/(HbF+HbA) protein levels of 73% and 79% in $\beta^+/\beta^+$ and 92% in $\beta^0/\beta^0$ in gRNA-RNP-treated compared to 24 and 50% in $\beta^+/\beta^+$ and 68% in $\beta^0/\beta^0$ in untreated controls. Levels were also measured in a further β-thalassemia patient ($\beta^+/\beta^0$) sample. The γ/α-globin mRNA ratio was 0.42 after gRNA-RNP editing and the HbF/(HbF+HbA) protein level was 81% after gRNA-RNP editing compared to a γ/α-globin mRNA ratio of 0.18 in untreated control and a HbF/(HbF+HbA) protein level of 61% in untreated control. The resultant increase in γ-globin mRNA and HbF levels with gRNA-RNP editing is clinically meaningful when compared to levels seen in historical examples of patients with HPFH.

Figure 2:
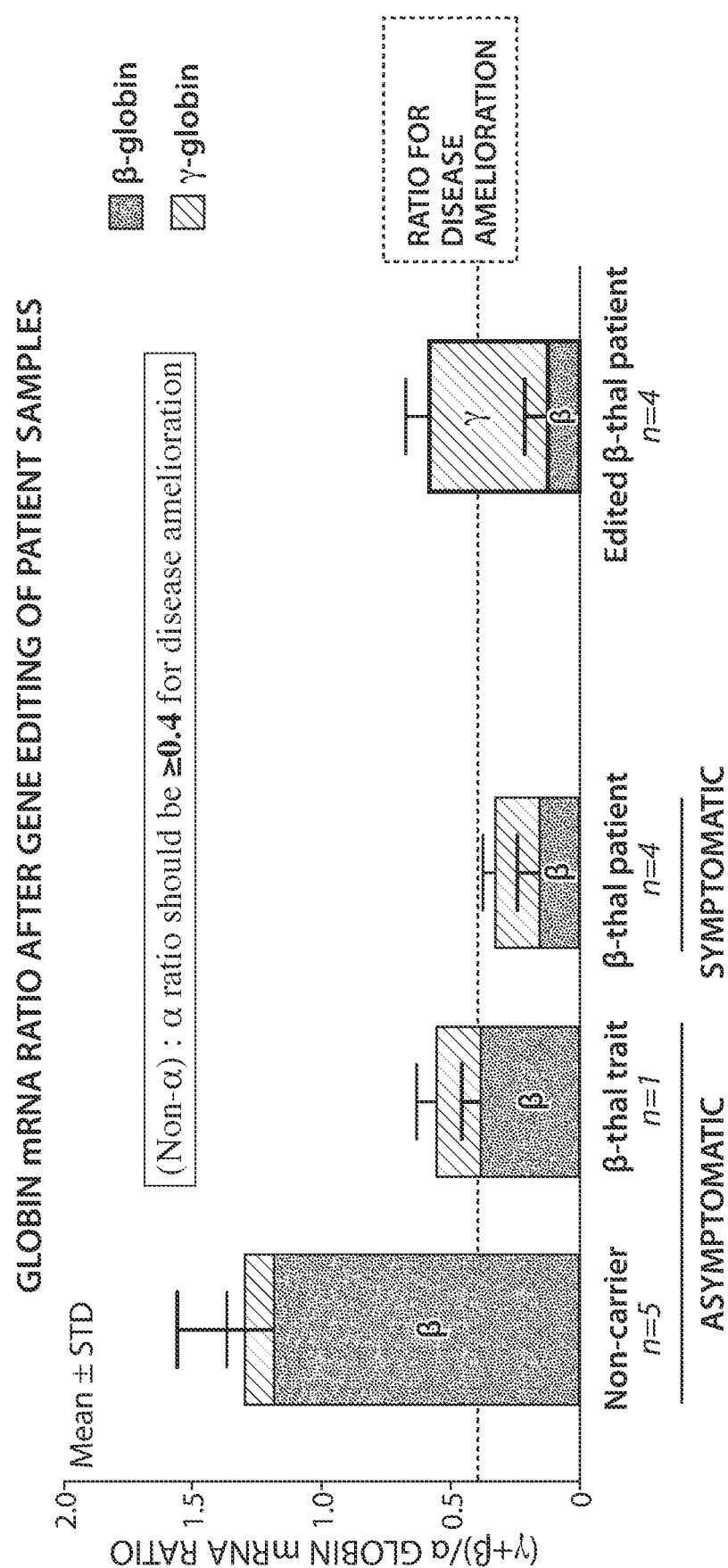
FIG. 2 is a graph showing the globin mRNA ratio after gene editing of β-thalassemia patient samples.
Figure 3:
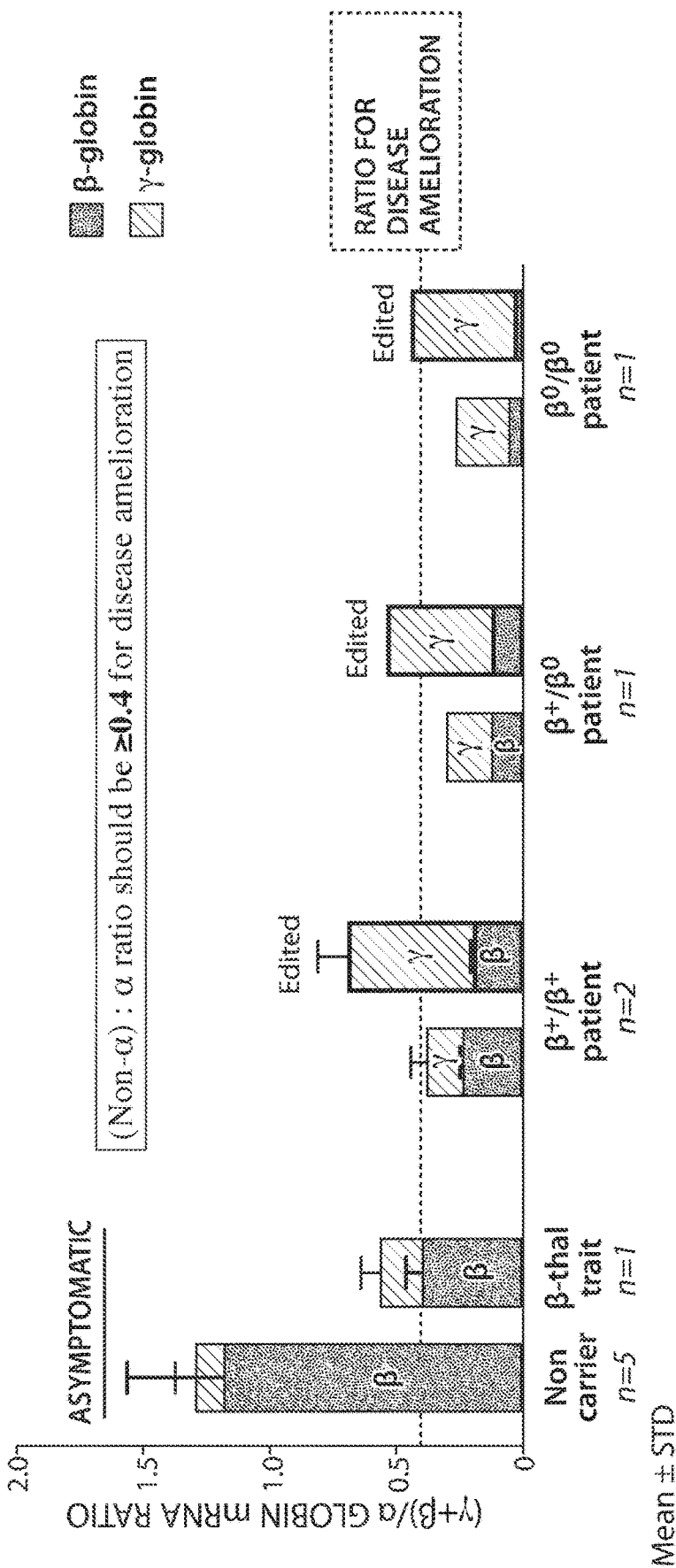
FIG. 3 is a graph showing the globin mRNA ratio after gene editing of β-thalassemia patient samples with the data separated by genotype.

The (γ+β)/α-globin mRNA ratio was also assessed in gRNA-RNP edited β-thalassemia patient (two $\beta^+/\beta^+$, one $\beta^0/\beta^0$ and one ($\beta^+/\beta^0$) samples and compared to untreated controls (FIG. 2 and FIG. 3). Without wishing to be bound by theory, it is expected that the threshold (γ+β)/α-globin mRNA ratio needed to obtain a clinical benefit is approximately 0.4 (see, e.g., Giampaolo et al. Heterocellular hereditary persistence of fetal hemoglobin (HPFH). Molecular mechanisms of abnormal gamma-gene expression in association with beta thalassemia and linkage relationship with the beta-globin gene cluster. Hum Genet. 1984; 66(2-3):151-156 and Marinucci et al. beta Thalassemia associated with increased HBF production. Evidence for the existence of a heterocellular hereditary persistence of fetal hemoglobin (HPFH) determinant linked to beta thalassemia in a southern Italian population. Hemoglobin. 1981; 5(1):1-). The edited β-thalassemia patient samples had a (γ+β)/α-globin mRNA ratio above 0.4 (FIG. 2 and FIG. 3), indicating that the combined increase in γ-globin and β-globin mRNA levels in the edited patient samples is clinically meaningful.

Sickle Cell Disease Patient Samples

Figure 4:
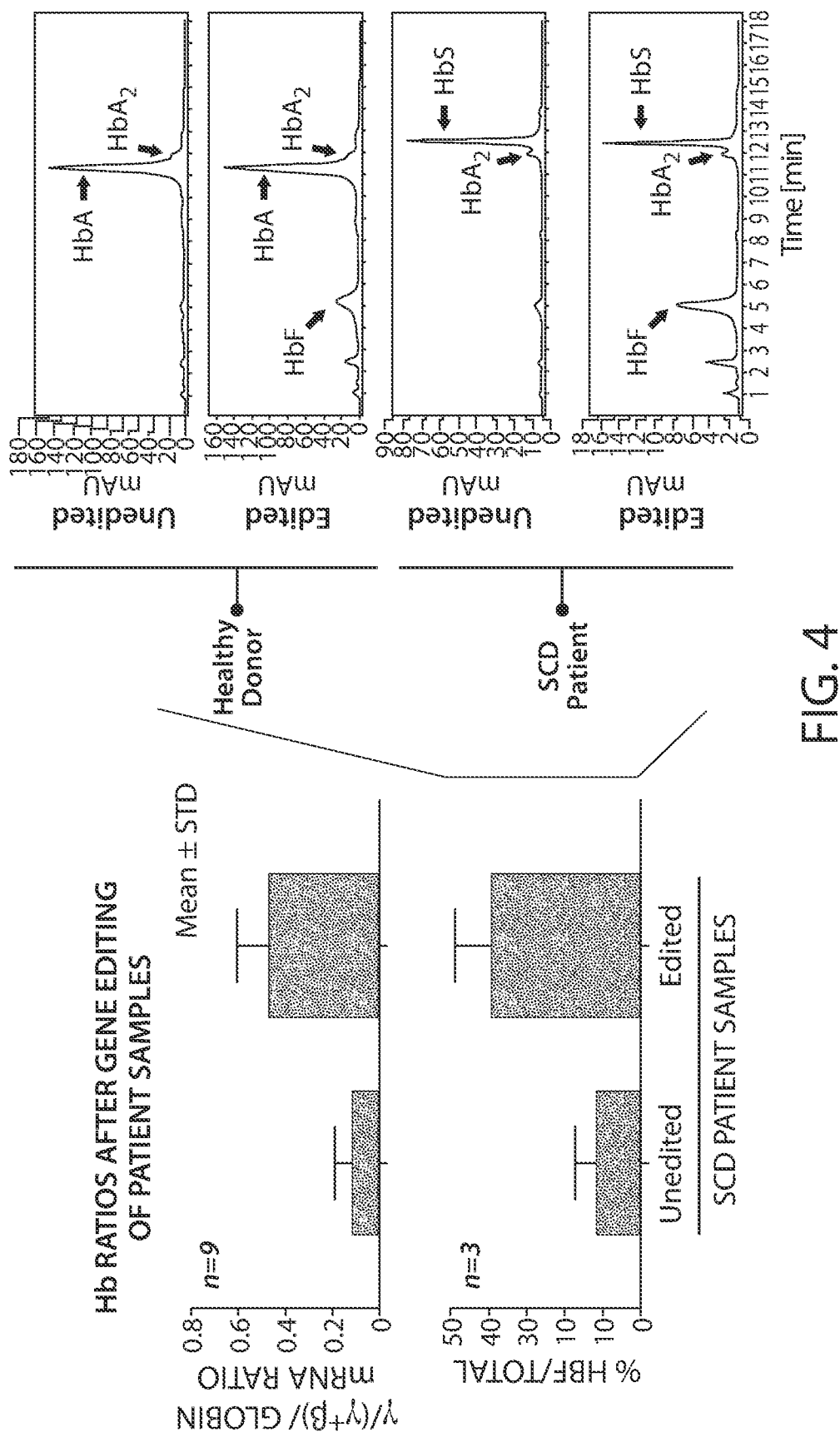
FIG. 4 is a series of graphs showing that HbF protein increases after editing of SCD patient samples.

The high frequency of allele editing was replicated in sickle cell disease patient samples and resulted in mean γ/(γ+β)-globin mRNA ratio of 0.53 (SD±0.085, n=9) and mean percentage HbF (HbF/(HbF+HbA)) protein levels of 40% (SD±9.2%, n=3) (FIG. 4).

Example 2. A Study to Evaluate the Safety and Efficacy of a Single Dose of Autologous CRISPR-Cas9 Modified CD34+ Human Hematopoietic Stem and Progenitor Cells in Subjects with Transfusion-Dependent β-Thalassemia A Phase 1/2 safety and efficacy study is conducted to evaluate the safety and efficacy of a single dose of autologous CRISPR-Cas9 modified CD34+ human hematopoietic stem and progenitor cells (hHSPCs) (the drug product) in subjects with transfusion-dependent β-thalassemia (primary objective). The effects of infusion of the drug product on disease-specific events and clinical status is assessed, and gene editing efficiency is quantified (secondary objectives). Further, the ability of biomarkers to characterize drug product effect and predict treatment outcomes is also assessed (exploratory objective). This study will include up to 12 subjects initially with possible expansion to 30 or more subjects enrolled in the study. The subjects enrolled in the study are 18 to 35 years of age (inclusive at time of informed consent) with documented non-$\beta^0/\beta^0$ transfusion-dependent β-thalassemia. The study may be extended to a pediatric population (e.g., younger than 18 years of age).

For the purposes of the study, transfusion-dependent β-thalassemia is defined by:

Documented homozygous β-thalassemia (with the exception of the ($\beta^0/\beta^0$ genotype) or compound heterozygous β-thalassemia including β-thalassemia/hemoglobin E (HbE).

At least 100 mL/kg/year or 10 units/year of packed RBC transfusions over a period of 2 years.

As a safety measure during the initial stages of the study, the first 2 subjects will be treated with the drug product in a staggered manner to ensure that there is successful engraftment of the first subject before treating the second subject in the study. The second subject will not undergo myeloablation until the first subject achieves neutrophil engraftment (absolute neutrophil count [ANC]≥500/µL for 3 consecutive days), the available engraftment and safety data have been reviewed by the data monitoring committee (DMC), and at least 30 days after infusion of the drug product to the first subject. Once the second subject has achieved neutrophil engraftment and has not had Grade ≥3 AEs other than those typically associated with busulfan conditioning or autologous transplant procedure, the remaining subjects can undergo conditioning and drug product infusion concurrently. In the event that the second subject infused with the drug product experiences Grade ≥3 AEs other than those typically associated with busulfan conditioning or autologous transplant procedure, a DMC meeting will be convened and data will be reviewed before the remaining subjects can undergo conditioning and drug product infusion. All steps that precede busulfan myeloablation such as consent, screening, and stem cell collection may proceed concurrently without staggering subjects.

The decision to expand the study to include a total of up to 30 subjects will be based on review of available safety and efficacy data by the Sponsor in consultation with the DMC and the Steering Committee (SC) after at least 6 subjects have received drug product infusion.

For each subject, the study will be conducted in 4 stages, which are described below. All subjects infused with the drug product will be asked to enroll into an additional long-term follow-up study.

Example Inclusion Criteria

Subjects must meet all the following inclusion criteria to be eligible for enrollment into the study:
1. Subject will sign and date an informed consent form (ICF).
2. Subjects 18 to 35 years of age, inclusive on the date of informed consent.
3. Diagnosis of transfusion-dependent β-thalassemia (TDT) as defined by:
   a. Documented homozygous β-thalassemia (with the exception of the $β^0/β^0$ genotype) or compound heterozygous β-thalassemia including β-thalassemia/hemoglobin E (HbE). Subjects can be enrolled based on historical data, but a confirmation of the genotype using the study central laboratory will be required before busulfan conditioning. The $β^0/β^0$ genotypes are defined using the HbVar Database.
   b. At least 100 mL/kg/year or 10 units/year of packed RBC transfusions over a period of 2 years prior to providing consent for the study
4. Karnofsky performance status of ≥80%.
5. Eligible for autologous stem cell transplant as per investigator's judgment.
6. Access to detailed medical records on packed RBC transfusions, including volume or units of packed RBCs and associated pre-transfusion Hb values, and in-patient hospitalizations, for at least the 2 years prior to consent.
7. Female subjects of childbearing potential (postmenarcheal, has an intact uterus and at least 1 ovary, and is less than 1 year postmenopausal) must agree to use acceptable method(s) of contraception from consent through at least 6 months after drug product infusion.
8. Male subjects must agree to use effective contraception from start of mobilization through at least 6 months after drug product infusion
9. Willing and able to comply with scheduled visits, treatment plan, laboratory tests, contraceptive guidelines, and other study procedures.
10. Willing to participate in an additional long-term follow-up study after completion of this study.

Example Exclusion Criteria

Subjects meeting any of the following criteria are not eligible for enrollment:
1. An available 10/10 human leukocyte antigen (HLA)-matched related donor.
2. Prior HSCT.
3. Subjects with associated α-thalassemia and >1 alpha chain deletion.
4. Subjects with a $β^0/β^0$ thalassemia genotype or sickle cell beta thalassemia variant
5. Clinically significant and active bacterial, viral, fungal, or parasitic infection as determined by the investigator.
6. White blood cell (WBC) count $<3\times10^9$/L or platelet count $<50\times10^9$/L, not related to hypersplenism per investigator judgment.
7. History of a significant bleeding disorder.
8. History of any illness or any clinical condition that, in the opinion of the investigator, might confound the results of the study or pose an additional risk to the subject. This may include, but is not limited to: history of relevant drug allergies; history of cardiovascular or central nervous system disease; history or presence of clinically significant pathology; history of mental disease, or history of familial cancer syndrome.
9. Any prior or current malignancy or myeloproliferative disorder or a significant immunodeficiency disorder.
10. Advanced liver disease, defined as
    a. Aspartate transaminase (AST), Alanine transaminase (ALT) >3× the upper limit of normal (ULN) or direct bilirubin value >2×ULN, or
    b. Baseline prothrombin time (PT) (international normalized ratio [INR]) >1.5×ULN, or
    c. History of cirrhosis or any evidence of bridging fibrosis, or active hepatitis on liver biopsy
11. A cardiac T2*<10 ms by MRI or left ventricular ejection fraction (LVEF) <45% by echocardiogram.
12. Baseline estimated glomerular filtration rate <60 mL/min/1.73 m$^2$.
13. Lung diffusing capacity for carbon monoxide (DLco) <50% of predicted value (corrected for hemoglobin and/or alveolar volume).
14. Prior treatment with gene therapy/editing product.
15. Intolerance, contraindication, or known sensitivity to plerixafor or busulfan. Prior anaphylactic reaction with excipients of the drug product (dimethylsulfoxide [DMSO], dextran).
16. Positive serology for human immunodeficiency virus-1 (HIV-1) or human immunodeficiency virus-2 (HIV-2), hepatitis B virus (HBV) (Hepatitis B core antibody [HBcAb] or nucleic acid testing [NAT]), or hepatitis C virus (HCV) (NAT). Positive serology for syphilis or any other infectious disease marker as required by local testing for cellular processing.
17. Participation in another clinical study with an investigational drug/product within 30 days of screening or fewer than 5 half-lives of the investigational agent, whichever is longer from screening.
18. Subjects who are not able to comply with the study procedures outlined in the protocol as judged by the investigator.
19. Pregnant or breastfeeding females.

The drug product includes autologous CD34+ hHSPCs modified with CRISPR-Cas9 at the erythroid lineage-specific enhancer of the BCL11A gene, administered by intravenous (IV) infusion.

This is a single-arm, open-label, multi-site, single-dose, Phase 1/2 study in subjects with transfusion-dependent β-thalassemia. The study will evaluate the safety and efficacy of a single dose of autologous CRISPR-Cas9 modified hHSPCs (the drug product) and will include up to 12 subjects, 18 to 35 years of age, inclusive. The study may be expanded to include a total of 30 or more subjects. The study may also include a pediatric population.

The overall process is consistent with procedures used for autologous HSCT in patients with malignant diseases, with a few exceptions that are described below. Therefore, the risk associated with the procedures in this study is not expected to be significantly different from the standard risks of these procedures.

Following mobilization, CD34$^+$ stem cells will be collected by apheresis with a combination of G-CSF products (e.g. filgrastim) and plerixafor. Collection of stem cells by apheresis rather than bone marrow harvest allows for easier isolation of CD34$^+$ cells as the process is less invasive for patients and does not require general anesthesia.

Busulfan alone will be used for conditioning. For allogeneic stem cell transplantation, busulfan is typically combined with cyclophosphamide or fludarabine, since this combination provides both myeloablation and immunosuppression. For autologous transplantation, as in the clinical study with the drug product, immunosuppression to prevent GvHD is not necessary and single agent busulfan will provide predominantly a myeloablative effect. Regimens using busulfan conditioning have been used in allogeneic transplantation of β-thalassemia and have resulted in successful engraftment, fewer treatment-related complications, and stable donor chimerism. In addition, other gene therapy studies have successfully used conditioning with busulfan alone in disease areas such as SCD, β-thalassemia, and severe combined immunodeficiency due to adenosine deaminase deficiency.

Since administration of the drug product is an autologous procedure, there is no need for a prophylactic treatment of GvHD.

The study will be conducted in 4 stages:

Stage 1: Screening and Pre-Mobilization Period

During this period, subjects who meet the inclusion criteria have the option to undergo fertility preservation via cryopreservation of oocyte or sperm.

Stage 2: Mobilization, Autologous CD34$^+$ Stem Cell Collection, Drug Product Manufacture and Disposition Each subject will undergo stem cell mobilization with a combination of G-CSF products (e.g. filgrastim) and plerixafor. Peripheral blood mononuclear cells (PBMC) will be collected by apheresis. Subjects will undergo apheresis for 2 or 3 consecutive days to collect CD34$^+$ hHSPC. The targeted CD34$^+$ cell collection is at least $15 \times 10^6$ CD34$^+$ cells/kg for manufacturing of the drug product in order to achieve a minimum target dose of $3 \times 10^6$ CD34$^+$ cells/kg. An additional $2 \times 10^6$ CD34$^+$ cells/kg will be collected as backup for rescue therapy in an event of non-engraftment with the drug product. If the first mobilization and apheresis cycle does not yield enough cells for both the minimum drug product and safety backup or if a subject cannot complete apheresis, up to 2 additional mobilization and apheresis cycles will be allowed to collect additional cells. The additional mobilization cycle will be initiated at least 14 days after the first day of the prior mobilization cycle and no more than 60 days after the end of the prior cycle.

Stage 3: Myeloablative Conditioning (Stage 3A) and Infusion of Drug Product (Day 1, Stage 3B)

Stage 3A—Myeloablative Conditioning:

After the drug product is received at the site and it has been confirmed that the backup cells have been stored and are available, the subject will be hospitalized and undergo myeloablative conditioning with busulfan. Busulfan will be administered intravenously (IV) daily at a starting dose of 3.2 mg/kg/day (based on weight collected 3-7 days prior to initiation of busulfan) for 4 consecutive days. Once-daily dosing is the preferred schedule; however, the busulfan dosing regimen may be adjusted to be given every 6 hours (Q6H) per the site's standard practice. The dose of busulfan will be adjusted based on the pharmacokinetics (PK) of the first busulfan dose to maintain appropriate levels for myeloablation. The average target area under the curve (AUC) for subjects receiving a starting dose of 3.2 mg/kg/day for 4 days is 5000 μM*min (range: 4500 to 5500 μM*min); equivalent to a target cumulative busulfan exposure of 90 mg×hr/L (range 80-100 mg×hr/L). The mean target AUC for subjects administered busulfan Q6H for 4 days is 1125 μM*min (range: 900 to 1350 μM*min).

Stage 3B—Drug Product Infusion:

Infusion of drug product will occur at a minimum of 48 hours following the completion of busulfan infusion and at a maximum of 7 days after the completion of busulfan infusion.

On Day 1, the entire dose (all vial[s]) of the drug product will be thawed and administered through a central venous catheter.

Stage 4: Follow-Up Through Engraftment and Up to 2 Years after Drug Product Infusion Stage 4A—Post-Infusion In-Hospital Follow-Up:

Subjects will be followed daily in the transplant unit and receive supportive care according to standard practices for subjects undergoing hematopoietic stem cell transplant (HSCT). Subjects will be monitored for AEs and engraftment. Packed RBC and platelet transfusions will be given to subjects per standard practices/investigator judgment for patients undergoing HSCT. Subjects will be discharged from the transplant unit upon neutrophil engraftment (defined as ANC ≥500/μL for 3 consecutive days) and stabilization of major medical issues as per local hospital guidelines and/or investigator judgment.

In the unlikely event that engraftment is not achieved within 42 days of drug product infusion, the subject will receive the backup CD34+ stem cells.

Stage 4B—Post-Engraftment Follow-Up:

Subjects will be followed for 24 months after drug product infusion with physical exams, laboratory and imaging assessments, and AE evaluations. Subjects will be allowed to restart iron chelation approximately one (1) month after drug product infusion according to the site's management guidelines and/or investigator judgment.

Following engraftment, transfusions of packed RBCs should be avoided for Hb ≥9 g/dL, unless medically indicated (e.g., symptomatic anemia or as a requirement for surgery). It is recommended that subjects should receive packed RBC transfusions for Hb <7.0 g/dL, while medical judgement is advised to transfuse for Hb levels of 7-9 g/dL based on a subject's clinical needs.

Infusion Procedures, Dose, and Administration

Autologous transplantation for various indications typically uses at least 2 to $2.5 \times 10^6$ CD34$^+$ cells/kg to support engraftment. To ensure engraftment in all subjects in the SCD study, a conservative minimum dose of $3 \times 10^6$ CD34$^+$ cells/kg was selected, which is 20% to 50% higher than the typical minimum dose for autologous transplantation. In principle, infusion of a higher number of CD34$^+$ stem cells after myeloablation is associated with more rapid engraftment, durability, and efficacy of the treatment.

The drug product will be formulated in CRYOSTOR® CS5 medium which contains 5% DMSO and Dextran 40. Histamine release associated with DMSO can result in symptoms such as; adverse effects including nausea, vomiting, diarrhea, flushing, fevers, chills, headache, dyspnea, rashes, bronchospasm, anaphylaxis, vasodilation and hypotension, and mental status changes. Given the risk of these AEs, subjects will be pre-medicated with an antihistamine (diphenhydramine hydrochloride) and an antipyretic (acetaminophen or paracetamol) before dosing with the drug product. These medications may be repeated every 3-4 hours as needed as per institutional guidelines and investigator judgment.

The single dose of the drug product will be given at least 48 hours and within 7 days after the last busulfan dose. The drug product vial(s) should be thawed just prior to the scheduled infusion as per local site SOPs. The entire dose of the drug product should be infused within 20 minutes of thaw. Detailed instructions for the thaw and infusion of cells are in the study reference manual. Hospital guidelines will be used to maintain chain of custody for the drug product from the stem cell laboratory to the subject. Before infusion, local procedures should be followed regarding the verification of subject identity and product details to ensure a match as well as integrity of the product.

Subjects will receive the drug product on Day 1 via infusion through a central venous catheter. All vial(s) containing the drug product should be infused.

All procedures involving the drug product should be performed using aseptic techniques by trained personnel according to the SOP at the clinical site.

In the unlikely event that drug product infusion does not occur within 7 days after the last dose of busulfan, subjects should receive the backup CD34+ stem cells.

Study Duration

The duration of Stage 1 will be approximately 1-3 months; Stage 2 approximately 2-3 months; Stage 3 approximately 1 month; Stage 4 approximately 2 years. Subjects will be followed on study for a total of approximately 2.5 years after signing the consent and for 2 years after drug product infusion. Additionally, all subjects infused with the drug product will be asked to enroll in a long-term follow-up study or registry following completion of or withdrawal/discontinuation from this study.

Prior Medications

All medication taken within 30 days of screening will be recorded. Retrospective information on RBC transfusions will be recorded from 24 months prior to date of consent study screening.

Venous Access

A central venous catheter will be used for administration of the conditioning regimen and infusion of the drug product. A central venous catheter may also be used for apheresis, exchange transfusions, and for clinical care of the subject following drug product infusion as per investigator judgment.

Transfusions

Prior to start of apheresis procedure and at least one month prior to planned initiation of busulfan conditioning, subjects should be transfused to achieve goal of Hb ≥11 g/dL. This is done to suppress ineffective erythropoiesis and allow for a more successful engraftment. During hospitalization for busulfan conditioning and drug product infusion subjects should be supported with packed RBC and platelet transfusions as per standard practices for patients undergoing HSCT.

During the 24-month follow-up period after infusion of the drug product, it is recommended that subjects receive packed RBCs for Hb ≤7 g/dL and for clinical symptoms requiring transfusion. Reason for all transfusions should be documented. Transfusions should be avoided for Hb ≥9 g/dL, unless considered clinically important (e.g., surgery). All blood products will be filtered and irradiated as per hospital guidelines.

Iron Chelation

Chelation must be discontinued at least 7 days prior to starting myeloablative conditioning with busulfan. Deferasirox is an exception which should be stopped at least 30 days before conditioning (due to potential drug-drug interaction). If deferasirox is stopped, a different chelator may be used for up to 7 days before busulfan conditioning.

Iron chelation with deferasirox, deferoxamine, or deferiprone should not be started until at least 1 month following CTX001 infusion to allow for stable hematopoietic recovery and avoid potential myelosuppressive effects. Subjects should be evaluated regularly to determine whether chelation is required. Chelators should be administered according to transfusion requirements and iron overload level when choosing the initial dose, escalation and interruption rules as per institutional guidelines.

Potential reasons for discontinuing iron chelation are:

Serum ferritin <1000 µg/L

LIC <7 mg/g

Transfusion independence and able to undergo phlebotomy as an alternative to iron chelation Phlebotomy may be used instead of chelation for subjects with Hb persistently ≥11 g/dL and who are transfusion independent.

Prohibited Medications

G-CSF should not be administered following CTX001 infusion unless discussed with and agreed to by the medical monitor. This is due to the hypothetical concern that early G-CSF administration will preferentially drive differentiation of the edited reinfused CD34+ cells into myeloid, not erythroid, lineage. Avoidance of G-CSF administration following CTX001 infusion may allow for full maturation of CD34+ cells in all lineages. Subjects should be monitored closely and if neutrophil engraftment has not occurred by Day+21 following CTX001 infusion, the investigator may contact the medical monitor to discuss the potential initiation of G-CSF.

Mobilization

Prior to the start of mobilization each subject will be examined by an apheresis-experienced physician and deemed to be appropriate to undergo mobilization and apheresis as per Table 1 and site's standard procedures. Examples of ineligibility include hemodynamic instability, positive infectious serologies, or active infection.

Mobilization will include of a combination of filgrastim and plerixafor. Filgrastim will be administered subcutaneously at a dose of 5 m/kg/dose every 12 hours for 5-6 days. Dose will be based on weight taken within 5 days of the first day of mobilization. Splenectomized subjects should receive a lower dose of G-CSF at 5 µg/kg every 24 hours for 5-6 days to prevent significant leukocytosis.

Plerixafor will be administered after the subject has received G-CSF for 4 days. Plerixafor is to be administered via subcutaneous injection; the recommended dose is 0.24 mg/kg administered approximately 5-7 hours prior to planned apheresis. Dose will also be based on the weight taken within 5 days prior to the first day of mobilization. See Table 1 for full dosing schedule.

Complete blood counts (CBCs) will be measured on the first, fourth, and fifth days of filgrastim for leukocytosis and the dose will be adjusted based on local practices in the presence of significant leukocytosis (e.g. $>70 \times 10^9$/L). $CD34^+$ cell count in peripheral blood will be performed in the morning(s) before the apheresis. Additional $CD34^+$ cell count and CBC may be performed as per site's standard operating procedures (SOPs).

TABLE 1

Mobilization and Apheresis Timing

| Drug | Mobilization | | | | Days of Apheresis | | |
|---|---|---|---|---|---|---|---|
| | Day 1 | Day 2 | Day 3 | Day 4 | Day 5 | Day 6 | Day 7 (if needed) |
| G-CSF administration (e.g., filgrastim) | X | X | X | X | X | X | |
| Plerixafor administration (7 [±2] hours before planned apheresis) | | | | X | X | X$^a$ | |
| CD34$^+$ stem cell apheresis for drug product and backup cells | | | | | X | X | X$^b$ |

$^a$Only subjects undergoing apheresis on Day 7 should receive plerixafor on Day 6 (or 7 ± 2 hours prior to planned apheresis on Day 7).
$^b$The third day of apheresis is reserved ONLY for collection of backup cells. No collection of cells for manufacturing should occur on that day.

Apheresis Procedure

PBMCs will be collected per clinical site SOPs for up to 3 days. The minimum goal for CD34+ cell collection for product manufacturing over the first and the second day of apheresis is 15×10$^6$ CD34+ cells/kg. Cells for manufacturing will not be collected on the third day of apheresis. These cells will be shipped to central manufacturing facility for drug product manufacture.

Backup cells with a goal of 2×10$^6$ CD34+ cells/kg will be collected on the third day of apheresis. Backup cells may also be collected on the second day of apheresis, but only after enough cells are available for shipment to the manufacturing facility. The backup cells are collected as a safety procedure in case of non-engraftment. The backup cells will be cryopreserved and stored at the treatment site. This occurs prior to proceeding to Stage 3 (busulfan conditioning).

If the first mobilization and apheresis cycle does not yield enough cells for both the minimum drug product and safety backup, a second mobilization cycle should occur 2-6 weeks later.

Conditioning: Busulfan Administration

Busulfan conditioning should start once the drug product is received at site and results of genotyping for thalassemia (alpha and HBB loci) have been confirmed. Busulfan will be administered IV daily at a starting dose of 3.2 mg/kg/day for 4 consecutive days (based on weight collected within 3-7 days prior to the first day of busulfan administration). Once-daily dosing is the preferred schedule, but the busulfan dose regimen may be adjusted to be given Q6H per site's standard practice.

The dose of busulfan will be adjusted based upon first dose busulfan PK in order to maintain appropriate levels for myeloablation. The average target AUC for subjects at a starting dose of 3.2 mg/kg/day for 4 days is 5000 μM*min (range: 4500 to 5500); equivalent to target cumulative busulfan exposure of 90 mg×hr/L [range 80100 mg×hr/L]). The AUC for subjects administered busulfan-Q6H for 4 days is 1125 μM*min (range: 900 to 1350).

A test dose of busulfan may be performed 3-7 days before beginning myeloablation to pre-determine busulfan dose may be performed. Defibrotide prophylaxis is allowed per investigator's discretion. During busulfan conditioning, seizure prophylaxis and other supportive measures should be instituted as per hospital guidelines.

Drug Product Infusion

The single dose of the drug product is given at least 48 hours and within 7 days after the last busulfan dose. Drug product vial(s) should be thawed just prior to the scheduled infusion utilizing local site SOPs and infused within 20 minutes of thaw.

Subjects will receive the drug product on Day 1 via infusion through a central venous catheter at a dose of ≥3.0×10$^6$ CD34+ cells/kg. All vial(s) containing the drug product should be infused.

All procedures involving the drug product should be performed using aseptic techniques by trained personnel according to the SOP at the clinical site.

Analysis of Primary Efficacy Endpoint

The drug product is a cellular product developed specifically to increase the production of HbF in erythrocytes. By measuring the levels of HbF in peripheral blood, we will directly assess the intended consequences of administration of the drug product.

The primary efficacy endpoint is "proportion of subjects achieving transfusion reduction for at least 6 months (TR6) during the 9 to 24 month time period after drug product infusion."

Analysis of Secondary Efficacy Endpoints

Proportion of subjects achieving transfusion independence for at least 6 months (TI6) starting from 3 months after drug product infusion.

Proportion of subjects achieving transfusion independence for at least 12 months (TR12) starting from 3 months after drug product infusion.

Proportion of subjects achieving transfusion reduction for at least 12 months (TI12) starting from 3 months after drug product infusion.

Proportion of alleles with intended genetic modification present in peripheral blood leukocytes over time. Intended genetic modifications are indels that modify the sequence of the erythrocyte-specific enhancer in intron 2 of BCL11A Proportion of alleles with intended genetic modification present in bone marrow cells over time Change in fetal hemoglobin concentration (pre-transfusion) over time Change in health-related quality of life (HRQoL) from baseline over time using EuroQol Questionnaire-5 dimensions-5 levels of severity (EQ-5D-5L)

Change in HRQoL from baseline over time using the Functional assessment of cancer therapy-bone marrow transplant questionnaire (FACT-BMT)

Change in parameters of iron overload, including:
  Liver iron concentration (LIC) and cardiac iron content (CIC) from baseline as assessed by T2* magnetic resonance imaging (MRI)
  Change in serum ferritin level from baseline over time
Proportion of subjects receiving iron chelation therapy over time Analysis of Exploratory Endpoints Change in proportion of circulating erythrocytes expressing fetal hemoglobin (F-cells) from baseline (pre-transfusion) over time Expression of α-globin and non-α-globin mRNA in circulating reticulocytes over time Change in erythropoietin (EPO) concentrations over time Change in hepcidin concentrations over time Assessment of erythropoiesis on bone marrow analysis compared with baseline over time Safety Analysis Proportion of subjects with engraftment. Engraftment is defined as absolute neutrophil count (ANC) ≥500/μL for three consecutive days. Engraftment failure is defined as any subject not achieving neutrophil engraftment by Day +42 following drug product infusion or if backup unmodified CD34+ cells are utilized. Separately, platelet engraftment will also be analyzed.

Time to engraftment

Frequency and severity of collected AEs from signing of informed consent through Month 24 visit as assessed by the National Cancer Institute (NCI) Common Terminology Criteria for Adverse Events (CTCAE) v4.03.

Incidence of transplant-related mortality (TRM) at 100 days and 1 year after drug product infusion. TRM is defined as death possibly related to the transplantation procedure.

All-cause mortality

Post-Drug Product Infusion Infection Prophylaxis and Surveillance

Following drug product infusion, subjects can undergo infectious surveillance and prophylaxis (bacterial, viral, fungal) as per local guidelines for HSCT and investigator judgment.

In the event that the subject develops sepsis or systemic bacteremia following drug product infusion, appropriate cultures and medical management will be initiated.

Patient Reported Outcomes

PRO assessments should be performed as the first assessment after obtaining informed consent, as well as be completed by subjects at the beginning of a study visit prior to any assessments.

Example 3. A Study to Evaluate the Safety and Efficacy of a Single Dose of Autologous CRISPR-Cas9 Modified CD34+ Human Hematopoietic Stem and Progenitor Cells in Subjects with Severe Sickle Cell Disease A Phase 1/2 safety and efficacy study is conducted to evaluate the safety and efficacy of a single dose of autologous CRISPR-Cas9 modified CD34+ human hematopoietic stem and progenitor cells (hHSPCs) (the drug product) in subjects with severe sickle cell disease (SCD) (primary objective). The effects of infusion of the drug product on disease-specific events and clinical status is assessed, and gene editing efficiency is quantified (secondary objectives). Further, the ability of biomarkers to characterize drug product effect and predict treatment outcomes is also assessed (exploratory objective). This study will include up to 12 subjects initially with possible expansion to 45 or more subjects are enrolled in the study. The subjects enrolled in the study are 18 to 35 years of age (inclusive at time of informed consent) with documented βS/βS genotype who have severe SCD. The study may be extended to a pediatric population (e.g., younger than 18 years of age).

Severe SCD is defined by the occurrence of at least 2 of the following events each year during the 2-year period before screening, while receiving appropriate supportive care (e.g. pain management plan, HU if indicated) as judged by the investigator:

Acute pain event that requires a visit to a medical facility and administration of pain medications (opioids or intravenous [IV] non-steroidal anti-inflammatory drugs [NSAIDs]) or RBC transfusions Acute chest syndrome, as indicated by the presence of a new pulmonary infiltrate associated with pneumonia-like symptoms, pain, or fever Priapism lasting >2 hours Splenic sequestration As a safety measure during the initial stages of the study, the first 2 subjects will be treated with the drug product in a staggered manner to ensure that there is successful engraftment of the first subject before treating the second subject in the study. The second subject will not undergo myeloablation until the first subject achieves neutrophil engraftment (absolute neutrophil count [ANC]≥500/μL for 3 consecutive days), the available engraftment and safety data have been reviewed by the data monitoring committee (DMC), and at least 30 days after infusion of the drug product to the first subject. Once the second subject has achieved neutrophil engraftment and has not had Grade ≥3 AEs other than those typically associated with busulfan conditioning or autologous transplant procedure, the remaining subjects can undergo conditioning and drug product infusion concurrently. In the event that the second subject infused with the drug product experiences Grade ≥3 AEs other than those typically associated with busulfan conditioning or autologous transplant procedure, a DMC meeting will be convened and data will be reviewed before the remaining subjects can undergo conditioning and drug product infusion. All steps that precede busulfan myeloablation such as consent, screening, and stem cell collection may proceed concurrently without staggering subjects.

The decision to expand the study to include a total of up to 45 subjects will be based on review of available safety and efficacy data by the Sponsor in consultation with the DMC and the Steering Committee (SC) after at least 6 subjects have received drug product infusion.

For each subject, the study will be conducted in 4 stages, which are described below. All subjects infused with the drug product will be asked to enroll into an additional long-term follow-up study.

Example Inclusion Criteria

Subjects must meet all the following inclusion criteria to be eligible for enrollment into the study:

11. Subject will sign and date an informed consent form (ICF).
12. Subjects 18 to 35 years of age, inclusive on the date of informed consent.
13. Documented βS/βS genotype. Subjects can be enrolled based on historical βS/βS genotype result, but confirmation of genotype is required before busulfan conditioning.
14. Subjects with severe SCD.
15. Karnofsky performance status of ≥80%.
16. Eligible for autologous stem cell transplant as per investigator's judgment.
17. Female subjects of childbearing potential (postmenarcheal, has an intact uterus and at least 1 ovary, and is less than 1 year postmenopausal) must agree to use acceptable method(s) of contraception from consent through at least 6 months after drug product infusion.
18. Male subjects must agree to use effective contraception from start of mobilization through at least 6 months after drug product infusion
19. Willing and able to comply with scheduled visits, treatment plan, laboratory tests, contraceptive guidelines, and other study procedures.
20. Willing to participate in an additional long-term follow-up study after completion of this study.

Example Exclusion Criteria

Subjects meeting any of the following criteria are not eligible for enrollment:
20. An available 10/10 human leukocyte antigen (HLA)-matched related donor.
21. Prior HSCT.
22. Clinically significant and active bacterial, viral, fungal, or parasitic infection as determined by the investigator.
23. White blood cell (WBC) count $<3\times10^9$/L or platelet count $<50\times10^9$/L, not related to hypersplenism per investigator judgment.
24. Treatment with regular RBC transfusions that, in the opinion of the investigator, cannot be interrupted after engraftment.
25. Subjects with history of alloimmunization to RBC antigens and for whom the investigator anticipates that there will be insufficient RBC units available for the duration of the study.
26. More than 10 unplanned hospitalizations or emergency department visits related to SCD in the 1 year before screening.
27. HbF level >15.0%, irrespective of concomitant treatment with HbF inducing treatments such as HU.
28. History of untreated Moyamoya disease or presence of Moyamoya disease at screening that in the opinion of the investigator puts the subjects at the risk of bleeding.
29. History of a significant bleeding disorder.
30. History of any illness or any clinical condition that, in the opinion of the investigator, might confound the results of the study or pose an additional risk to the subject. This may include, but is not limited to: history of relevant drug allergies; history of cardiovascular or central nervous system disease; history or presence of clinically significant pathology; history of mental disease, or history of familial cancer syndrome.
31. Any prior or current malignancy or myeloproliferative disorder or a significant immunodeficiency disorder.
32. Advanced liver disease, defined as
  a. Alanine transaminase (ALT) >3× the upper limit of normal (ULN) or direct bilirubin value >2×ULN, or
  b. Baseline prothrombin time (PT) (international normalized ratio [INR]) >1.5×ULN, or
  c. History of cirrhosis or any evidence of bridging fibrosis, or active hepatitis on liver biopsy
33. Baseline estimated glomerular filtration rate <60 mL/min/1.73 m$^2$.
34. Lung diffusing capacity for carbon monoxide (DLco) <50% of predicted value (corrected for hemoglobin and/or alveolar volume).
35. Left ventricular ejection fraction (LVEF) <45% by echocardiogram.
36. Prior treatment with gene therapy/editing product.
37. Intolerance, contraindication, or known sensitivity to plerixafor or busulfan. Prior anaphylactic reaction with excipients of the drug product (dimethylsulfoxide [DMSO], dextran).
38. Positive serology for human immunodeficiency virus-1 (HIV-1) or human immunodeficiency virus-2 (HIV-2), hepatitis B virus (HBV) (Hepatitis B core antibody [HBcAb] or nucleic acid testing [NAT]), or hepatitis C virus (HCV) (NAT). Positive serology for syphilis or any other infectious disease marker as required by local testing for cellular processing.
39. Participation in another clinical study with an investigational drug/product within 30 days of screening or fewer than 5 half-lives of the investigational agent, whichever is longer from screening.
40. Subjects who are not able to comply with the study procedures outlined in the protocol as judged by the investigator.
41. Pregnant or breastfeeding females.

The drug product includes autologous CD34+ hHSPCs modified with CRISPR-Cas9 at the erythroid lineage-specific enhancer of the BCL11A gene, administered by intravenous (IV) infusion.

This is a single-arm, open-label, multi-site, single-dose, Phase 1/2 study in subjects with severe SCD. The study will evaluate the safety and efficacy of a single dose of autologous CRISPR-Cas9 modified hHSPCs (the drug product) and will include up to 12 subjects, 18 to 35 years of age, inclusive. The study may be expanded to include a total of 45 or more subjects. The study may also include a pediatric population.

The overall process is consistent with procedures used for autologous HSCT in patients with malignant diseases, with a few exceptions that are described below. Therefore, the risk associated with the procedures in this study is not expected to be significantly different from the standard risks of these procedures.

Prophylactic RBC transfusions (simple or exchange) will be administered starting 8 (±2) weeks before mobilization through drug product infusion, to decrease the risk of VOC during mobilization and busulfan conditioning. The rationale for this transfusion guidance stems from evidence demonstrating that transfusion of non-sickle RBCs by simple or exchange techniques into patients with SCD can mitigate physiologic complications such as stroke[31], disease-related complications after surgical procedures[32], ACS[33], and VOCs.[34] Stem cell transplant protocols for patients with SCD often involve exchange transfusion to decrease HbS <30% prior to mobilization and conditioning.

Following mobilization, CD34$^+$ stem cells will be collected by apheresis with plerixafor alone. Collection of stem cells by apheresis rather than bone marrow harvest allows for easier isolation of CD34$^+$ cells as the process is less invasive for patients and does not require general anesthesia. The decision to use plerixafor alone instead of plerixafor in combination with granulocyte colony-stimulating factor (G-CSF), which is the standard regimen used for collection, comes from the fact that administration of G-CSF can induce severe VOCs in subjects with SCD, which can be fatal. Data from studies in healthy subjects and subjects with hemoglobinopathy show that plerixafor alone can effectively mobilize CD34$^+$ cells. These studies also show that CD34$^+$ cells collected using plerixafor alone in healthy subjects successfully engraft, when administered in the context of an allogeneic HSCT. In addition, a small study describing stem cell mobilization with plerixafor alone in subjects with severe SCD reports the collection of a median of 10.4×10$^6$ CD34$^+$ cells/kg (5.1 to 20.0) after a single apheresis. However, a non-severe pain crisis occurred in 3 of 7 subjects, despite administration of RBC transfusions in the preceding 2 months. Inability to successfully collect the target number of CD34$^+$ cells are among the stopping criteria for this study.

Busulfan alone will be used for conditioning. For allogeneic stem cell transplantation, busulfan is typically combined with cyclophosphamide or fludarabine, since this combination provides both myeloablation and immunosuppression. For autologous transplantation, as in the clinical study with the drug product, immunosuppression to prevent GvHD is not necessary and single agent busulfan will provide predominantly a myeloablative effect. Regimens using busulfan conditioning have been used in allogeneic transplantation of SCD and have resulted in successful engraftment, fewer treatment-related complications, and stable donor chimerism. In addition, other gene therapy studies have successfully used conditioning with busulfan alone in disease areas such as β-thalassemia, SCD, and severe combined immunodeficiency due to adenosine deaminase deficiency.

Since administration of the drug product is an autologous procedure, there is no need for a prophylactic treatment of GvHD.

The study will be conducted in 4 stages:

Stage 1: Screening and Pre-Mobilization Period

During this period, subjects who meet the inclusion criteria have the option to undergo fertility preservation via cryopreservation of oocyte or sperm. After eligibility is confirmed, subjects will begin RBC transfusions (simple or exchange) 8 (±2) weeks before the planned start of mobilization and will continue receiving these transfusions until they begin busulfan conditioning. The goal of these RBC transfusions is to target hemoglobin S (HbS) level of <30% of total Hb while keeping total Hb concentration ≤11 g/dL. Treatment with HU should be stopped at least 6 weeks before planned mobilization.

Stage 2: Mobilization, Autologous CD34$^+$ Stem Cell Collection, Drug Product Manufacture and Disposition Each subject will undergo stem cell mobilization with plerixafor only. Peripheral blood mononuclear cells (PBMC) will be collected by apheresis. On Day 1, subjects will receive plerixafor 7 (±2) hours before planned apheresis. Subjects will undergo apheresis for 2 or 3 consecutive days to collect CD34$^+$ hHSPC. The targeted CD34$^+$ cell collection is at least 15×10$^6$ CD34$^+$ cells/kg for manufacturing of the drug product in order to achieve a minimum target dose of 3×10$^6$ CD34$^+$ cells/kg. An additional 2×10$^6$ CD34$^+$ cells/kg will be collected as backup for rescue therapy in an event of non-engraftment with the drug product. If the first mobilization and apheresis cycle does not yield enough cells for both the minimum drug product and safety backup or if a subject cannot complete apheresis, up to 2 additional mobilization and apheresis cycles will be allowed to collect additional cells. The additional mobilization cycle will be initiated at least 14 days after the first day of the prior mobilization cycle and no more than 60 days after the end of the prior cycle.

Stage 3: Myeloablative Conditioning (Stage 3A) and Infusion of Drug Product (Day 1, Stage 3B)

Stage 3A—Myeloablative Conditioning:

During drug product manufacturing and before the planned start of busulfan conditioning, subjects will continue to receive simple or exchange RBC transfusions with the goal to maintain HbS level of <30% of total Hb while keeping total Hb concentration ≤11 g/dL.

If the planned start of busulfan conditioning is >4 months after completion of mobilization, the investigator may stop the RBC transfusion regimen and restart HU for those subjects who have been previously treated with HU. If RBC transfusion regimen is interrupted, subjects should begin RBC transfusions (simple or exchange) 8 (±2) weeks before the planned start of busulfan conditioning with the goal to maintain HbS level of <30% of total Hb while keeping total Hb concentration ≤11 g/dL. If HbS level is >30% of total Hb within 7 (±3) days before the planned start of busulfan conditioning, subjects will receive 1 exchange transfusion with the goal to ensure HbS level is <30% before start of busulfan conditioning.

After the drug product is received at the site and it has been confirmed that the backup cells remain available and in acceptable condition to be administered if needed, the subject will receive busulfan. The starting dose of busulfan will be 3.2 mg/kg administered IV once daily for 4 consecutive days. However, busulfan may be administered as 0.8 mg/kg every 6 hours (q6 h) for 4 consecutive days, per the site's standard practice.

Stage 3B—Drug Product Infusion:

Infusion of drug product will occur at a minimum of 48 hours following the completion of busulfan infusion and at a maximum of 7 days after the completion of busulfan infusion.

On Day 1, the entire dose (all vial[s]) of the drug product will be thawed and administered through a central venous catheter.

Stage 4: Follow-Up Through Engraftment and Up to 2 Years after Drug Product Infusion Stage 4A—Post-Infusion In-Hospital Follow-Up:

Subjects will be monitored daily in the transplant unit and receive supportive care according to standard practices for subjects undergoing hematopoietic stem cell transplant (HSCT).

Stage 4B—Post-Engraftment Follow-Up:

After discharge from the transplant unit subjects will be followed for approximately 2 years after drug product infusion.

The duration of Stage 1 will be approximately 2 to 4 months; Stage 2 approximately 2 to 4 months; Stage 3 approximately 1 month; Stage 4 approximately 2 years. Subjects will be followed on study for a total of approximately 2 years after drug product infusion. Additionally, all subjects infused with the drug product will be asked to enroll in a long-term follow-up study following completion or withdrawal/discontinuation.

The following assessments will be made: HbF levels, VOC events, RBC transfusions, alleles with intended genetic modification, and PROs for efficacy assessment; engraftment, TRM, clinical laboratory assessments, vital signs, height, weight, ECGs, and physical examinations (PEs) for safety assessment; and hemolysis laboratory assessment, TRV, inflammatory and endothelial activation markers, F cells distribution for exploratory assessment.

Infusion Procedures, Dose, and Administration

Autologous transplantation for various indications typically uses at least 2 to 2.5×10$^6$ CD34$^+$ cells/kg to support engraftment. To ensure engraftment in all subjects in the SCD study, a conservative minimum dose of 3×10$^6$ CD34$^+$ cells/kg was selected, which is 20% to 50% higher than the typical minimum dose for autologous transplantation. In principle, infusion of a higher number of CD34$^+$ stem cells after myeloablation is associated with more rapid engraftment, durability, and efficacy of the treatment.

The drug product will be formulated in CRYOSTOR® CS5 medium which contains 5% DMSO and Dextran 40. Histamine release associated with DMSO can result in symptoms such as; adverse effects including nausea, vomiting, diarrhea, flushing, fevers, chills, headache, dyspnea, rashes, bronchospasm, anaphylaxis, vasodilation and hypotension, and mental status changes. Given the risk of these AEs, subjects will be pre-medicated with an antihistamine (diphenhydramine hydrochloride) and an antipyretic (acetaminophen or paracetamol) before dosing with the drug product. These medications may be repeated every 3-4 hours as needed as per institutional guidelines and investigator judgment.

The single dose of the drug product will be given at least 48 hours and within 7 days after the last busulfan dose. The drug product vial(s) should be thawed just prior to the scheduled infusion as per local site SOPs. The entire dose of the drug product should be infused within 20 minutes of thaw. Detailed instructions for the thaw and infusion of cells are in the study reference manual. Hospital guidelines will be used to maintain chain of custody for the drug product from the stem cell laboratory to the subject. Before infusion, local procedures should be followed regarding the verification of subject identity and product details to ensure a match as well as integrity of the product.

Subjects will receive the drug product on Day 1 via infusion through a central venous catheter. All vial(s) containing the drug product should be infused.

All procedures involving the drug product must be performed using aseptic techniques by trained personnel according to the SOP at the clinical site.

In the unlikely event that drug product infusion does not occur within 7 days after the last dose of busulfan, subjects should receive the backup CD34+ stem cells.

Study Duration

Subjects will be followed on study for 2 years after drug product infusion. A 2-year follow up duration was considered adequate for characterization of clinical outcomes. Because the study will enroll subjects with at least 2 severe VOC events per year during the 2-year period before screening, a 2-year follow-up will allow meaningful assessment of the decrease in the annualized incidence of VOC.

Additionally, all subjects infused with the drug product will be asked to enroll in a long-term follow-up study for up to 15 years following completion or withdrawal/discontinuation. This is to ensure that any potential long term AEs related to the drug product are captured and to evaluate long term treatment outcomes as well as provide a longer follow up for efficacy.

Prior Medications

All medication taken within 30 days of screening will be recorded.

Retrospective information on RBC transfusions will be recorded from 24 months prior to date of consent study screening.

Venous Access

A central venous catheter will be used for administration of the conditioning regimen and infusion of the drug product. A central venous catheter may also be used for apheresis, exchange transfusions, and for clinical care of the subject following drug product infusion as per investigator judgment.

Prohibited Medications

HU: Treatment with hydroxyurea (HU) should be discontinued at least 6 weeks before planned start of mobilization. Subjects may be restarted on HU after mobilization and apheresis if deemed necessary by the investigator and if >4 months are planned between completion of mobilization and start of busulfan conditioning. If HU is restarted, treatment with HU should be discontinued once RBC transfusions are restarted before busulfan conditioning.

After drug product infusion, once engraftment is achieved, HU may be restarted if the subject experiences VOCs or other complications that are judged by the investigator to be related to SCD and warrant re-initiation of HU. If HU is restarted, it is recommended that HU be progressively tapered, if considered medically acceptable and if HbF is ≥20%.

L-Glutamine: Treatment with L-Glutamine should be discontinued after drug product infusion.

HbF inducing agent (other than HU): Treatment with any HbF inducing treatment should be discontinued after drug product infusion.

Mobilization

Decision on whether a central line is needed for mobilization will be made by the apheresis-experienced nurse or physician. Mobilization will be with plerixafor only. G-CSF should NOT be administered.

Subjects will receive plerixafor at a dose of 0.24 mg/kg via subcutaneous injection 7 (±2) hours before planned apheresis. Weight taken within 5 days before the first day of mobilization will be used for calculating the recommended dose. Refer to Table 2 for full dosing schedule.

TABLE 2

Mobilization and Apheresis Timing

| Drug | Mobilization and Apheresis | | |
|---|---|---|---|
| | Day 1 | Day 2 | Day 3 |
| Plerixafor administration (7 [±2] hours before planned apheresis) | X | X | $X^a$ |
| CD34$^+$ stem cell apheresis for drug product and backup cells | X | X | $X^b$ |

$^a$Only subjects undergoing apheresis on Day 3, should receive plerixafor on Day 3
$^b$The third day of apheresis is reserved ONLY for collection of backup cells. No collection of cells for manufacturing should occur on that day.

Apheresis Procedure

PBMC will be collected per clinical site standard operating procedures (SOPs) for up to 3 consecutive days. The targeted CD34$^+$ cell collection is at least 15×10$^6$ CD34$^+$ cells/kg for manufacturing of the drug product. A lower collection target may be later investigated if possible. An additional 2×10$^6$ CD34$^+$ cells/kg will be collected as backup for rescue therapy in an event of non-engraftment with the drug product. Collection of backup cells must occur prior to proceeding to Stage 3 (busulfan conditioning).

If the first mobilization and apheresis cycle does not yield enough cells for both the minimum drug product and safety backup, or if a subject cannot complete apheresis due to VOC(s), two additional mobilization and apheresis cycles will be allowed to collect additional cells.

The additional mobilization cycle should be initiated at least 14 days after the first day of the prior mobilization cycle and no more than 60 days after the end of the prior cycle. Based on the number of CD34$^+$ cells received at the manufacturing site and the manufactured drug product dose, the medical monitor will inform the clinical site if additional mobilization cycle will be necessary. The investigator should contact the medical monitor if the minimal cell dose for manufacturing or backup is not reached or if the subject requires an additional mobilization cycle.

Any AEs associated with apheresis procedure should be managed as per the site's standard guidelines.

Cells should be shipped at the end of the first and the second collection day. Cells collected for a backup dose will be cryopreserved and stored at the study site. Additional details and instructions on shipment and receipt are included in the study reference manual.

Conditioning: Busulfan Administration

Busulfan will be administered IV daily at a starting dose of 3.2 mg/kg/day for 4 consecutive days (based on weight collected within 3 to 7 days prior to the first day of busulfan administration). Once daily dosing is the preferred schedule, but the busulfan dose regimen may be adjusted to be given q6 h per site's standard practice. A test dose of busulfan may be performed 30 (±) 2 days before beginning myeloablation to pre-determine busulfan dose.

The dose of busulfan may be adjusted based on the PK of the first busulfan dose to maintain appropriate levels for myeloablation. The average target AUC for subjects at a starting dose of 3.2 mg/kg/day for 4 days is 5000 µM·min (range: 4500 to 5500); equivalent to target cumulative busulfan exposure of 90 mg·hr/L (range 80100 mg·hr/L). The AUC for subjects administered busulfan q6 h for 4 days is 1125 µM·min (range: 900 to 1350).

During busulfan conditioning, anti-seizure prophylaxis and other supportive measures should be instituted as per hospital guidelines.

Drug Product Infusion

The drug product will be supplied in infusion vial(s). All vial(s) containing the drug product should be infused. Further description is provided in the reference manual.

Analysis of Primary Efficacy Endpoint

The drug product is a cellular product developed specifically to increase the production of HbF in erythrocytes. By measuring the levels of HbF in peripheral blood, we will directly assess the intended consequences of administration of the drug product.

The primary efficacy endpoint is "HbF ≥20% for at least 3 months starting 6 months after drug product infusion, in the absence of treatment with HU." A subject will be considered to have met the primary efficacy endpoint if the subject has HbF levels of ≥20% for at least 3 months starting at 6 months after drug product infusion at the time of analysis in the absence of treatment with HU.

An HbF threshold of 20% was chosen for the primary endpoint based mainly on the reanalyses of CSSCD and MSH data. These analyses show an inverse relationship between relative risk of pain crises and HbF level, with a very low risk of pain crises for HbF levels of ≥20%. In particular, the regression model predicts a VOC risk reduction with HbF concentration of 20% (compared with an HbF concentration of 0%) of 87.3% (95% CI: 83.0%, 91.5%) based on CSSCD data and 81.5% (95% CI: 70.5%, 92.5%) based on MSH data.

A threshold of 20% is also supported by 2 observational studies that analyzed the relationship between HbF levels and SCD-related events in order to find a threshold that would guide treatment with HU. In a historical study conducted in 272 adults who were not receiving HU, higher HbF levels were associated with fewer complications, and the authors concluded that attainment of an HbF level of 20% would be needed to provide meaningful clinical benefit. In a more recent prospective study conducted in 230 children with SCD and treated with HU (Hydroxyurea Study of Long-Term Effects, HUSTLE), when HbF values were <20%, children had twice the odds of hospitalization for any reason, including vaso-occlusive pain and acute chest syndrome, and more than 4 times the odds of admission for fever. The authors concluded that their data suggest that the preferred dosing strategy is one that targets HbF ≥20%.

Analysis of Secondary Efficacy Endpoints

Relative change from baseline in annualized rate of severe VOC will be calculated for each subject and will be summarized.

Proportion of subjects with reduction in annualized rate of severe VOC from baseline by at least 50% after drug product infusion with the corresponding exact 95% CI will be provided.

Proportion of subjects with reduction in annualized rate of severe VOC from baseline by at least 65% after drug product infusion with the corresponding exact 95% CI will be provided.

Proportion of subjects achieving VOC event free with the corresponding exact 95% CI will be provided.

Relative change from baseline in annualized duration of hospitalization for severe VOC will be summarized.

Proportion of subjects achieving HbF ≥20% for at least 3 months, starting 3 months after drug product infusion at the time of analysis, with the exact 95% CI will be provided.

Proportion of subjects achieving HbF ≥20% for at least 3 months, starting at the time of drug product infusion at the time of analysis, with the exact 95% CI will be provided.

HbF and Hb concentrations will be summarized as a continuous variable over time.

Relative change in number of units of RBC transfused for SCD-related indications will be summarized.

Change in PROs will be summarized as a continuous variable over time.

Proportion of alleles with intended genetic modification present in peripheral blood leukocytes will be summarized as a continuous variable over time.

Proportion of alleles with intended genetic modification present in bone marrow cells will be summarized as a continuous variable over time.

Analysis of Exploratory Endpoints

Change in hemolytic index as measured by principal component analysis of 4 markers of hemolysis (reticulocyte count, serum concentrations of AST, LDH, and total bilirubin) will be summarized as a continuous variable over time.

Change in TRV will be summarized as a continuous variable over time.

Change in proportion of circulating erythrocytes expressing F-cells will be summarized as a continuous variable over time.

Change in inflammatory markers will be summarized as a continuous variable over time.

Change in endothelial activation markers will be summarized as a continuous variable over time.

Safety Analysis

AEs will be coded according to MedDRA.

Analysis based on Safety Analysis Set will include:

Proportion of subjects with neutrophil engraftment within 42 days after drug product infusion Time to neutrophil engraftment Time to platelet engraftment AEs, laboratory values, and vital signs from signing of informed consent through month 24 visit.

Incidence of TRM within 100 days and 1 year post drug product infusion. TRM defined as death possibly related to the transplantation procedure as assessed by the investigator.

All-cause mortality

The number and percentage of subjects with AEs and treatment-emergent AEs will be summarized by severity and seriousness in a tabular fashion according to the following time periods: ICF signed to start of mobilization, mobilization to start of busulfan conditioning, busulfan conditioning to start of drug product infusion, and drug product infusion through 24 months of post-infusion.

Time to neutrophil engraftment, defined as the first of 3 consecutive days with ANC ≥500/µL from transplantation, will be analyzed by the Kaplan-Meier method. Engraftment failure is defined as not achieving neutrophil engraftment by Day 42 post drug product infusion or receipt of backup stem cells. The number and percentage of subjects with engraftment failure will be summarized.

Time to platelet engraftment, defined as first 3 consecutive days with platelet ≥20,000/µL without a transfusion in the past 7 days will be assessed by the Kaplan-Meier method.

Laboratory abnormalities (values outside of normal ranges, and by Common Terminology Criteria for Adverse Events [CTCAE] grade), will also be tabulated.

The number and percentage of subjects with TRM within 100 days and 1 year post drug product infusion will be summarized, where TRM is defined as death at least possibly related to the transplantation procedure as assessed by the investigator. Relatedness between SAEs leading to death and transplantation will be as assessed by the investigators. If an SAE is assessed as being at least possibly related to the transplantation procedure, the death will be classified as transplant-related.

Statistical Analyses

The study will initially enroll up to 12 subjects to provide a preliminary evaluation of safety and efficacy of the drug product. The study may be expanded to include a total of up to 45 subjects. This expanded sample size will provide at least 90% power to rule out a response rate of 50% when the true response rate is 75% for HbF ≥20% for at least 3 months after drug product infusion at the time of analysis.

A group sequential testing procedure with 2 interim analyses (IAs) will be used in the expanded study to allow for early evaluation of overwhelming efficacy.

The proportion of subjects achieving HbF ≥20% for at least 3 months starting 6 months after drug product infusion at the time of analysis, with the exact 95% CI will be provided.

The key secondary efficacy endpoint, the relative change from baseline in annualized rate of severe VOC, will be summarized.

Continuous variables will be summarized using the following descriptive summary statistics: the number of subjects (n), mean, SD, median, minimum value (min), and maximum value (max).

Categorical variables will be summarized using counts and percentages. Percentages will be presented to 1 decimal place.

Uncertainty of estimates will be assessed by CIs. All subject data will be presented in the subject data listings; listings will display all subjects in the enrolled population, regardless of whether or not they received study drug. Longitudinal data will be presented by appropriate time intervals, such as monthly or quarterly depending on the nature of the data.

Baseline value, unless specified otherwise, will be defined as the most recent non missing measurement (scheduled or unscheduled) collected during screening and before start of mobilization.

For number of severe VOC events: Pre-treatment baseline is defined as the average annual severe VOC events during the 2 years prior to enrollment. Baseline will be calculated using records of all severe VOC events during the 2 years before signing of the ICF.

All severe VOC events that occur after drug product infusion until the end of study (Month 24) will be captured as post-drug product severe VOC events. All pre- and post-drug product infusion severe VOC events will be adjudicated by an EAC, and only severe VOC events related to the underlying SCD and not to an acute intercurrent event, such as acute bleeding or infection, will be included for evaluating the change from baseline in annualized rate of VOC.

Change (absolute change) from baseline will be calculated as Post baseline value−Baseline value.

Relative change from baseline will be calculated and expressed in percentage as 100%×(Post baseline value−Baseline value)/Baseline value.

Treatment emergent (TE) Period will include the time from drug product infusion to last study visit.

Post-Drug Product Infusion Infection Prophylaxis and Surveillance

Following drug product infusion, subjects can undergo infectious surveillance and prophylaxis (bacterial, viral, fungal) as per local guidelines for HSCT and investigator judgment.

In the event that the subject develops sepsis or systemic bacteremia following drug product infusion, appropriate cultures and medical management will be initiated.

Patient Reported Outcomes

PRO assessments should be performed as the first assessment after obtaining informed consent, as well as be completed by subjects at the beginning of a study visit prior to any assessments.

Note Regarding Illustrative Examples

While the present disclosure provides descriptions of various specific aspects for the purpose of illustrating various aspects of the present invention and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

Any patent, publication, or other disclosure material identified herein is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

The term "comprising" or "comprises" is used in reference to compositions, methods, and respective component(s) thereof, that are essential to the invention, yet open to the inclusion of unspecified elements, whether essential or not.

The term "consisting essentially of" refers to those elements required for a given aspect. The term permits the presence of additional elements that do not materially affect the basic and novel or functional characteristic(s) of that aspect of the invention.

The term "consisting of" refers to compositions, methods, and respective components thereof as described herein, which are exclusive of any element not recited in that description of the aspect.

The singular forms "a," "an," and "the" include plural references, unless the context clearly dictates otherwise.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with written description, sufficiency of description, and added matter requirements, including the requirements under 35 U.S.C. § 112(a) and Article 123(2) EPC. Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameter.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

---

What is claimed is:

1. A composition comprising a single dose of CD34+ human hematopoietic stem and progenitor cells (hHSPCs) that comprise a genetic modification within a +58 DNase I hypersensitive site (DHS) within the erythroid lineage-specific enhancer of a human B-cell lymphoma 11A (BCL11A) gene (modified CD34+ hHSPCs), wherein the single dose comprises an effective amount to result in an absence of vaso-occlusive crises (VOCs) for at least 12 months after administration of the hHSPCs, wherein the genetic modification is produced by delivering to the CD34+ hHSPCs a Cas9 endonuclease and a guide RNA (gRNA) comprising a nucleotide sequence of SEQ ID NO: 1 or SEQ ID NO: 2, and wherein the single dose comprises a minimum dose of $3 \times 10^6$ CD34+ hHSPCs per kg.

2. The composition of claim 1, further comprising a cryopreservation medium substantially free of serum, 5% dimethylsulfoxide (DMSO), and dextran-40.

3. The composition of claim 1, wherein (i) the modified CD34+ hHSPCs exhibit an increase in $\gamma/(\gamma+\alpha)$-globin mRNA ratios of 0.1 to 0.5 and/or wherein the modified CD34+ hHSPCs exhibit an increase in $\gamma/(\gamma+\beta)$-globin mRNA ratios of 0.2 to 0.6; (ii) the modified CD34+ hHSPCs comprise fetal hemoglobin (HbF) and adult hemoglobin (HbA) and exhibit a HbF mean percentage of HbF/(HbF+HbA) protein level of 15% to 50%; (iii) the modified CD34+ hHSPCs exhibit a mean allele editing frequency of 70% to 90%; (iv) at least 75% of the modified CD34+ hHSPCs maintain multi-lineage potential for at least sixteen weeks after administration of the modified CD34+ hHSPCs to a subject; (v) the modified CD34+ hHSPCs exhibit an on-target indel rate of at least 40%; and/or (vi) the modified CD34+ hHSPCs exhibit an off-target indel rate of less than 5%.

4. The composition of claim 1, wherein the genetic modification is produced by delivering to the CD34+ hHSPCs a *S. pyogenes* Cas9 endonuclease or a variant thereof comprising a N-terminal SV40 nuclear localization signal (NLS).

5. The composition of claim 1, wherein the genetic modification is produced by delivering to the CD34+ hHSPCs a Cas9 endonuclease and a guide RNA (gRNA) comprising the nucleotide sequence of SEQ ID NO: 1.

6. The composition of claim 1, wherein the genetic modification is produced by delivering to the CD34+ hHSPCs a Cas9 endonuclease and a guide RNA (gRNA) comprising the nucleotide sequence of SEQ ID NO: 2.

7. A method comprising administering to a subject having a hemoglobinopathy a single dose of CD34+ human hematopoietic stem and progenitor cells (hHSPCs) that comprise a genetic modification within a +58 DNase I hypersensitive site (DHS) within the erythroid lineage-specific enhancer of a human B-cell lymphoma 11A (BCL11A) gene (modified CD34+ hHSPCs), wherein the single dose comprises an effective amount to result in an absence of vaso-occlusive crises (VOCs) for at least 12 months after administration of the hHSPCs, wherein the genetic modification is produced by delivering to the CD34+ hHSPCs a Cas9 endonuclease and a guide RNA (gRNA) comprising a nucleotide sequence of SEQ ID NO: 1 or SEQ ID NO: 2, and wherein the single dose comprises a minimum dose of $3 \times 10^6$ CD34+ hHSPCs per kg.

8. The method of claim 7, further comprising administering red blood cells to the subject.

9. The method of claim 7, further comprising administering busulfan to the subject.

10. The method of claim 9, wherein the busulfan is administered prior to administration of the modified CD34+ hHSPCs.

11. The method of claim 10, wherein the dose is adjusted based on pharmacokinetic level to achieve an area under the curve (AUC) of 4500 to 5500 µM/min.

12. The method of claim 7, wherein
(i) the subject requires fewer blood transfusions within a two-year period of the time of administration of the modified CD34+ hHSPCs, or within a two-year period after the time of administration of the modified CD34+ hHSPCs, relative to a two-year period before the time of administration of the modified CD34+ hHSPCs;
(ii) the subject achieves transfusion reduction or transfusion independence for at least three months following administration of the modified CD34+ hHSPCs starting three months after administration of the modified CD34+ hHSPCs;
(iii) the subject achieves transfusion reduction or transfusion independence for at least six months following administration of the modified CD34+ hHSPCs starting three months after administration of the modified CD34+ hHSPCs;
(iv) the subject achieves transfusion reduction or transfusion independence for at least twelve months following administration of the modified CD34+ hHSPCs starting three months after administration of the modified CD34+ hHSPCs;
(v) the subject is no longer in need of iron chelation therapy within a 2 to 5 year period of the time of administration of the modified CD34+ hHSPCs, or within a 2 to 5 year period after the time of administration of the modified CD34+ hHSPCs, relative to a 2 to 5 year period before the time of administration of the modified CD34+ hHSPCs; and/or
(vi) the HbF level in the subject is at least 20% for at least three months starting at any time at or after the time of administration of the modified CD34+ hHSPCs.

13. The method of claim 7, wherein (i) the modified CD34+ hHSPCs exhibit an increase in $\gamma/(\gamma+\alpha)$-globin mRNA ratios of 0.1 to 0.5 and/or wherein the modified CD34+ hHSPCs exhibit an increase in γ/(γ+β)-globin mRNA ratios of 0.2 to 0.6; (ii) the modified CD34+ hHSPCs exhibit a HbF mean percentage of HbF/(HbF+HbA) protein levels of 15% to 50%; (iii) the modified CD34+ hHSPCs exhibit a ratio of (γ+β)/α-globin mRNA that is at or above 0.4; (iv) the modified CD34+ hHSPCs exhibit a mean allele editing frequency of 70% to 90%; (v) at least 50% of the modified CD34+ hHSPCs maintain multi-lineage potential for at least sixteen weeks after administration of the modified CD34+ hHSPCs; and/or (vi) the modified CD34+ hHSPCs exhibit an on-target indel rate of at least 40%.

14. The method of claim 7, wherein the dose is $3 \times 10^6$ CD34+ hHSPCs per kg.

15. The method of claim 7, wherein the genetic modification is produced by delivering to the CD34+ hHSPCs a Cas9 endonuclease and a guide RNA (gRNA) comprising the nucleotide sequence of SEQ ID NO: 1.

16. The method of claim 7, wherein the genetic modification is produced by delivering to the CD34+ hHSPCs a Cas9 endonuclease and a guide RNA (gRNA) comprising the nucleotide sequence of SEQ ID NO: 2.

* * * * *

UNITED STATES PATENT AND TRADEMARK OFFICE
CERTIFICATE OF CORRECTION

PATENT NO. : 12,161,674 B2
APPLICATION NO. : 16/769926
DATED : December 10, 2024
INVENTOR(S) : Ewelina Morawa et al.

Page 1 of 1

It is certified that error appears in the above-identified patent and that said Letters Patent is hereby corrected as shown below:

On the Title Page

Add the section below:
Item (60), Related U.S. Application Data
--(60) U.S. Provisional Application No. 62/594,689, filed December 5, 2017, U.S. Provisional Application No. 62/664,023, filed April 27, 2018, U.S. Provisional Application No. 62/671,770, filed May 15, 2018, U.S. Provisional Application No. 62/734,431, filed September 21, 2018, U.S. Provisional Application No. 62/734,543, filed September 21, 2018.--

Signed and Sealed this
Twenty-fifth Day of March, 2025

Coke Morgan Stewart
*Acting Director of the United States Patent and Trademark Office*

SEQUENCE LISTING

```
<160> NUMBER OF SEQ ID NOS: 3

<210> SEQ ID NO 1
<211> LENGTH: 100
<212> TYPE: RNA
<213> ORGANISM: Artificial sequence
<220> FEATURE:
<223> OTHER INFORMATION: sgRNA

<400> SEQUENCE: 1
cuaacaguug cuuuuaucac guuuuagagc uagaaauagc aaguuaaaau aaggcuaguc        60
cguuaucaac uugaaaaagu ggcaccgagu cggugcuuuu                            100

<210> SEQ ID NO 2
<211> LENGTH: 100
<212> TYPE: RNA
<213> ORGANISM: Artificial sequence
<220> FEATURE:
<223> OTHER INFORMATION: Modified sgRNA
<220> FEATURE:
<221> NAME/KEY: modified_base
<222> LOCATION: (1)..(3)
<223> OTHER INFORMATION: 2'-O-methyl-phosphorothioate nucleotides
<220> FEATURE:
<221> NAME/KEY: modified_base
<222> LOCATION: (97)..(99)
<223> OTHER INFORMATION: 2'-O-methyl-phosphorothioate nucleotides

<400> SEQUENCE: 2
cuaacaguug cuuuuaucac guuuuagagc uagaaauagc aaguuaaaau aaggcuaguc        60
cguuaucaac uugaaaaagu ggcaccgagu cggugcuuuu                            100

<210> SEQ ID NO 3
<211> LENGTH: 23
```

```
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: n is a, c, g, or t

<400> SEQUENCE: 3
nnnnnnnnnn nnnnnnnnnn nrg                                        23
```